(12) United States Patent
Virtanen

(10) Patent No.: US 6,342,349 B1
(45) Date of Patent: *Jan. 29, 2002

(54) OPTICAL DISK-BASED ASSAY DEVICES AND METHODS

(75) Inventor: Jorma Virtanen, Irvine, CA (US)

(73) Assignee: Burstein Technologies, Inc., Irvine, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/120,049

(22) Filed: Jul. 21, 1998

Related U.S. Application Data

(63) Continuation-in-part of application No. 08/888,935, filed on Jul. 7, 1997, now abandoned.
(60) Provisional application No. 60/053,229, filed on Jul. 21, 1997, provisional application No. 60/030,416, filed on Nov. 1, 1996, and provisional application No. 60/021,367, filed on Jul. 8, 1996.

(51) Int. Cl.[7] .......................... C12Q 1/68; C12P 19/34; C07H 19/00; C07H 21/00; C07H 21/02

(52) U.S. Cl. ..................... 435/6; 435/91.1; 435/91.2; 536/22.1; 536/23.1; 536/24.3; 536/25.3

(58) Field of Search ................. 435/6, 91.1, 91.2; 536/22.1, 23.1, 24.3, 25.3

(56) References Cited

U.S. PATENT DOCUMENTS

| | | |
|---|---|---|
| B13,646,346 | 2/1972 | Catt ........................... 250/83 |
| B13,654,090 | 4/1972 | Schuurs et al. ................ 435/7 |
| 3,791,932 A | 2/1974 | Schuurs et al. ....... 195/103.5 R |
| 3,817,837 A | 6/1974 | Rubenstein et al. .. 195/103.5 R |
| 3,817,838 A | 6/1974 | Harris et al. ......... 195/103.5 R |
| 3,850,752 A | 11/1974 | Schuurs et al. ....... 195/103.5 R |
| 3,939,350 A | 2/1976 | Kronick et al. ............. 250/365 |
| 3,996,345 A | 12/1976 | Ullman et al. ................ 424/12 |
| 4,037,257 A | 7/1977 | Chari .......................... 360/51 |
| 4,062,733 A | 12/1977 | Edwards et al. ......... 195/103.7 |

(List continued on next page.)

FOREIGN PATENT DOCUMENTS

| | | | |
|---|---|---|---|
| EP | 0 521 421 A2 | 1/1993 | |
| WO | WO 96/09548 | 3/1996 | ......... G01N/33/543 |
| WO | WO 96/35940 | 11/1996 | ......... G01N/21/77 |
| WO | WO 97/21090 | 6/1997 | |
| WO | WO 98/01533 | 1/1998 | |
| WO | WO 98/12559 | 3/1998 | |
| WO | WO 98/15356 | 4/1998 | |
| WO | WO 98/37238 | 8/1998 | ............ C12Q/1/68 |
| WO | WO 98/38510 | 9/1998 | ......... G01N/88/487 |
| WO | WO 99/35499 | 7/1999 | ......... G01N/33/543 |

Primary Examiner—Jezia Riley
(74) Attorney, Agent, or Firm—Oppenheimer Wolff & Donnelly LLP

(57) ABSTRACT

Optical disk-based assay devices and methods are described, in which analyte-specific signal elements are disposed on an optical disk substrate. In preferred embodiments, the analyte-specific signal elements are disposed readably with the disk's tracking features. Also described are cleavable signal elements particularly suitable for use in the assay device and methods. Binding of the chosen analyte simultaneously to a first and a second analyte-specific side member of the cleavable signal element tethers the signal-responsive moiety to the signal element's substrate-attaching end, despite subsequent cleavage at the cleavage site that lies intermediate the first and second side members. The signal responsive moiety reflects, absorbs, or refracts incident laser light. Described are nucleic acid hybridization assays, nucleic acid sequencing, immunoassays, cell counting assays, and chemical detection. Adaptation of the assay device substrate to function as an optical waveguide permits assay geometries suitable for continuous monitoring applications.

15 Claims, 51 Drawing Sheets

U.S. PATENT DOCUMENTS

| | | | |
|---|---|---|---|
| 4,104,029 A | 8/1978 | Maier, Jr. | 23/230 B |
| 4,160,645 A | 7/1979 | Ullman | 23/230 B |
| 4,233,402 A | 11/1980 | Maggio et al. | 435/7 |
| 4,275,149 A | 6/1981 | Litman et al. | 435/7 |
| 4,277,437 A | 7/1981 | Maggio | 422/61 |
| 4,287,300 A | 9/1981 | Gibbons et al. | 435/5 |
| 4,366,241 A | 12/1982 | Tom et al. | 435/7 |
| 4,472,509 A | 9/1984 | Gansow et al. | 436/548 |
| 4,542,102 A | 9/1985 | Dattagupta et al. | 435/6 |
| 4,608,344 A | 8/1986 | Carter et al. | 436/34 |
| 4,756,971 A | 7/1988 | Virtanen et al. | 428/405 |
| RE33,064 E | 9/1989 | Carter et al. | 436/34 |
| 4,877,745 A | 10/1989 | Hayes et al. | 436/166 |
| 5,021,236 A | 6/1991 | Gries et al. | 424/9 |
| 5,087,556 A | 2/1992 | Ertinghausen | 435/7.9 |
| 5,112,134 A | 5/1992 | Chow et al. | 356/427 |
| 5,118,605 A * | 6/1992 | Urdea | 435/6 |
| 5,132,097 A | 7/1992 | Van Deusen et al. | 422/82.09 |
| 5,164,319 A | 11/1992 | Hafeman et al. | 435/291 |
| 5,168,057 A | 12/1992 | Oh et al. | 435/174 |
| 5,278,048 A | 1/1994 | Parce et al. | 436/29 |
| 5,334,837 A | 8/1994 | Ikeda et al. | 250/339 |
| 5,345,213 A | 9/1994 | Semancik et al. | 338/34 |
| 5,384,261 A | 1/1995 | Winkler et al. | 436/518 |
| 5,405,783 A | 4/1995 | Pirrung et al. | 436/518 |
| 5,412,087 A | 5/1995 | McGall et al. | 536/24.3 |
| 5,424,186 A | 6/1995 | Fodor et al. | 435/6 |
| 5,429,807 A | 7/1995 | Matson et al. | 422/131 |
| 5,445,934 A | 8/1995 | Fodor et al. | 435/6 |
| 5,462,839 A | 10/1995 | deRooij et al. | 430/320 |
| 5,489,678 A | 2/1996 | Fodor et al. | 536/22.1 |
| 5,510,270 A | 4/1996 | Fodor et al. | 436/518 |
| 5,521,289 A * | 5/1996 | Hainfeld et al. | 530/391.5 |
| 5,580,696 A | 12/1996 | Yashiro | 430/270.17 |
| 5,599,662 A | 2/1997 | Respess | 435/5 |
| 5,624,711 A | 4/1997 | Sundberg et al. | 427/261 |
| 5,892,577 A | 4/1999 | Gordon | 356/73 |
| 6,030,581 A | 2/2000 | Virtanen | 422/68.1 |

* cited by examiner

Centrifugal force →

No rotation

Top View

Cross-section

Top view

Cross section

Topview

Cross section

Top View

Cross section

Cross section

To vacuum

Thin plastic film

To vacuum ⟶

To vacuum ⟶

8-Tip pipetting station

Panel

Washing buffer

Dry and read →

Water

Seal and dispose →

Start from A →

OPTICAL DISK-BASED ASSAY DEVICES AND METHODS

CROSS-REFERENCE TO RELATED APPLICATIONS

The present application is a continuation-in-part of Applicant's provisional U.S. patent application No. 60/053,229, filed Jul. 21, 1997, and of Applicant's U.S. patent application No. 08/888,935, filed Jul. 7, 1997 now abandoned, which is a continuation-in-part of provisional application Nos. 60/030,416, filed Nov. 1, 1996 and 60/021,367, filed Jul. 8, 1996. Priority is claimed to each of the above-mentioned applications, the disclosures of each of which are incorporated herein by reference.

1. FIELD OF THE INVENTION

The present invention relates to the field of analytical instrumentation for chemical assays and diagnostics, and to the detection of small quantities of analytes in samples. More specifically, the invention relates to an assay device comprising an optical disk having analyte-specific signal elements disposed readably thereon

2. BACKGROUND OF THE INVENTION

2.1 Small Scale Clinical Assays

Until recently, most clinical diagnostic assays for the detection of small quantities of analytes in fluids have been conducted as individual tests; that is, as single tests conducted upon single samples to detect individual analytes. More recently, efficiency and economy have been obtained by designing apparatus for multi-sample preparation and automated reagent addition, and by designing apparatus for rapid analysis of large numbers of test samples, either in parallel or in rapid serial procession. Often, such automated reagent preparation devices and automated multiplex analyzers are integrated into a single apparatus.

Large clinical laboratory analyzers of this type can accurately perform hundreds of assays automatically, or semi-automatically, in one hour. However, these analyzers are expensive and only centralized laboratories and large hospitals can afford them. Such centralization necessitates sample transport, and often precludes urgent or emergent analysis of time-critical samples.

Thus, there exists a strong need for simplified clinical assays that will both reduce the cost of such dedicated analyzers and further their distribution. The limit of such effort is the design of clinical tests suitable for use at the patient bedside or in the patient's home without dedicated detectors. Blood glucose and pregnancy tests are well known examples.

Although useful tests of this sort have been offered for many years, a major breakthrough was the introduction of solid phase immunoassays and other strip tests since approximately 1980. Most notable are Advance® test (Johnson & Johnson), RAMP™ hCG assay (Monoclonal Antibodies, Inc.), Clear Blue Easy™ (Unipath Ltd.) and ICON (Hybritech).

Clear Blue Easy™ has all reagents in a laminated membrane and uses conjugated colored latex microbeads as the signal reagent. It uses a capillary migration immunoconcentration format. The ICON is a dual monoclonal sandwich immunoconcentration assay. This assay has been rendered quantitative through the use of a small reflectance instrument. Otherwise, all these methods are only qualitative.

Migration distance can be used as a basis for quantitative assays Commercially available are Quantab™ (Environmental Test Systems), AccuLevel® (Syva), AccuMeter® (ChemTrak), Clinimeter™ (Crystal Diagnostics) and Q.E.D.™ (Enzymatics). One of the newest is a thermometer-type assay device (Ertinghausen G., U.S. Pat. No. 5,087,556) that is not yet commercially available. These systems can be used to assay general chemistry analytes, such as cholesterol, as well as blood levels of therapeutic drugs.

One disadvantage, however, of each of these formats is that only one, or a very limited number, of assays can conveniently be performed simultaneously.

To fill the gap between massive analyzers and strips, some small instruments have been developed. The most notable is Eclipse ICA™ (Biotope, Inc.). This device is a bench-top, random-access, automated centrifugal immunoassay and chemistry system. Patient samples are pipetted into cassettes that are placed into a rotor. Sixteen tests can be run in approximately 17 minutes. The results are measured by UV/Visual spectrometry or by fluorometry. Four different types of cassette are needed. Each cassette has a relatively complicated structure.

Despite these developments, there still exists a need for a simple device that can easily be used for multiple quantitative assays, and preferably requiring no specialized detector instrumentation.

2.2 Spatially-Addressable Probe Arrays

Recently, spatially addressable arrays of different biomaterials have been fabricated on solid supports. These probe arrays permit the simultaneous analysis of a large number of analytes. Examples are arrays of oligonucleotides or peptides that are fixed to a solid support and that capture complementary analytes. One such system is described by Fodor et al., Nature, Vol. 364, Aug. 5, 1993. Short oligonucleotide probes attached to a solid support bind complementary sequences contained in longer strands of DNA in liquid sample; the sequence of the sample nucleic acids is then calculated by computer based on the hybridization data so collected.

In the assay system described by Fodor et al., the array is inverted on a temperature regulated flow cell against a reservoir containing the tagged target molecules. In order to distinguish the surface bound molecules, the system requires an extremely sensitive detector.

Accordingly, there remains a need for an economical system to fabricate spatially addressable probe arrays in a simplified format that provides both for ready detection and the ability to assay for large numbers of test substances (i.e. analytes) in a fluid test sample in a single step, or a minimum number of steps, or assay for a single test substance or analyte in a large number of fluid test samples.

2.3 Spatially Addressable Laser-Based Detection Systems

Several devices for consumer electronic use permit spatially addressable detection of digital information. In particular, several formats have been developed based on the information recording potential of differential reflectance and transmittance.

In conventional audio or CD-ROM compact disks, digital information—or digitally encoded analog information—is encoded on a circular plastic disk by means of indentations in the disk. Typically, such indentations are on the order of one-eighth to one-quarter of the wavelength of the incident beam of a laser that is used to read the information present on the disk. The indentations on the disk cause destructive interference within the reflected beam, which corresponds to a bit having a "zero" value. The flat areas of the disk reflect the laser light back to a detector and the detector gives a value of "one" to the corresponding bit.

In another convention, a change of intensity of a reflected light gets a value of one while a constant intensity corresponds to zero.

Since the indentations have been formed in the disk in a regular pattern from a master copy containing a predetermined distribution of bits of "zero" and bits of "one", the resultant signal received by the detector is able to be processed to reproduce the same information that was encoded in the master disk.

The standard compact disk is formed from a 12 cm polycarbonate substrate, a reflective metalized layer, and a protective lacquer coating. The format of current CDS and CD-ROMs is described by the ISO 9660 industry standard, incorporated herein by reference.

The polycarbonate substrate is optical-quality clear polycarbonate. In a standard pressed, or mass-replicated CD, the data layer is part of the polycarbonate substrate, and the data are impressed in the form of a series of pits by a stamper during the injection molding process. During this process, molten polycarbonate is injected into a mold, usually under high pressure, and then cooled so that the polycarbonate takes on the shape of the mirror image of the mold, or "stamper" or "stamp"; pits that represent the binary data on a disc's substrate are therefore created in and maintained by the polycarbonate substrate as a mirror image of the pits of the stamper created during the mastering process. The stamping master is typically glass.

Pits are impressed in the CD substrate in a continuous spiral. The reflective metal layer applied thereupon, typically aluminum, assumes the shape of the solid polycarbonate substrate, and differentially reflects the laser beam to the reading assembly depending on the presence or absence of "pits." An acrylic lacquer is spincoated in a thin layer on top of the metal reflective layer to protect it from abrasion and corrosion.

Although similar in concept and compatible with CD readers, the information is recorded differently in a recordable compact disk (CD-R). In CD-R, the data layer is separate from the polycarbonate substrate. The polycarbonate substrate instead has impressed upon it a continuous spiral groove as an address for guiding the incident laser. An organic dye is used to form the data layer. Although cyanine was the first material used for these discs, a metal-stabilized cyanine compound is generally used instead of "raw" cyanine. An alternative material is phthalocyanine. One such metallophthalocyanine compound is described in U.S. Pat. No. 5,580,696.

In CD-R, the organic dye layer is sandwiched between the polycarbonate substrate and the metalized reflective layer, usually 24 carat gold, but alternatively silver, of the media. Information is recorded by a recording laser of appropriate preselected wavelength that selectively melts "pits" into the dye layer—rather than burning holes in the dye, it simply melts it slightly, causing it to become non-translucent so that the reading laser beam is refracted rather than reflected back to the reader's sensors, as by a physical pit in the standard pressed CD. As in a standard CD, a lacquer coating protects the information-bearing layers.

Other physical formats for recording and storing information are being developed based on the same concept as the compact disk: creation of differential reflectance or transmittance on a substrate to be read by laser.

One such format is termed Digital Video Disc (DVD). A DVD looks like standard CD: it is a 120 mm (4.75 inch) disk that appears as a silvery platter, with a hole in the center for engaging a rotatable drive mechanism. Like a CD, data is recorded on the disc in a spiral trail of tiny pits, and the discs are read using a laser beam. In contrast to a CD, which can store approximately 680 million bytes of digital data under the ISO 9660 standard, the DVD can store from 4.7 billion to 17 billion bytes of digital data. The DVD's larger capacity is achieved by making the pits smaller and the spiral tighter, that is, by reducing the pitch of the spiral, and by recording the data in as many as four layers, two on each side of the disc. The smaller pit size and tighter pitch require that the reading laser wavelength be smaller. While the smaller wavelength is backward compatible with standard pressed CDS, it is incompatible with current versions of the dye-based CD-R.

The following table compares DVD and CD characteristics:

TABLE 1

Comparison of DVD and CD Characteristics

| | DVD | CD |
| --- | --- | --- |
| Diameter | 120 mm | 120 mm |
| Disc Thickness | 1.2 mm | 1.2 mm |
| Substrate Thickness | 0.6 mm | 1.2 mm |
| Track pitch | 0.74 $\mu$m | 1.6 $\mu$m |
| Minimum pit size | 0.4 $\mu$m | 0.83 $\mu$m |
| Laser wavelength | 635/650 nm | 780 nm |
| Data capacity | 4.7 gigabytes/layer/side | 0.68 gigabytes |
| Layers | 1, 2, or 4 | 1 |

Thus, a single sided/single layer DVD can contain 4.7 GB of digital information. A single sided/dual layer DVD can contain 8.5 GB of information. A Dual sided/single layer disk can contain 9.4 GB of information, while a dual sided, dual layer DVD contains up to 17 GB of information.

Each of the variations consists of two 0.6 mm substrates that are bonded together. Depending on the capacity, the disc may have one to four information layers. In the 8.5 GB and 17 GB options, a semi-reflector is used in order to access two information layers from one side of the disc.

For the 8.5 GB DVD and 17 GB options, the second information layer per side may be molded into the second substrate or may be added as a photopolymer layer. In either case, a semi-reflector layer is required to allow both information layers to be read from one side of the disk. For the 17 GB DVD, it is necessary to produce two dual-layer substrates, and bond them together.

The DVD laser reader is designed to adjust its focus to either layer depth so that both of them can be quickly and automatically accessed.

All three of the above-described formats require that the platter be spun. The nominal constant linear velocity of a DVD system is 3.5 to 4.0 meters per second (slightly faster for the larger pits in the dual layer versions), which is over 3 times the speed of a standard CD, which is 1.2 mps.

Near-field optical storage disks (TeraStor, San Jose, CA) offer even higher density information storage than DVD. In such devices, the reading head is as close as 150 nm from the disk, and the pit size and track pitch are also of nanometer scale.

Holographic data storage disks offer perhaps the highest known data storage density. Holographic recording exploits three spatial dimensions.

Despite the spatial addressability and high information density of optical media, these media have not previously been thought useful for detection of analytes.

2.4 Waveguide Detection

Waveguides have been used for chemical detection at least since 1982, U.S. Pat. No. 4,608,344, Re. 33,064, incorporated herein by reference. Absorbing and nonabsorbing analytes can be observed with waveguides. The exponential decay of the evanescent wave in uncoated waveguides is sensitive to the absorbance and the refractive index of the surrounding medium. This also affects the intensity of the light that is transmitted by the waveguide. Existing applications of waveguides to detection of analytes show poor spatial resolution.

3. SUMMARY OF THE INVENTION

The present invention solves these and other problems in the art by providing an assay device for detecting analyte, comprising an optical disk having analyte-specific signal elements disposed readably thereon. The optical disk may be read, and the analyte detection thus performed, using optical disk readers useful for reading digitally-encoded information, such as those capable of reading audio CD disks, CD-ROM disks, DVD disks, DIVX disks, laser disks, near-field storage disks, or holographic data storage disks.

In preferred embodiments, the analyte-specific signal elements are disposed readably with the optical disk's tracking features: that is, the analyte-specific signal elements are readable by the optics used for tracking, although modified or additional optics are not thereby precluded.

In a preferred embodiment of the assay device, the analyte-specific signal elements are cleavable.

In a particularly preferred embodiment, the cleavable signal element comprises: a cleavable spacer having a substrate-attaching end, a signal-responsive end, and a cleavage site intermediate the substrate-attaching end and the signal-responsive end. The cleavable signal element further includes a signal responsive moiety attached to the cleavable spacer at its signal responsive end.

A first side member (also termed side element or side arm) adapted to bind a first site on a chosen analyte, and a second side member adapted to bind a second site of the same analyte, are present on the signal element. The first and second side members confer analyte specificity upon the cleavable signal element.

The first side member is attached to the cleavable spacer intermediate the signal responsive end and cleavage site, and the second side member is attached to the cleavable spacer intermediate the spacer's cleavage site and substrate attaching end.

Binding of the chosen analyte simultaneously to the first and second side members of a cleavable signal element tethers, or constrains, the signal-responsive moiety to the signal element's substrate-attaching end, despite subsequent cleavage at the cleavage site that lies intermediate the first and second side members; conversely, failure to bind the chosen analyte simultaneously to the first and second side members of a cleavable signal element permits loss, through cleavage, of that signal element's signal-responsive moiety. The presence or absence of signal after contact with sample and contact with cleavage agent signals the presence or absence of analyte, respectively.

Typically, the signal responsive moiety of the cleavable signal element is adapted to reflect, scatter, or absorb incident light, particularly incident laser light. In preferred embodiments, the signal responsive moiety is a metal microsphere, and most preferred, a gold microsphere, most preferably a gold microsphere of diameter between 1–3 $\mu$m. These embodiments are suitable for detection in existing optical disk readers, such as those used to read audio CD, CD-ROM, DVD, laser disks, near-field optical disks, or the like.

Whether cleavable or no, the analyte-specific signal elements are disposed in or on the assay device in a spatially-addressable pattern.

In another aspect, the invention provides a method of assaying for analyte, comprising the steps of contacting the assay device with a sample, and then detecting, using an optical disk reader, analyte-specific signals therefrom.

In preferred embodiments of this aspect of the invention, the method is performed with assay devices in which the analyte-specific signal elements are cleavable, and the method comprises: contacting the assay device with a sample, cleaving the cleavable signal elements, and then detecting the signal responsive moiety of analyte-constrained cleaved signal elements.

In a related aspect, the invention provides a method of using an optical disk reader to assay for analyte. The method comprises the step of detecting, from an optical disk, analyte-specific signal elements disposed readably with the disk's tracking features. In preferred embodiments, the method comprises detecting analyte-specific signals from an assay device in which the analyte-specific signal elements are cleavable, and signal is detected from analyte-constrained cleaved signal elements.

The invention further provides a method of making an assay device for detecting analyte, comprising: disposing analyte-specific signal elements on an optical disk readably with said disk's tracking features.

The signaling element, assay devices and assay methods of the present invention are useful both for the detection of a large number of different analytes in a test sample and the detection of a single analyte in a large number of samples, both quantitatively and qualitatively.

Another aspect of the present invention is to adapt existing assay methods to employ the assay devices of the invention, including the cleavable signal element-based assay devices. Generally, an assay adapted to use the cleavable signal element-based assay device of the present invention comprises the steps of: contacting the assay device with a liquid sample, contacting the assay device with a cleaving agent adapted to cleave said plurality of attached cleavable signal elements, and detecting the presence of the signal responsive moiety of analyte-restrained cleaved signal elements adherent to the solid support substrate.

The spatial addressability of signal elements on the assay device permits identification of analytes bound to distinct signal elements, including identification of multiple analytes in a single assay.

The invention thus provides, in one preferred embodiment of this aspect, nucleic acid hybridization assays, in which the first and second side members of the cleavable signal elements include oligonucleotides. Simultaneous binding of a nucleic acid present in the assay sample to the first and second side members of the cleavable signal element prevents loss, through cleavage, of the signal element's signal-responsive end.

In another aspect, the invention provides an assay device comprising cleavable signal elements responsive to a plurality of nucleic acid sequences. This aspect of the invention provides a device and method suitable for sequencing nucleic acid through the spatial addressability of signals generated upon contact with a sample containing nucleic acid.

The invention further provides immunoassays. In these embodiments, the specificity-conferring side members of the cleavable signal elements include antibodies, antibody fragments, or antibody derivatives. Simultaneous binding of an analyte to the antibody of the first side member and the antibody of the second side member prevents the loss, through cleavage, of the signal element's signal-responsive end.

The invention also provides chemical detection assays, in which properly chosen reactive groups on a first and second side member react specifically with functional groups on the chosen analyte to secure the signal responsive moiety to the assay device substrate.

The invention further provides means for detecting electromagnetic radiation. Extremely high resolution X-ray pictures can be exposed and stored on the disk in a format suitable for direct reading on an optical disk reader, such as a CD-ROM or DVD reader, or the like. Other wavelengths of the electromagnetic spectrum are analogously detectable.

The invention also provides means for the detection and counting of cells, and for measuring their dimensions and shapes. In these embodiments, specificity-conferring recognition molecules are disposed upon the assay device substrate. The cells adhere thereto, and are detectable upon binding of signal responsive moieties conjugated to a second cellular recognition molecule Cell recognition molecules include antibodies, receptors, ligands, and adhesion molecules.

In another aspect, the invention provides assay devices that further comprise encoded digital information in the form of computer software.

Another aspect of the present invention provides a monitoring device, comprising an optical disk having a plurality of analyte-specific signal elements, wherein the optical disk is adapted to function as an optical waveguide and the analyte-specific signal elements are so disposed that specific binding of analyte detectably alters the light-transmitting properties of said optical waveguide. This device is suitable for continuous, or repeated, monitoring for presence of analyte. In preferred embodiments of this aspect of the invention, the analyte-specific signal elements are cleavable.

The invention further provides a method of monitoring for presence of analyte, comprising: contacting the monitoring device with a sample, and then detecting alterations in the light-transmitting properties of said monitoring device's optical waveguide. In a related aspect, the invention provides a method of monitoring for presence of analyte, comprising: contacting the monitoring device having cleavable signal elements with a sample, detecting alterations in the light-transmitting properties of said monitoring device's optical waveguide, cleaving the signal elements, and then detecting the signal responsive moiety of analyte-restrained cleaved signal elements.

The invention further provides assay devices in which the analyte-specific signal elements are disposed on a solid support substrate fashioned other than in a disk. In preferred embodiments of this aspect of the invention, readable by a laser-based optical reader, the signal elements are disposed readably with the support substrate's tracking and/or addressing features. Additionally, the assay device substrates may be fashioned as strips, cuvettes, test tubes, well plates, slides, gels, magnetic disks, silicon and other chips.

It is another aspect of the present invention to provide a multiwell sample application plate suitable for applying liquid samples in parallel to the assay devices of the present invention. In one embodiment, the sample application device provides a multiwell plate with a renewable surface film.

The invention further provides instrumentation to ensure correct registration of a sample application device and the assay device. The instrument may optionally comprise magnets to facilitate interaction of the sample with the assay site and/or to remove unbound molecules or particles.

4. BRIEF DESCRIPTION OF THE DRAWINGS

The invention will be better understood by reference to the following drawings, in which.

Figure 2A:
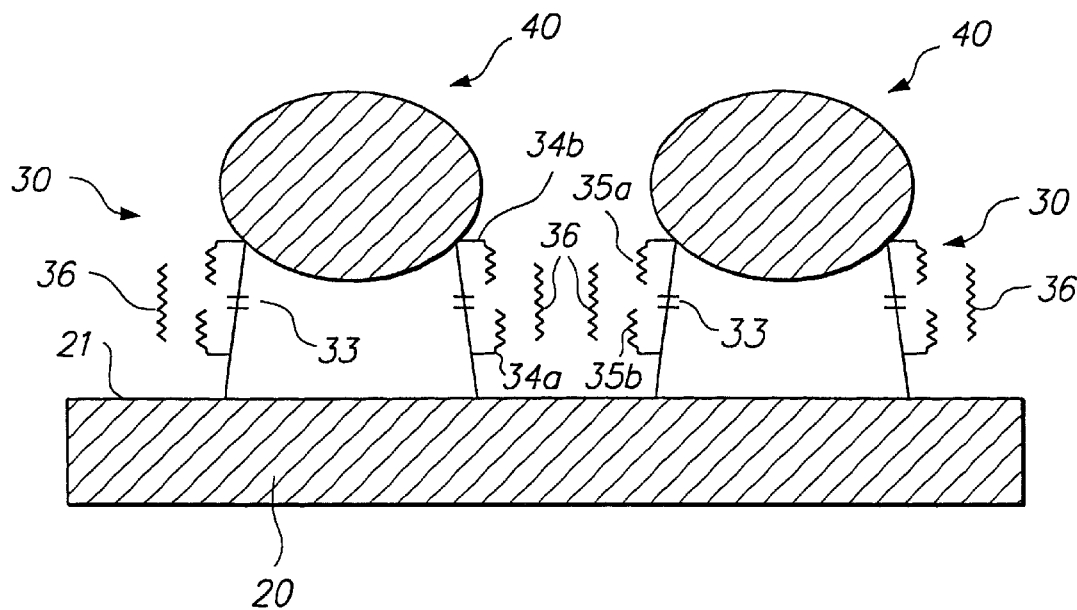
FIG. 2A is a schematic representation of a nucleic acid hybridization assay adapted to use the cleavable reflective signal elements of the present invention, shortly after introduction of a sample containing nucleic acids.
Figure 2B:
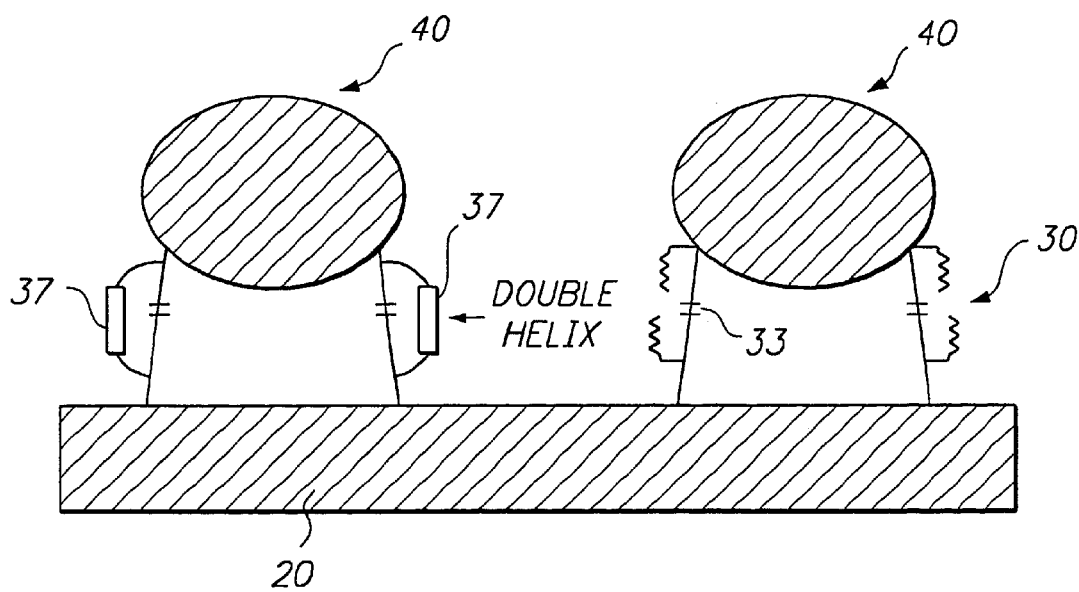
FIG. 2B is a schematic representation of a later stage of the assay procedure of FIG. 2A, in which oligonucleotides present in the sample have bound to complementary oligonucleotide side members of a first cleavable signal element, but have not bound to a second, different, set of oligonucleotide side members of a second cleavable signal element.
Figure 2C:
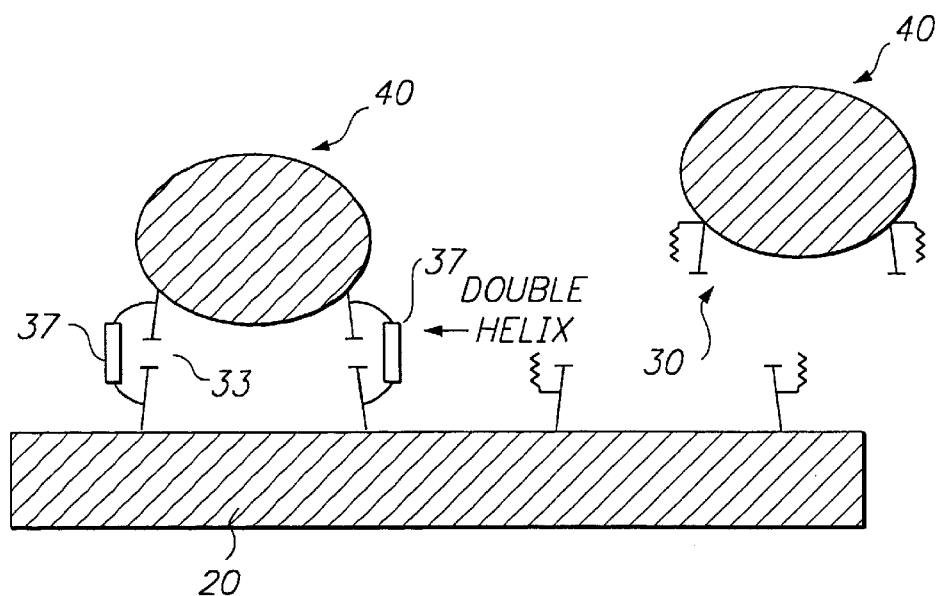
FIG. 2C is a schematic representation of a later stage of the assay procedure of FIGS. 2A and 2B, following cleavage of the spacer molecules. The reflective gold microsphere that is not tethered by the specific hybridization of complementary oligonucleotides from the test sample is removed from the surface of the assay device, providing a spatially-addressable, differentially reflective signal.
Figure 2D:
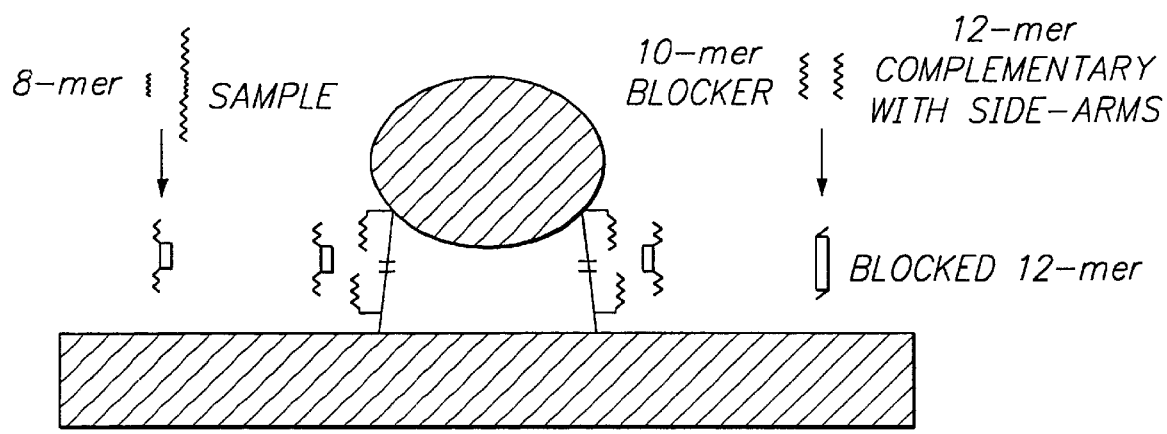
FIGS. 2D–2E are schematic representations of one aspect of the invention in which a soluble oligonucleotide added to the test sample increases sensitivity in a nucleic acid hybridization assay.
Figure 2E:
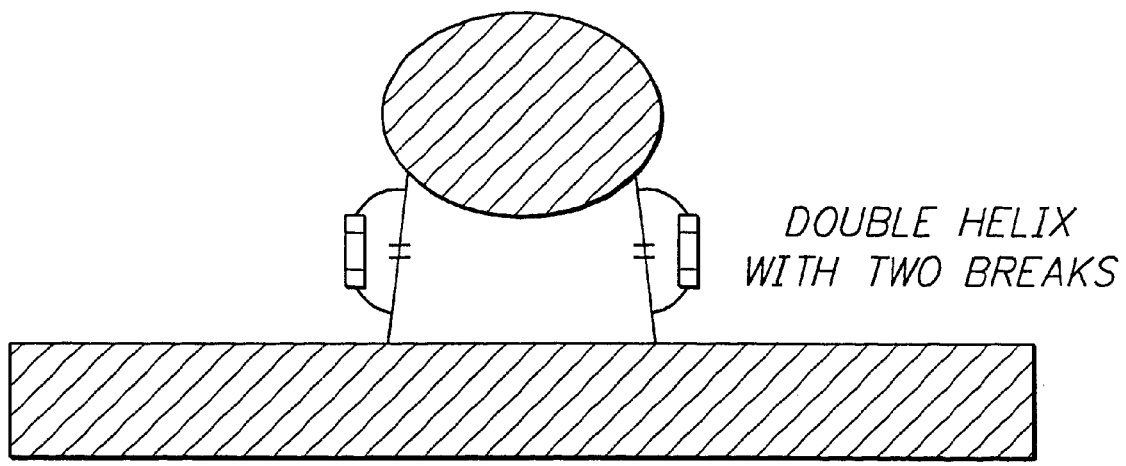
Figure 2F:
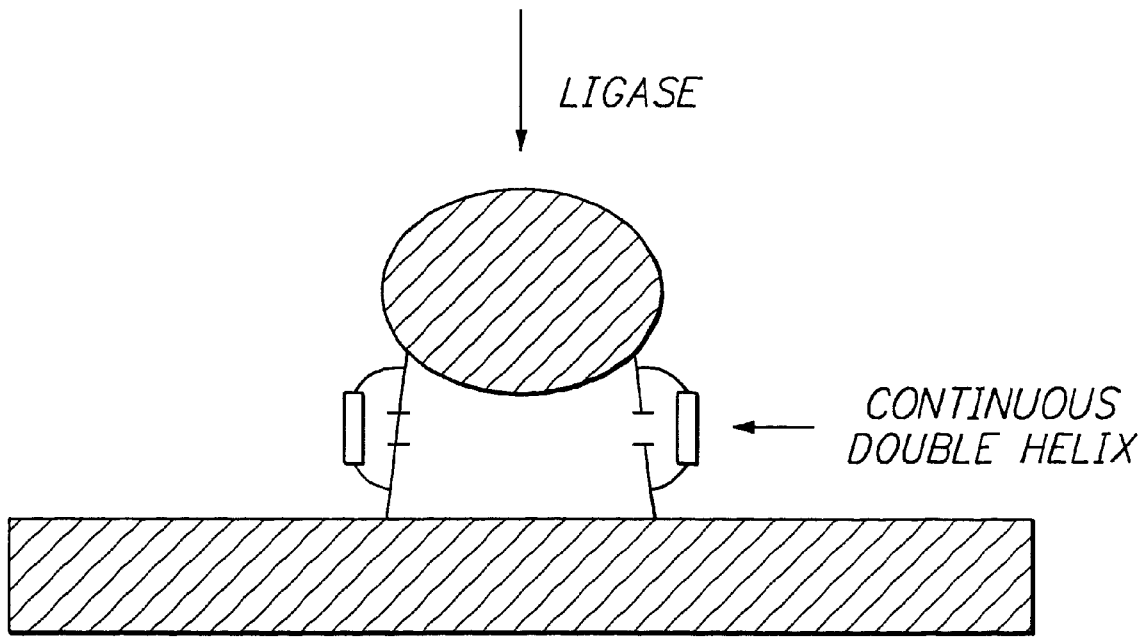
Figure 3A:
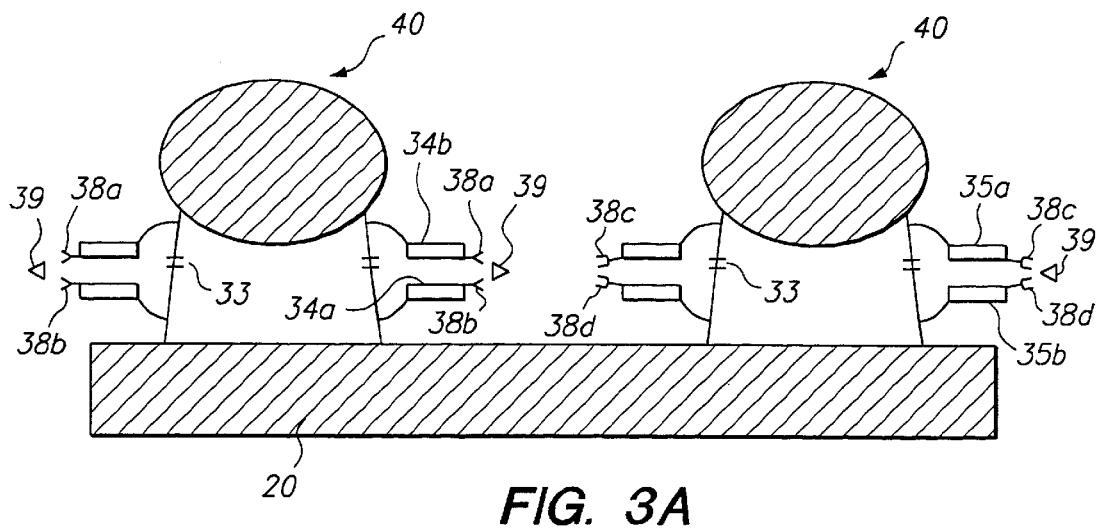
Figure 3B:
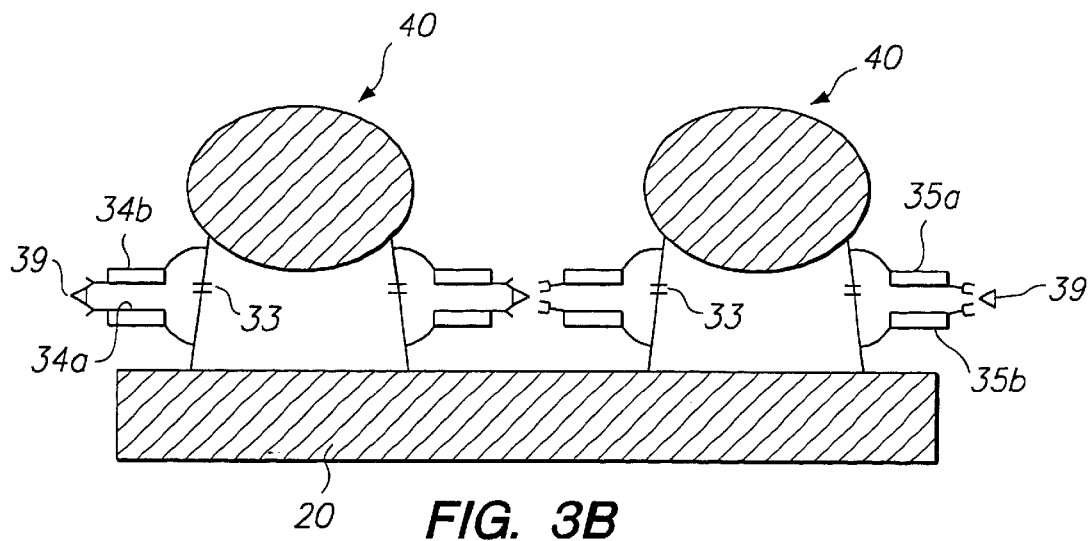
Figure 3C:
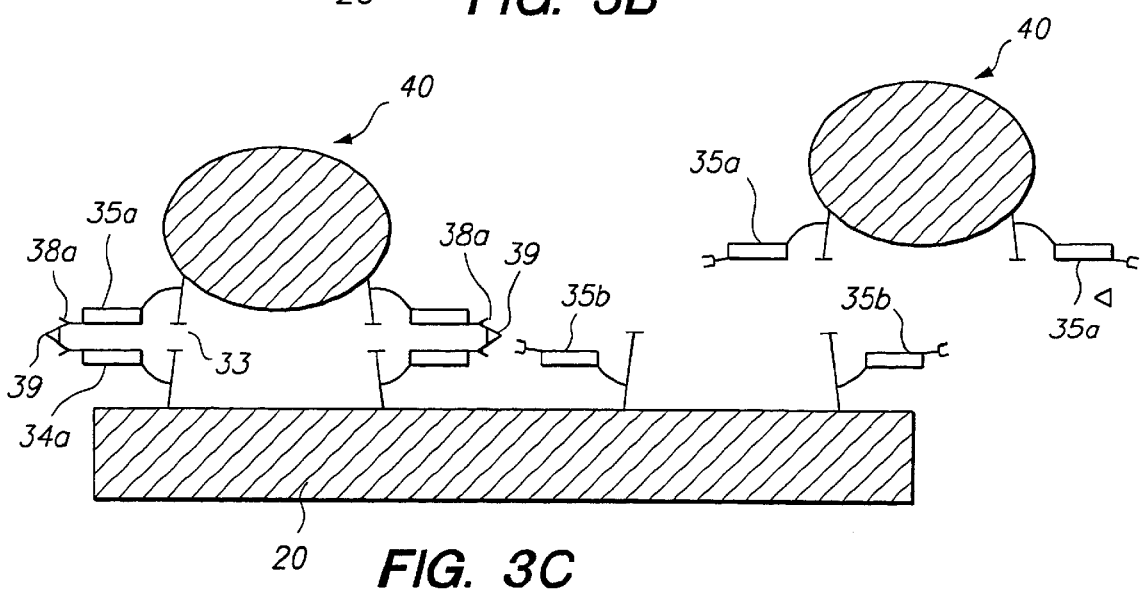
Figures 5, 6:
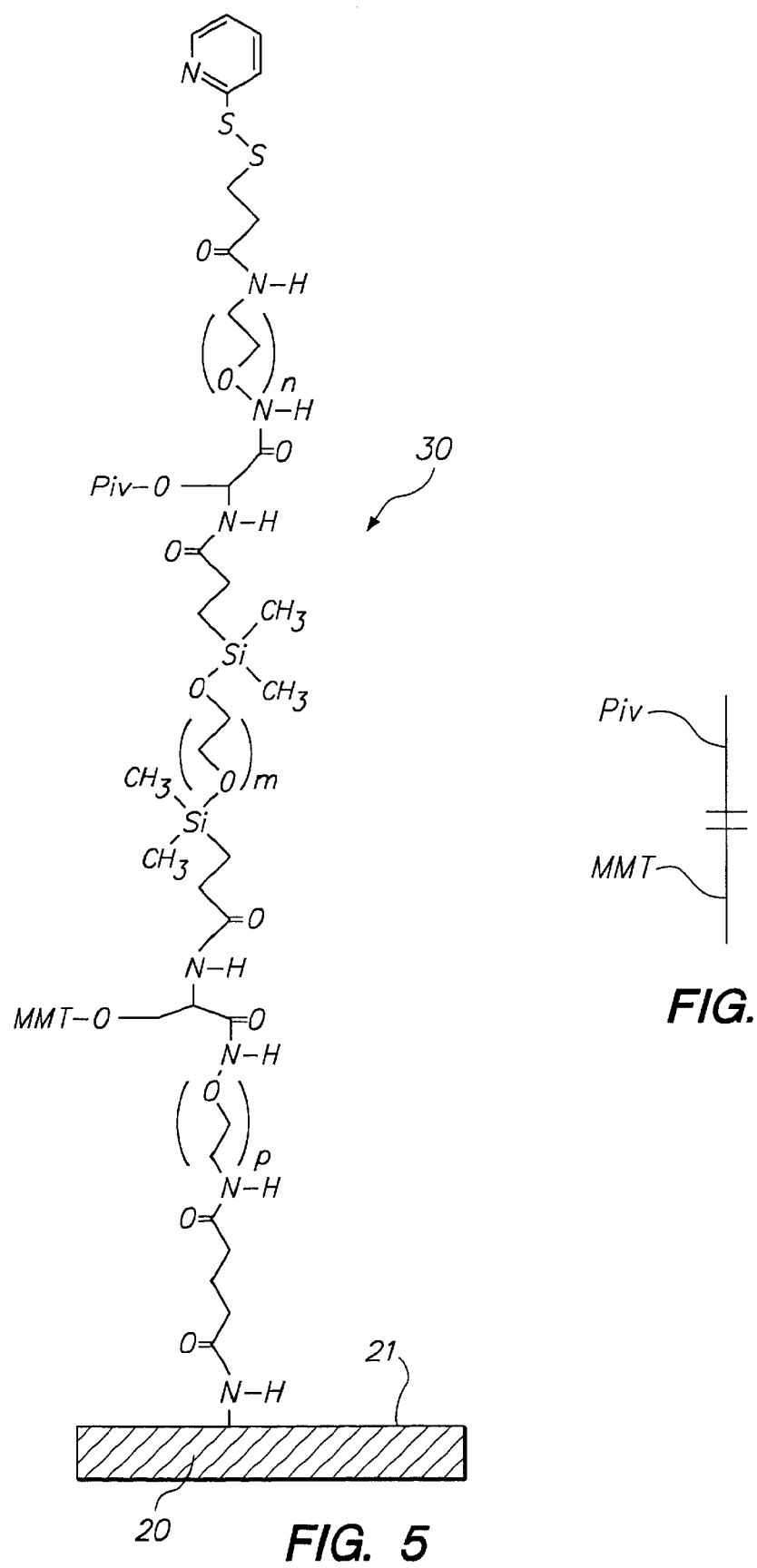
Figure 7A:
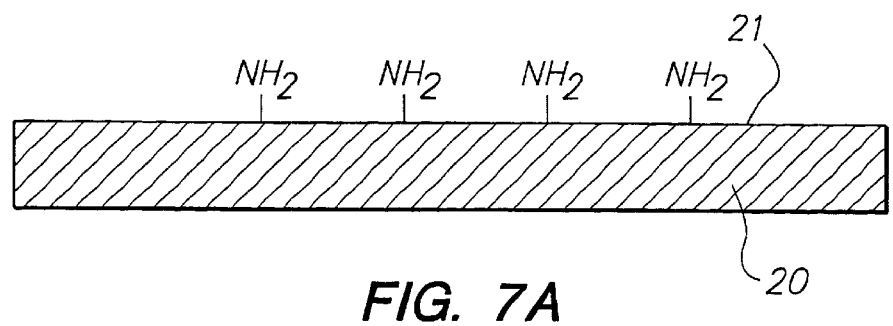
Figure 7B:
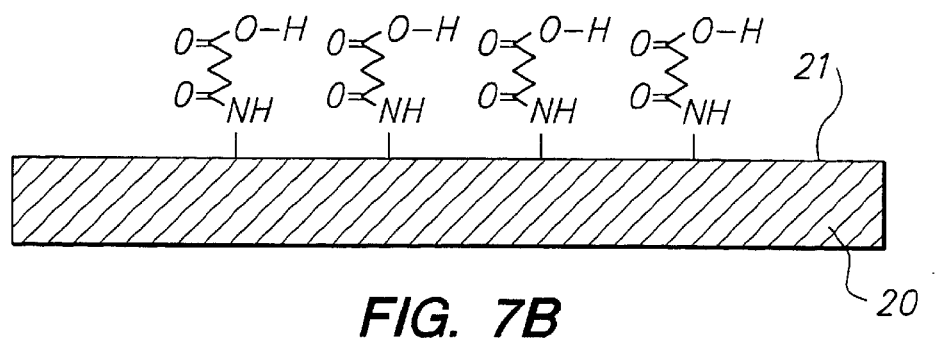
Figure 7C:
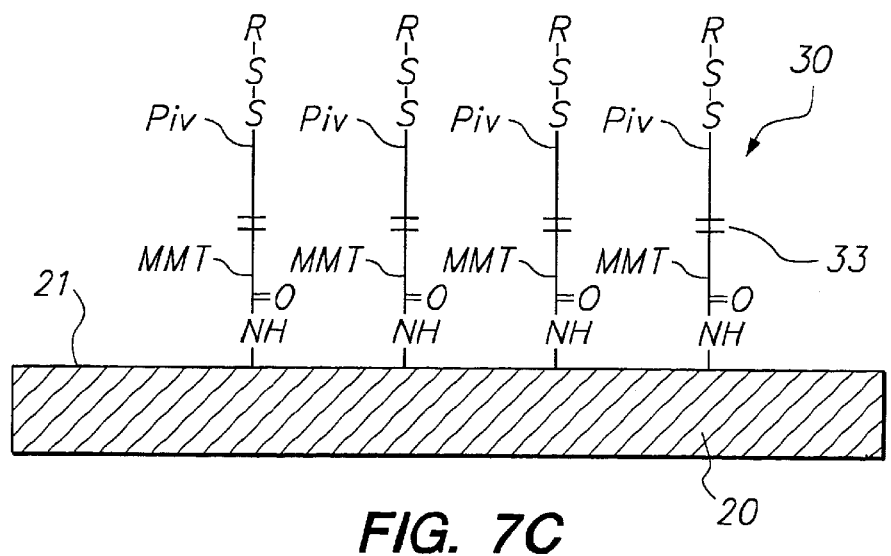
Figure 8A:
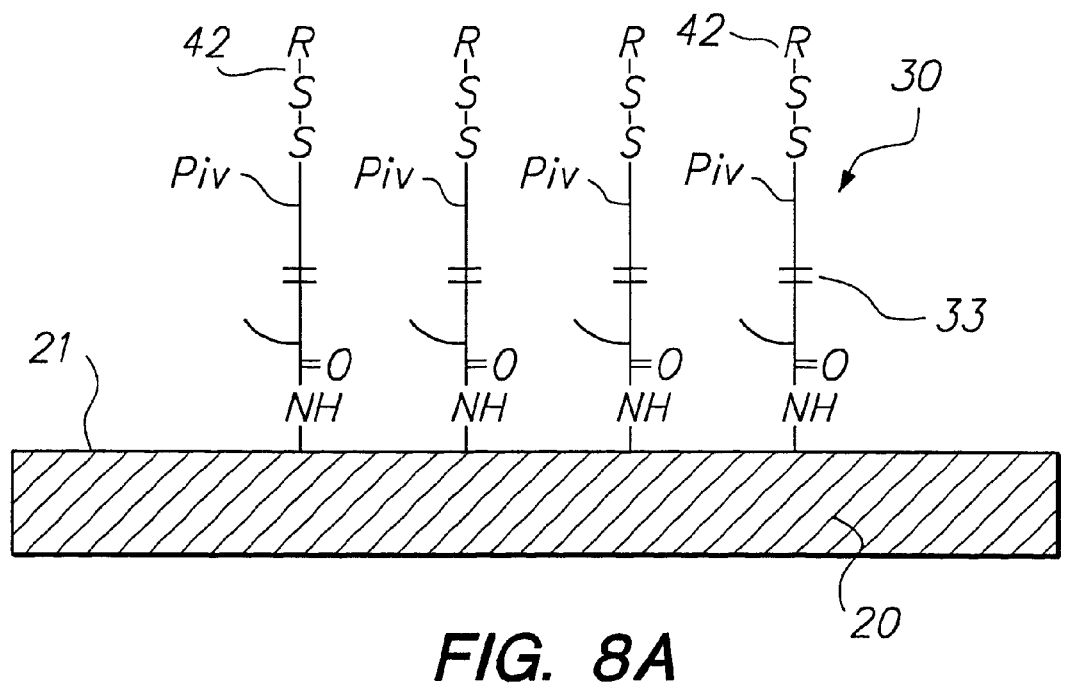
Figure 8B:
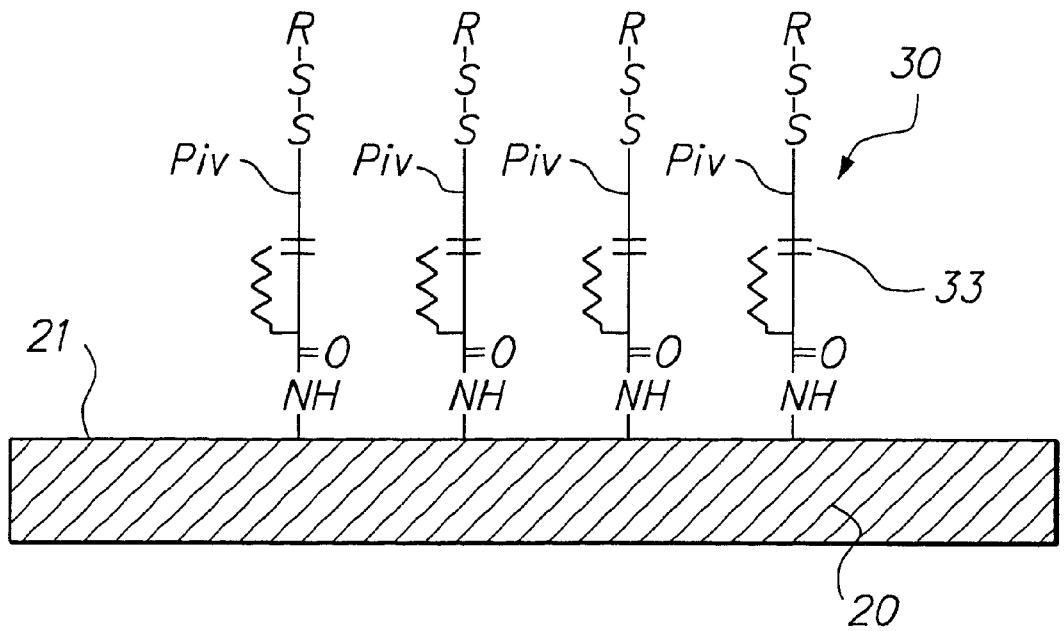
Figure 9A:
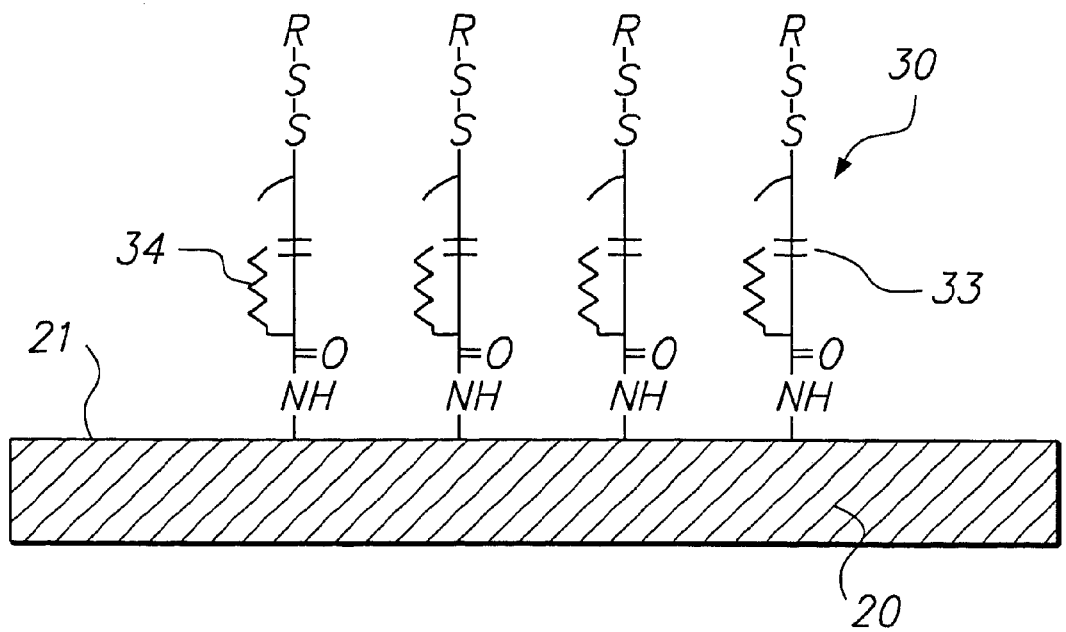
Figure 9B:
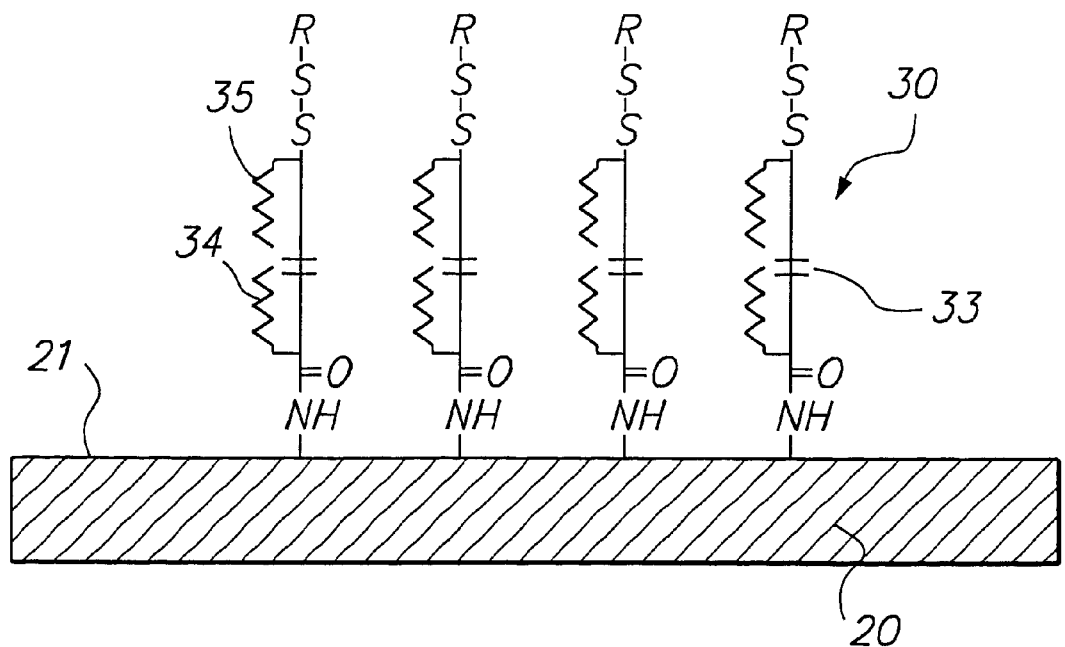
Figure 10A:
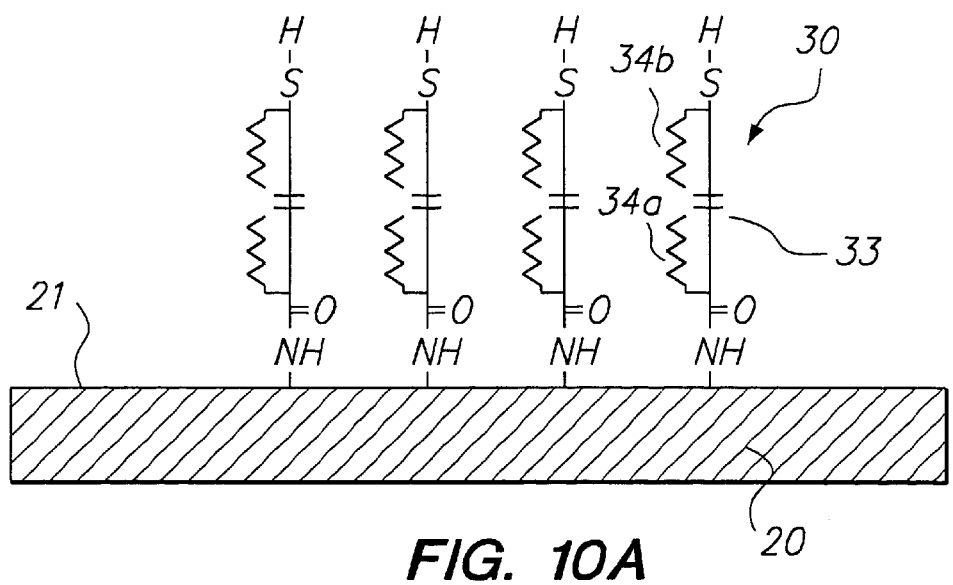
Figure 10B:
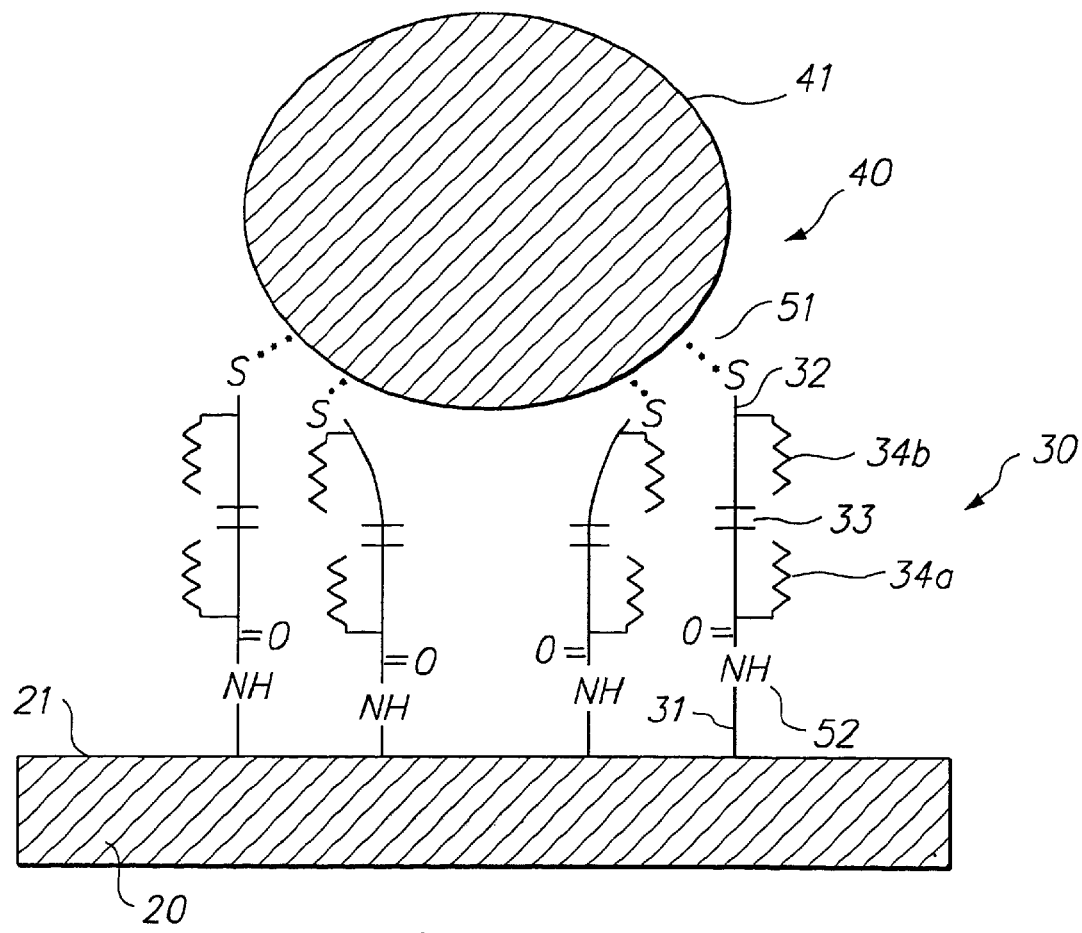
Figure 11A:
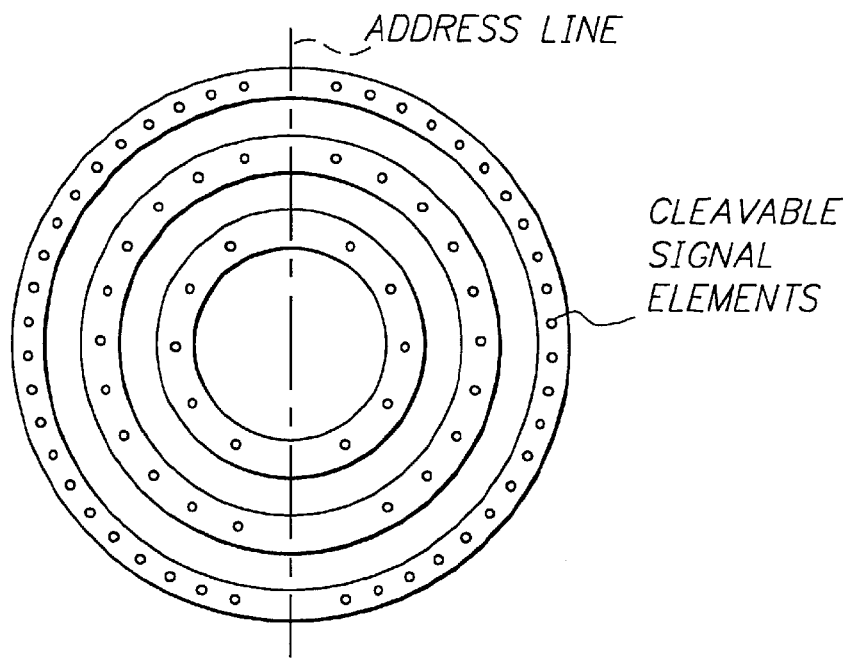
Figure 11B:
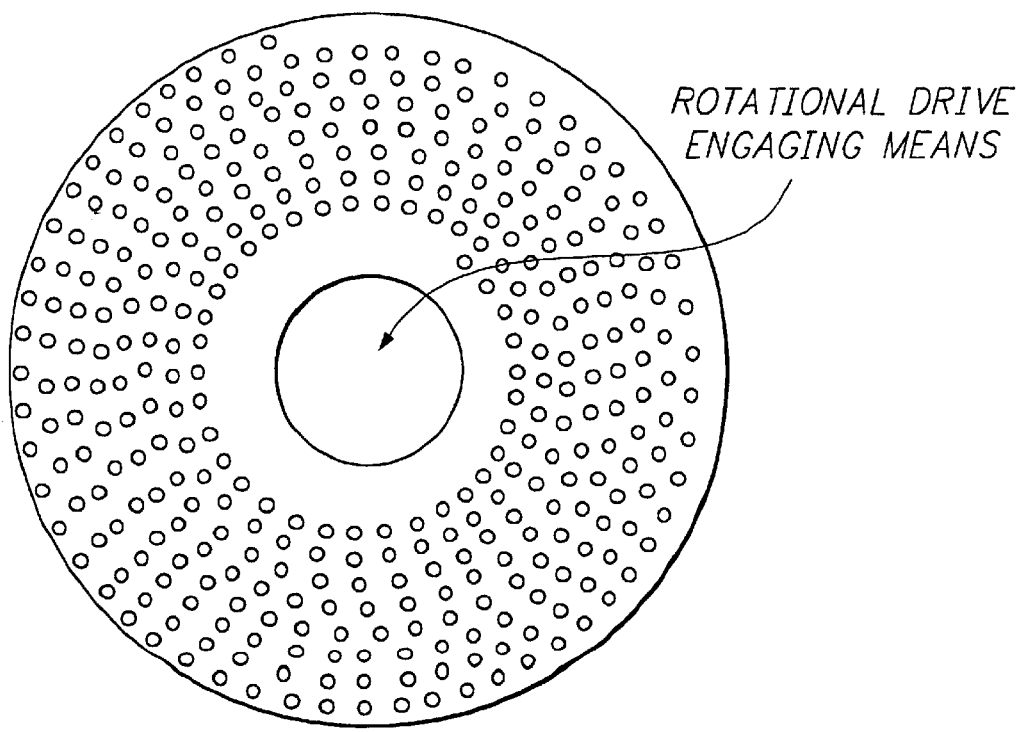
Figure 11C:
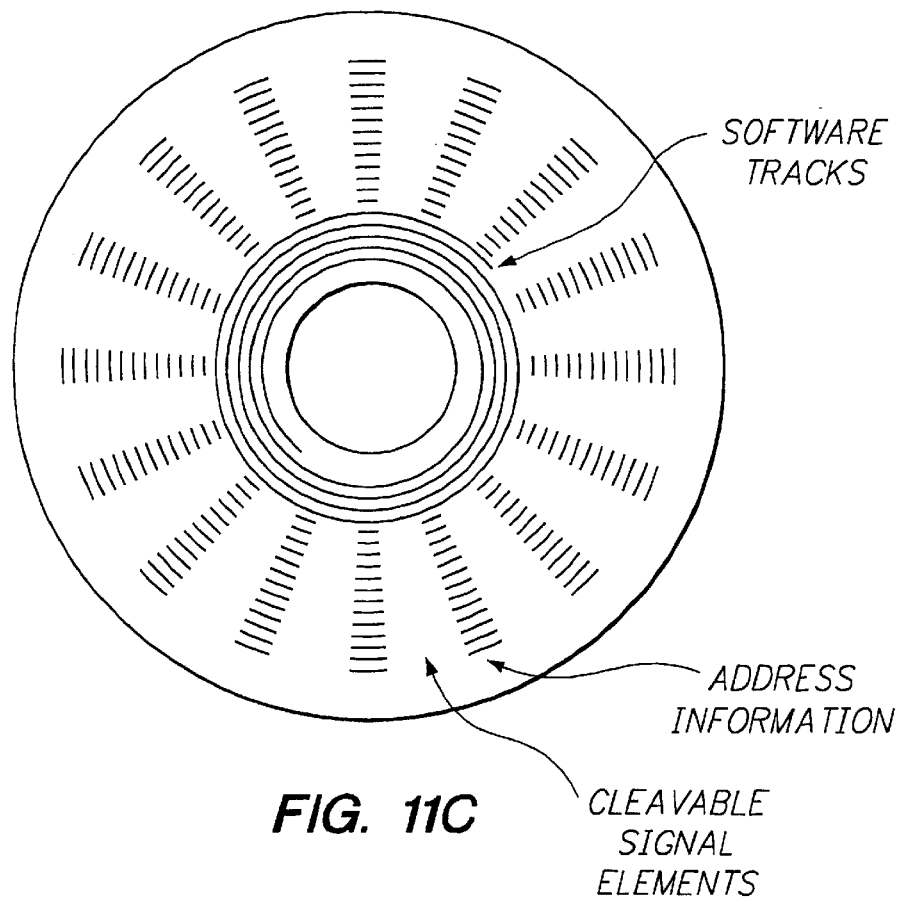
Figure 11D:
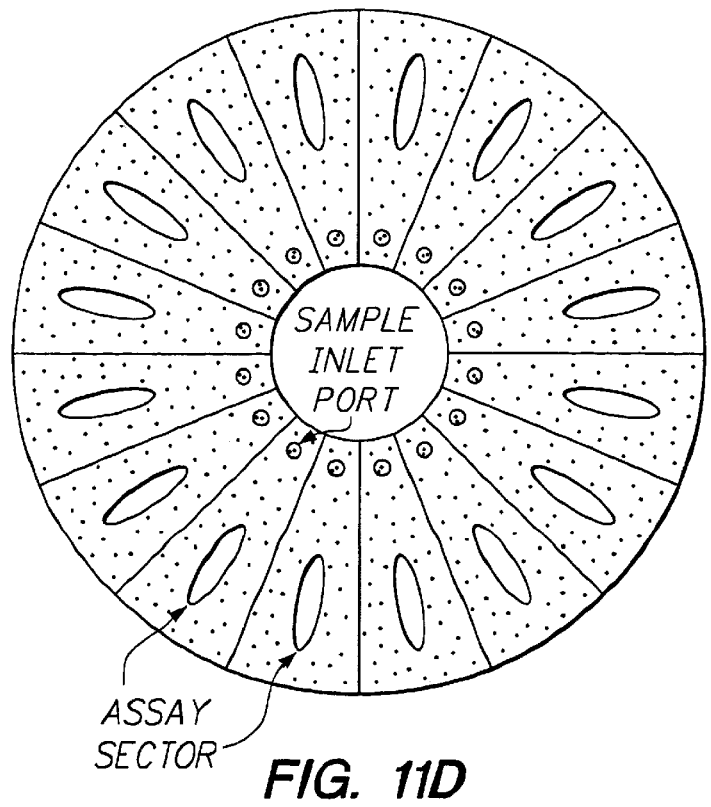
Figure 11E:
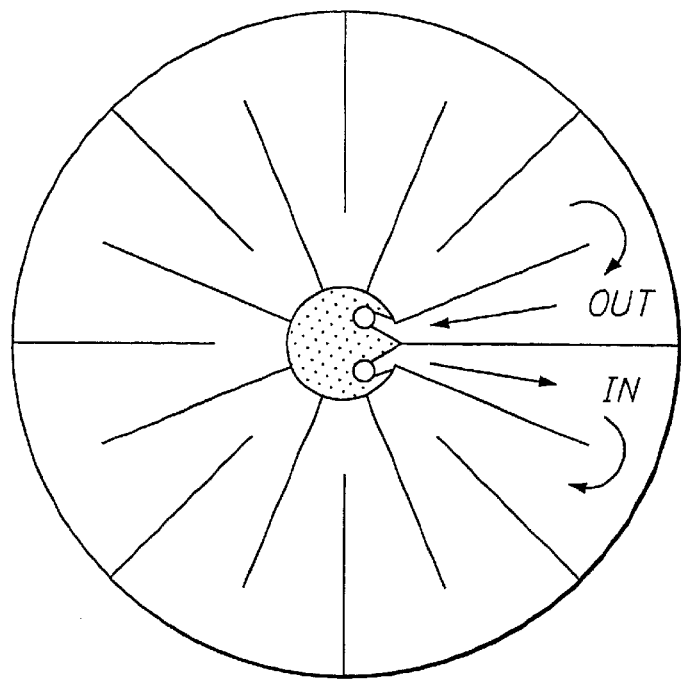
Figure 11F:
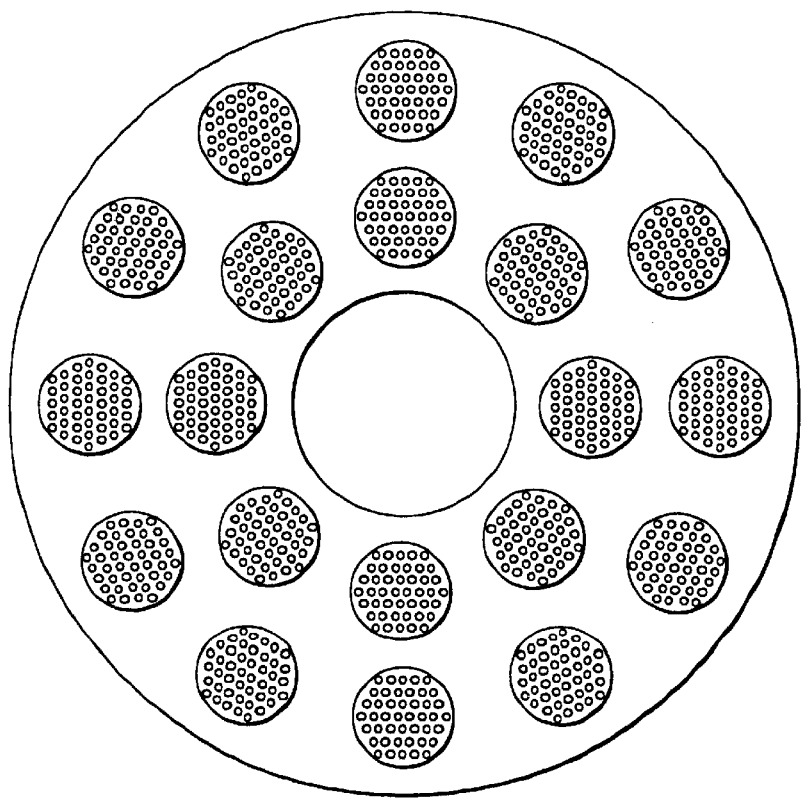
Figure 11G:
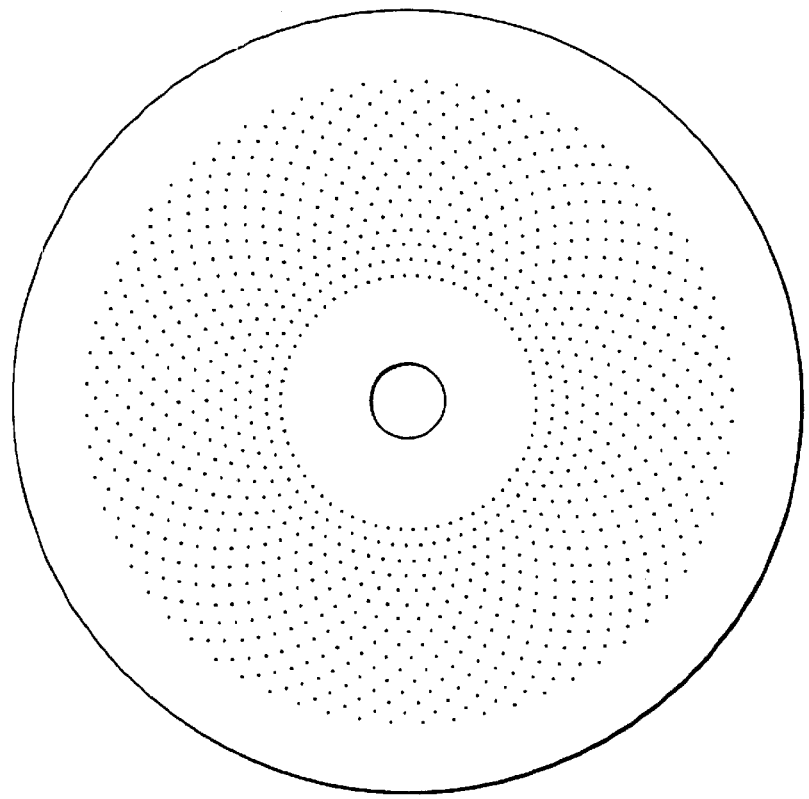
Figure 12:
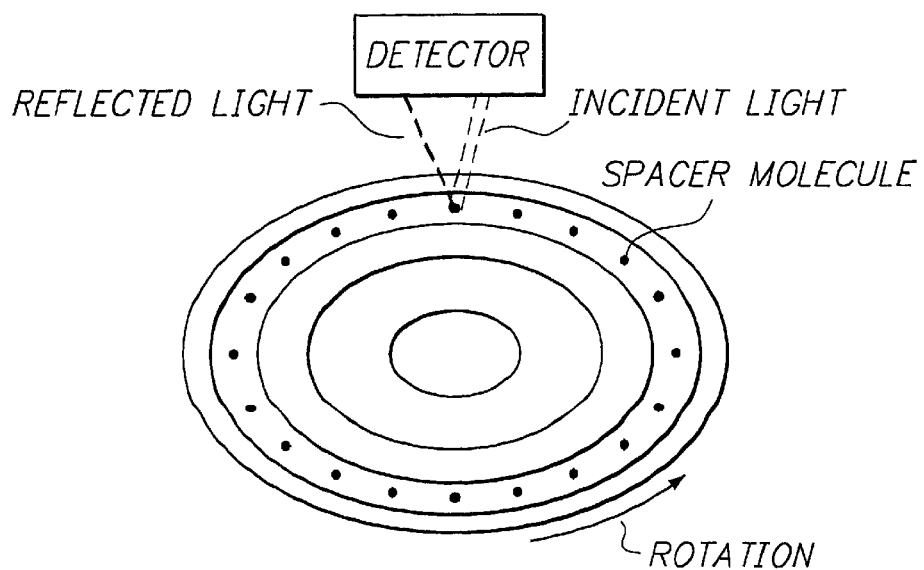
Figure 13A:
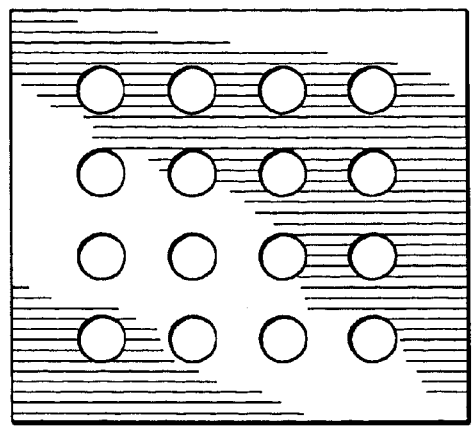
Figure 13C:
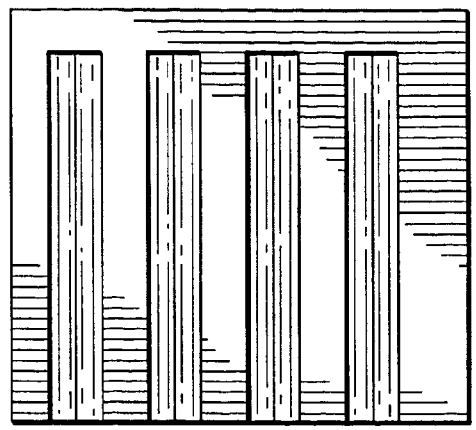
Figure 13B:
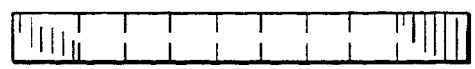
Figure 13D:
Figure 13E:
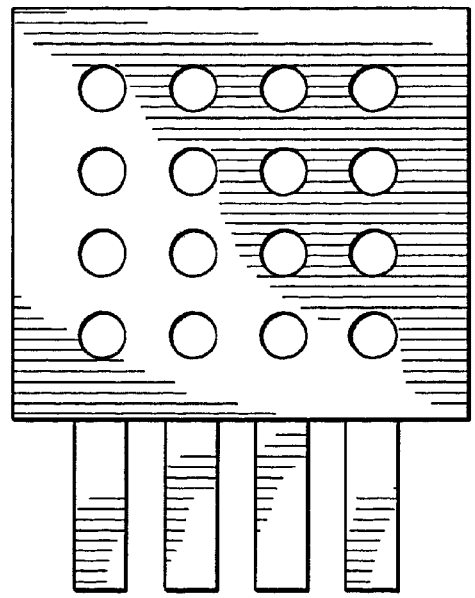
Figure 13F:
Figure 14A:
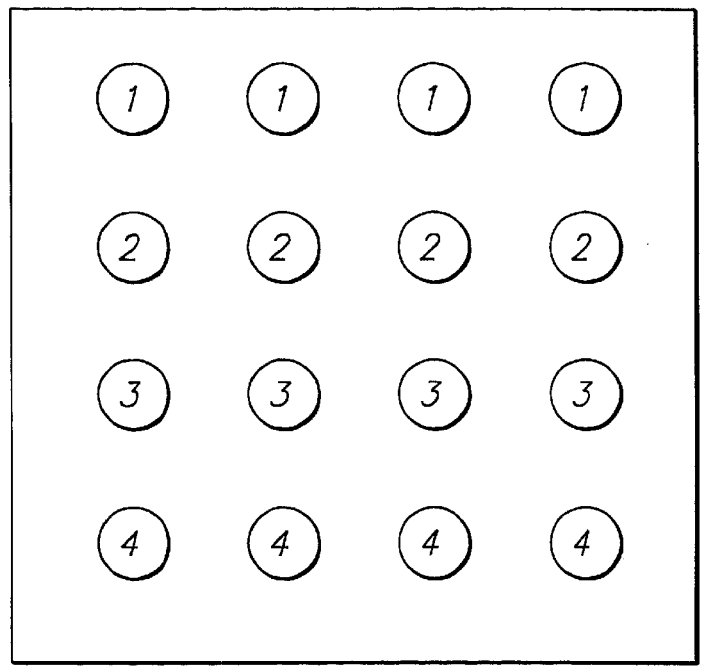
Figure 15A:
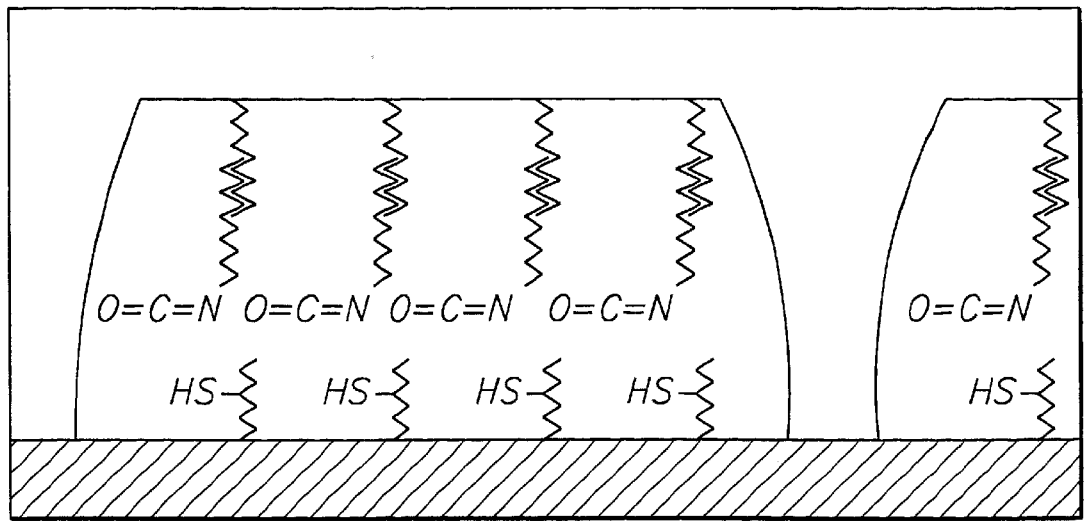
Figure 16:
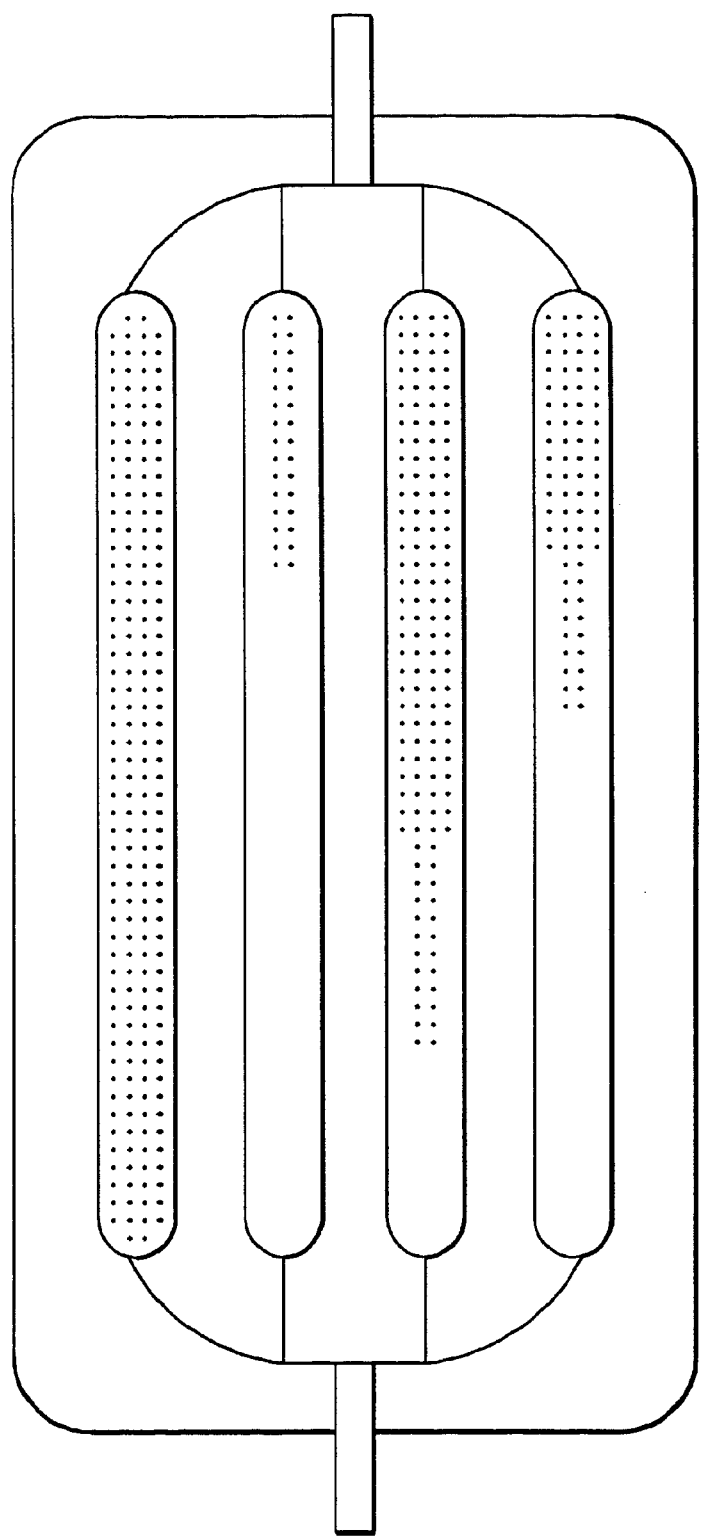
Figure 17A:
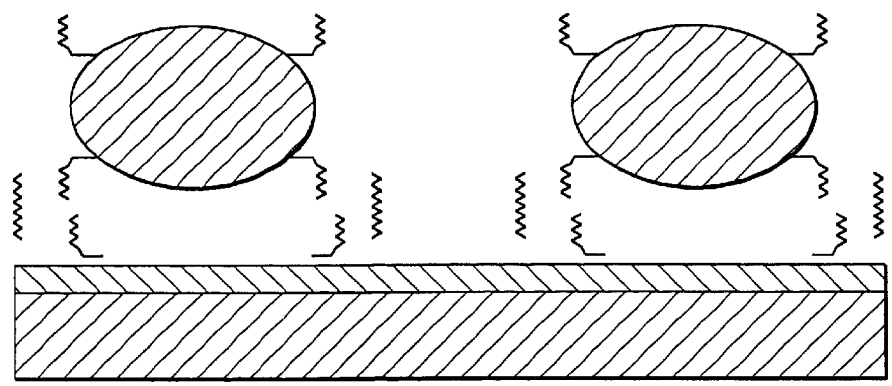
Figure 17B:
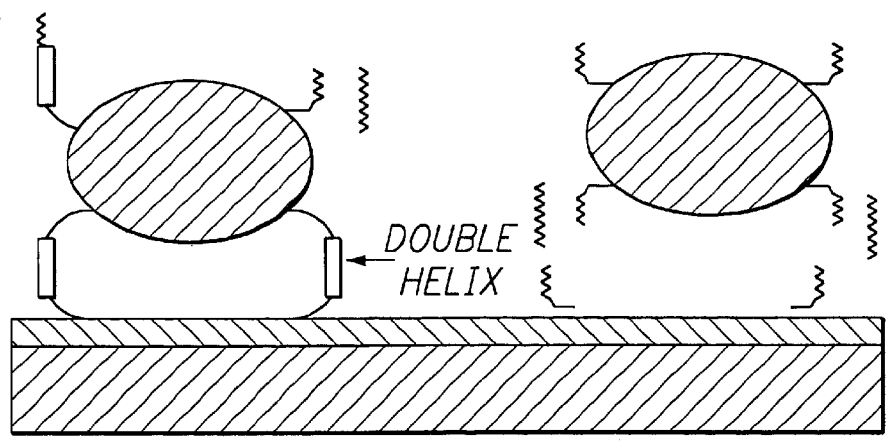
Figure 17C:
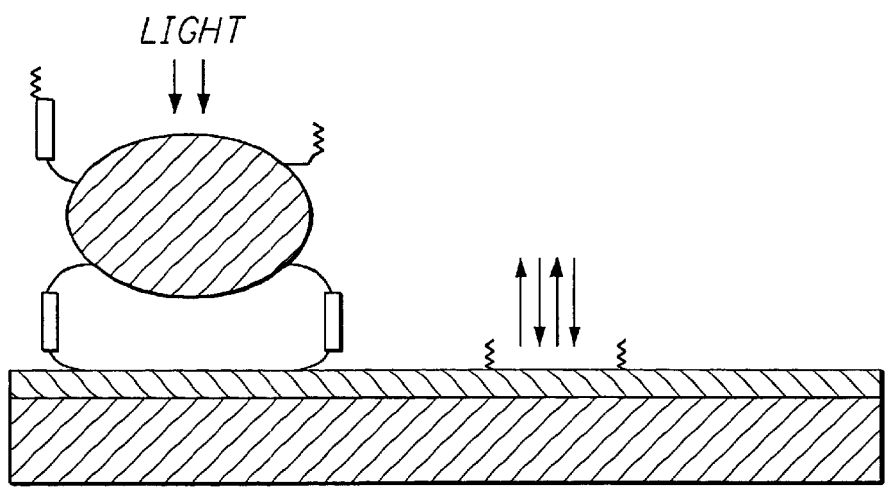
Figure 18A:
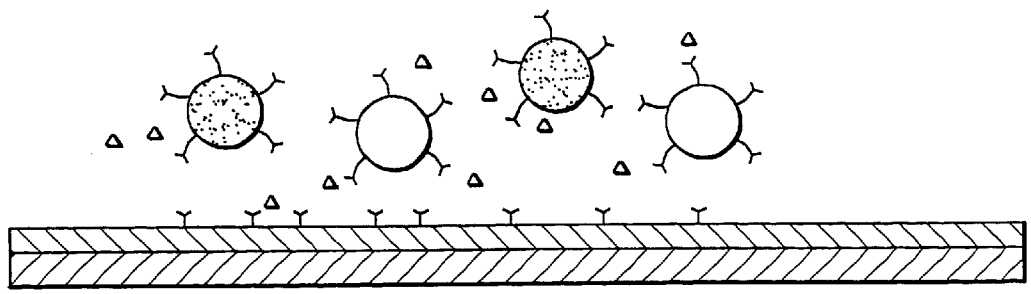
Figure 18B:
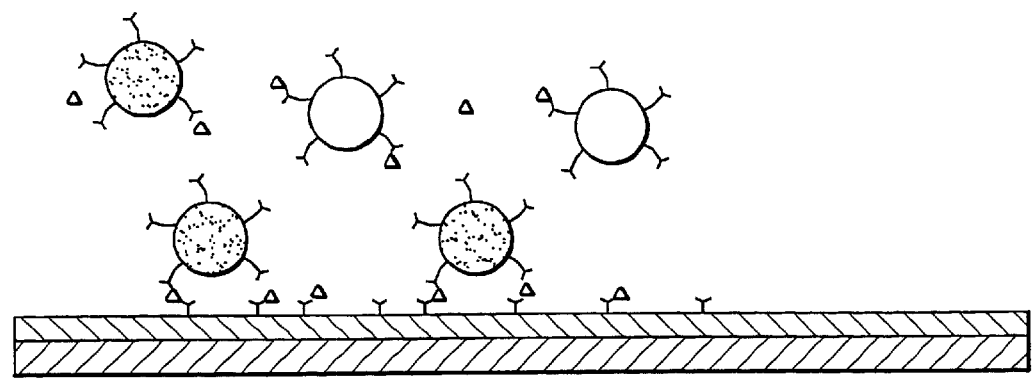
Figure 18C:
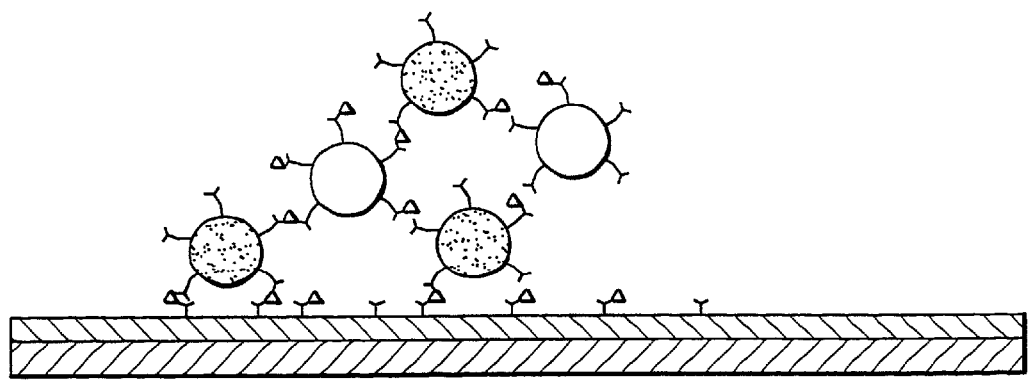
Figure 19:
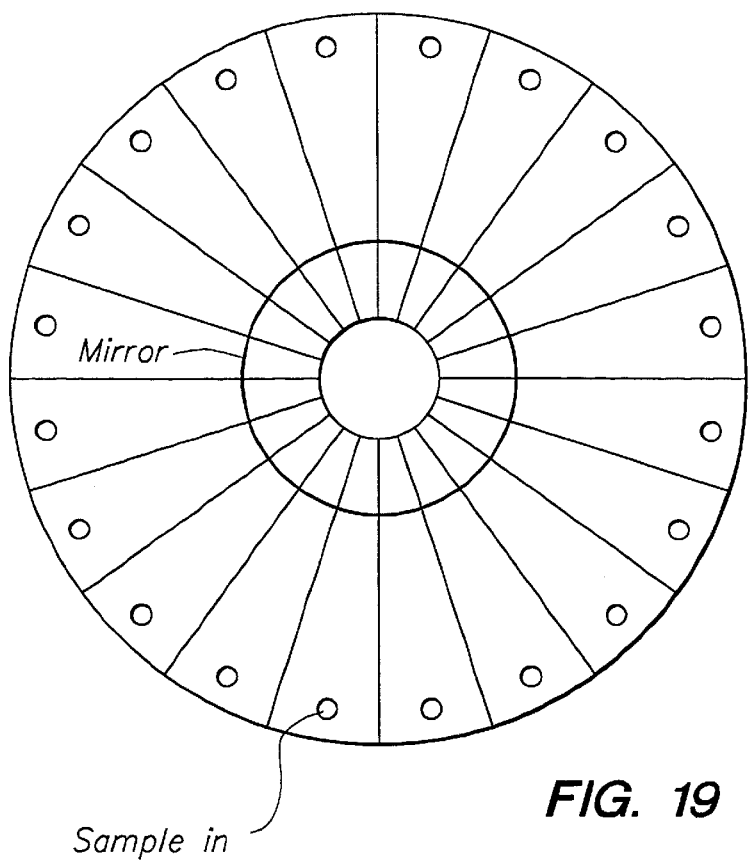
Figure 20A:
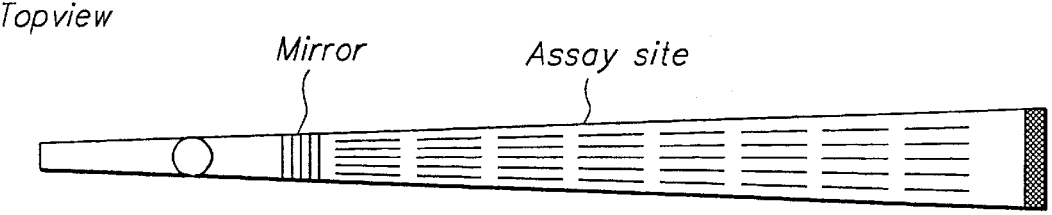
Figure 20B:
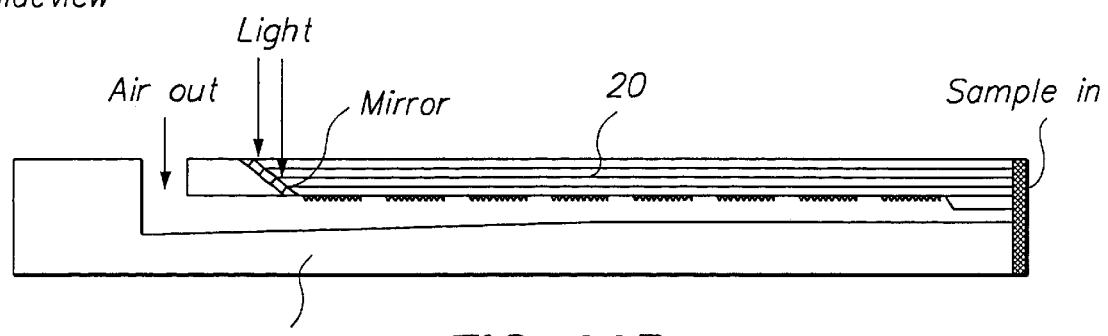
Figure 21A:
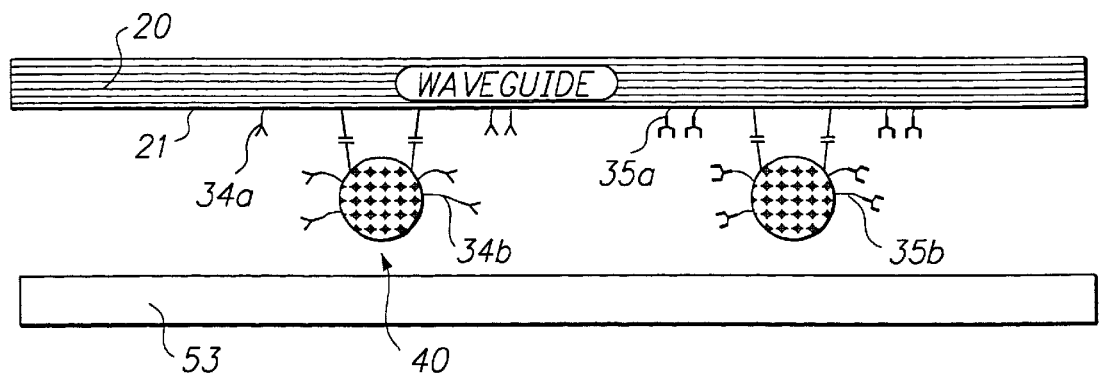
Figure 21B:
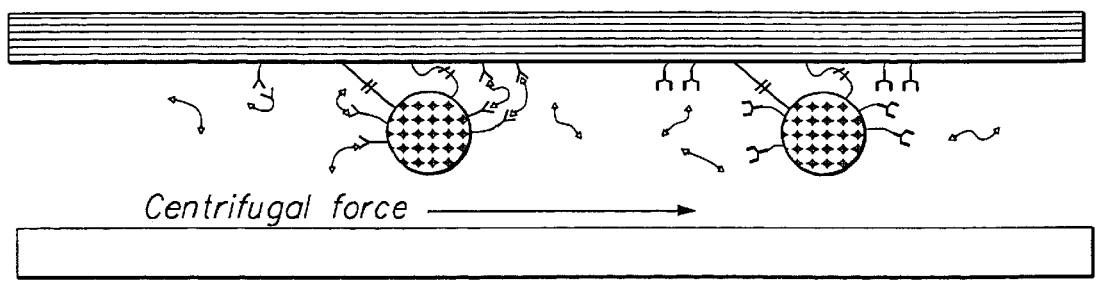
Figure 21C:
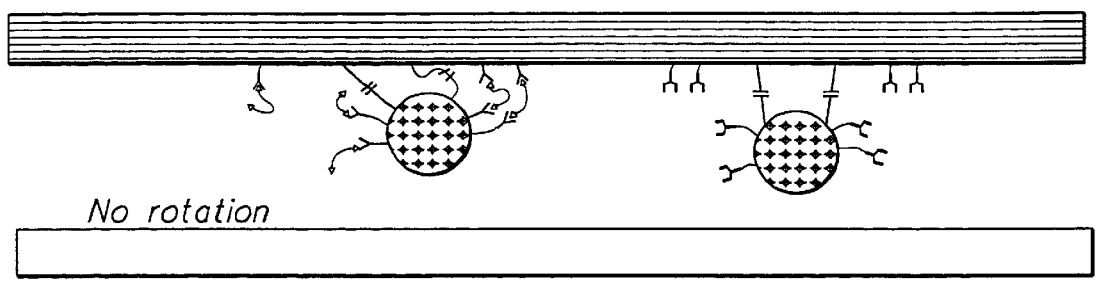
Figure 21D:
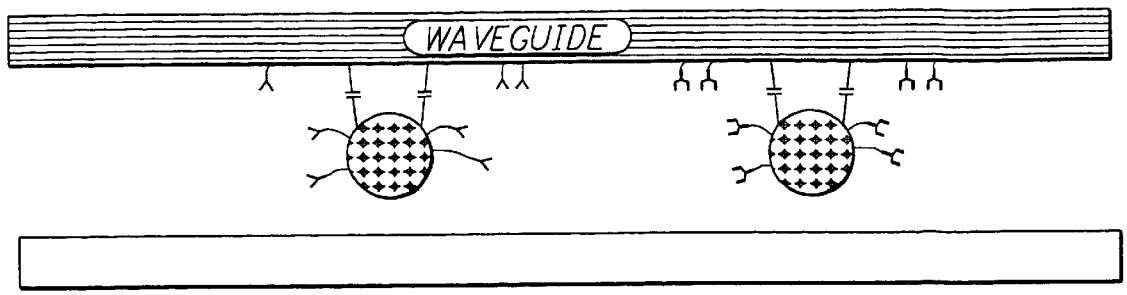
Figure 21E:
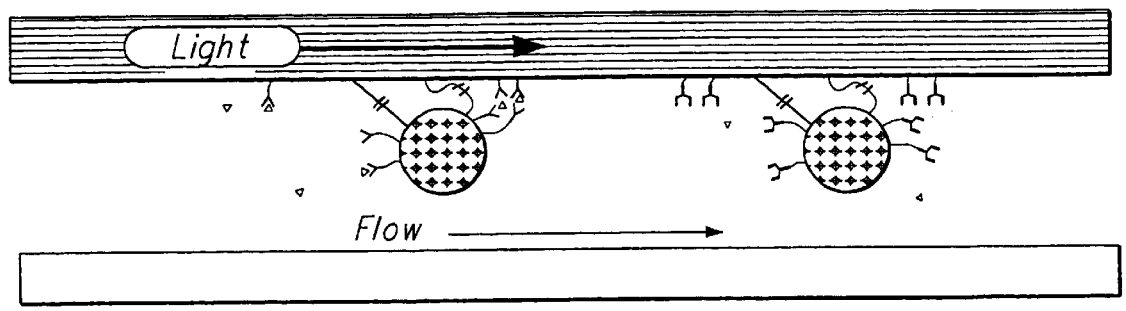
Figure 21F:
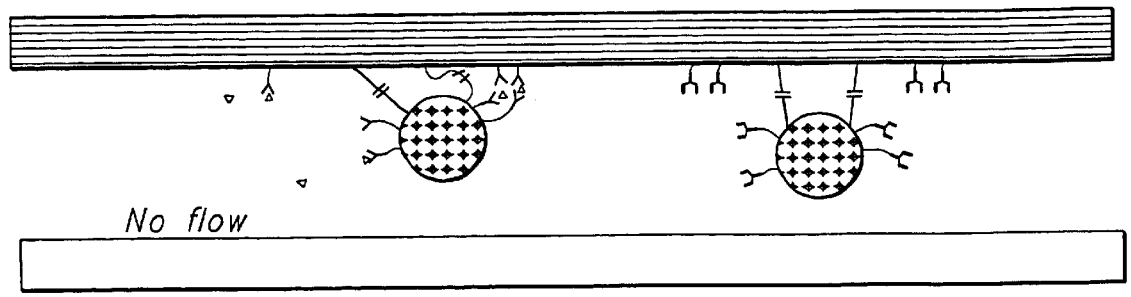
Figure 22A:
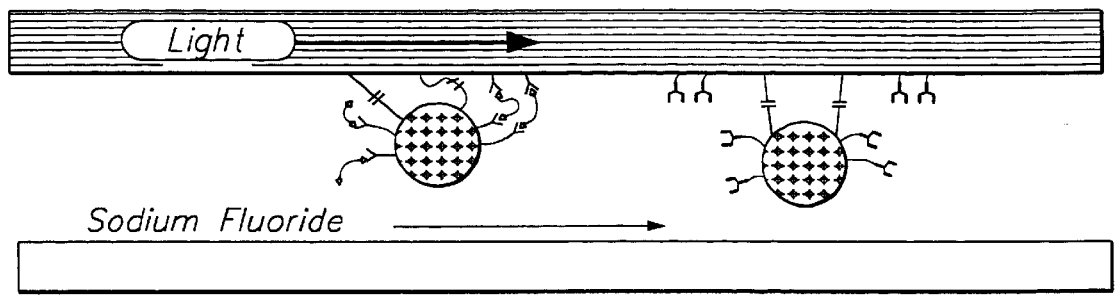
Figure 22B:
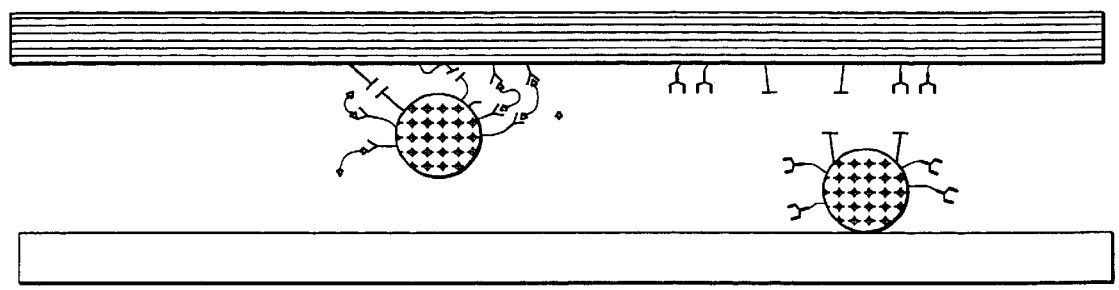
Figure 22C:
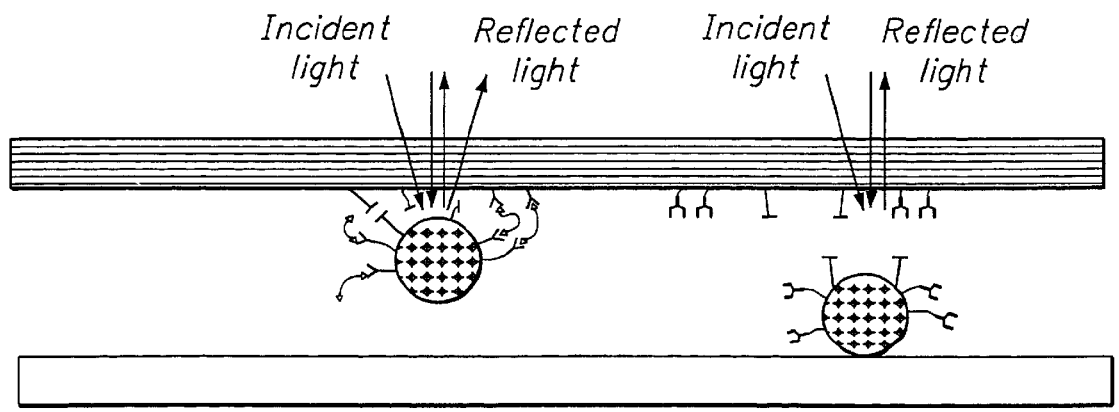
Figure 23A:
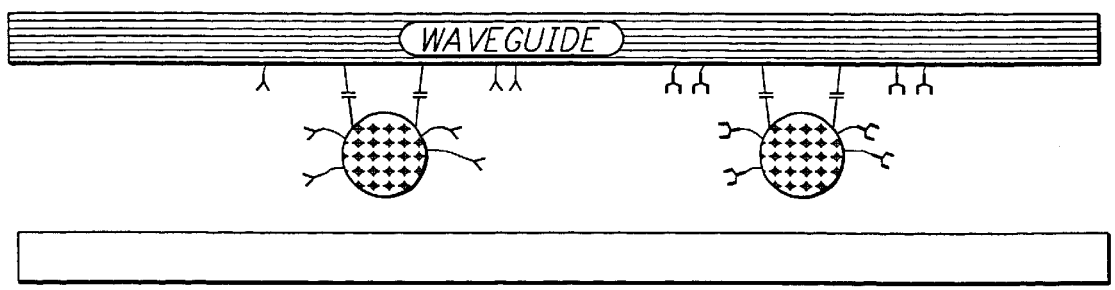
Figure 23B:
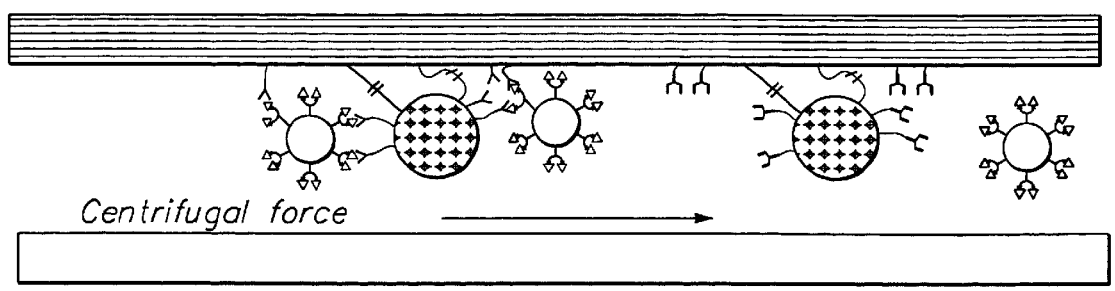
Figure 23C:
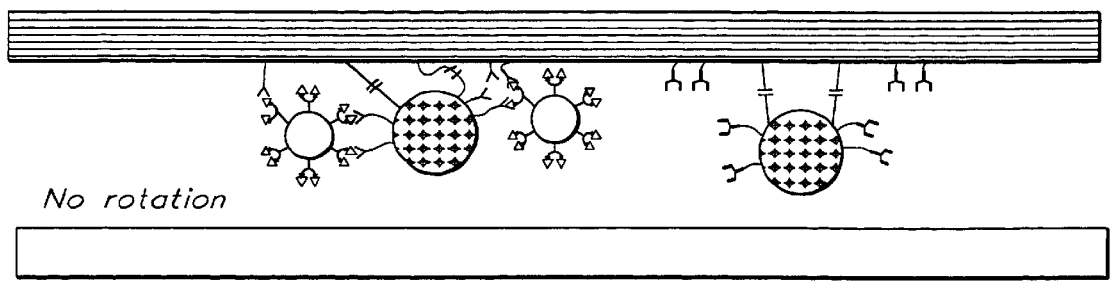
Figure 24:
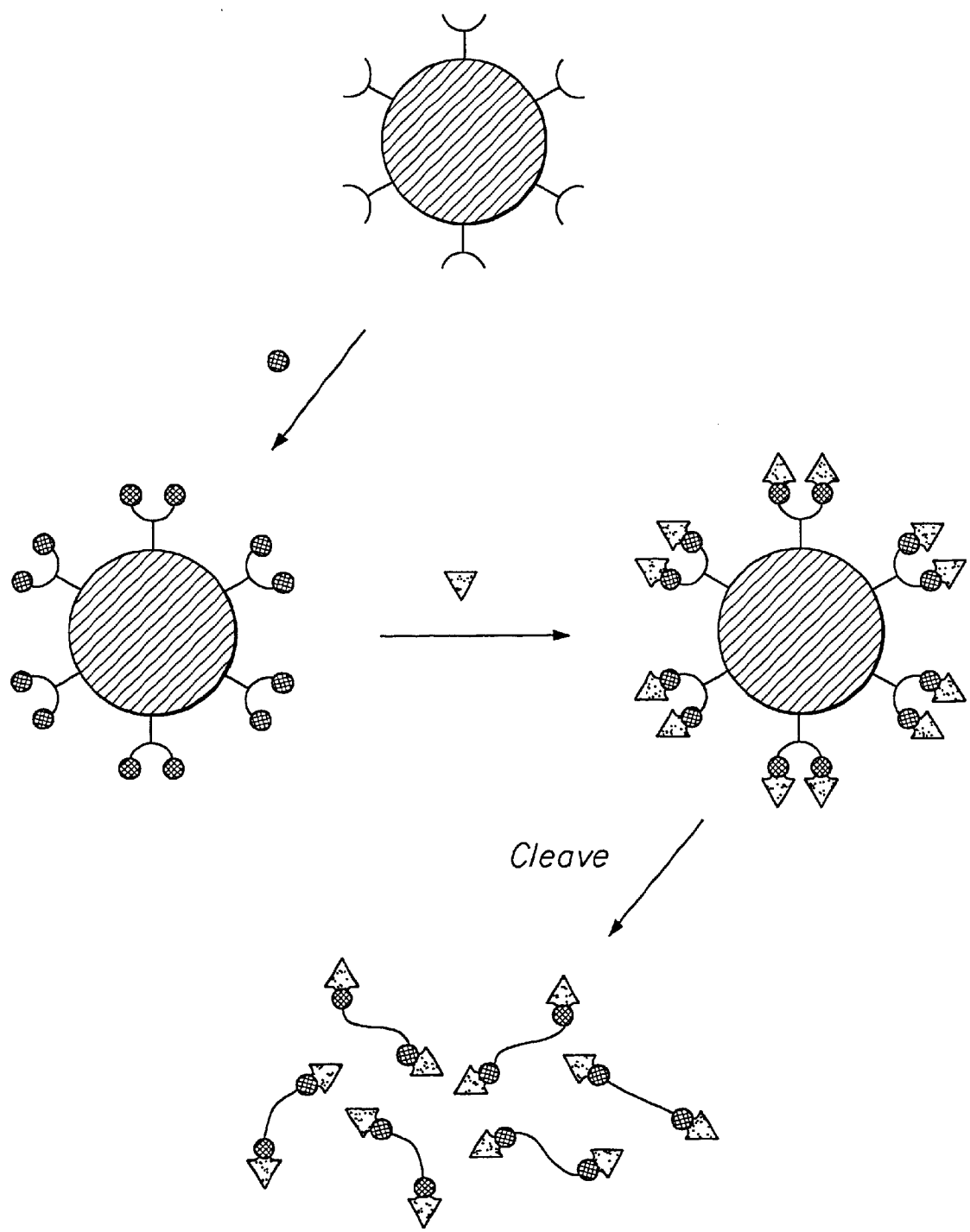
Figure 25:
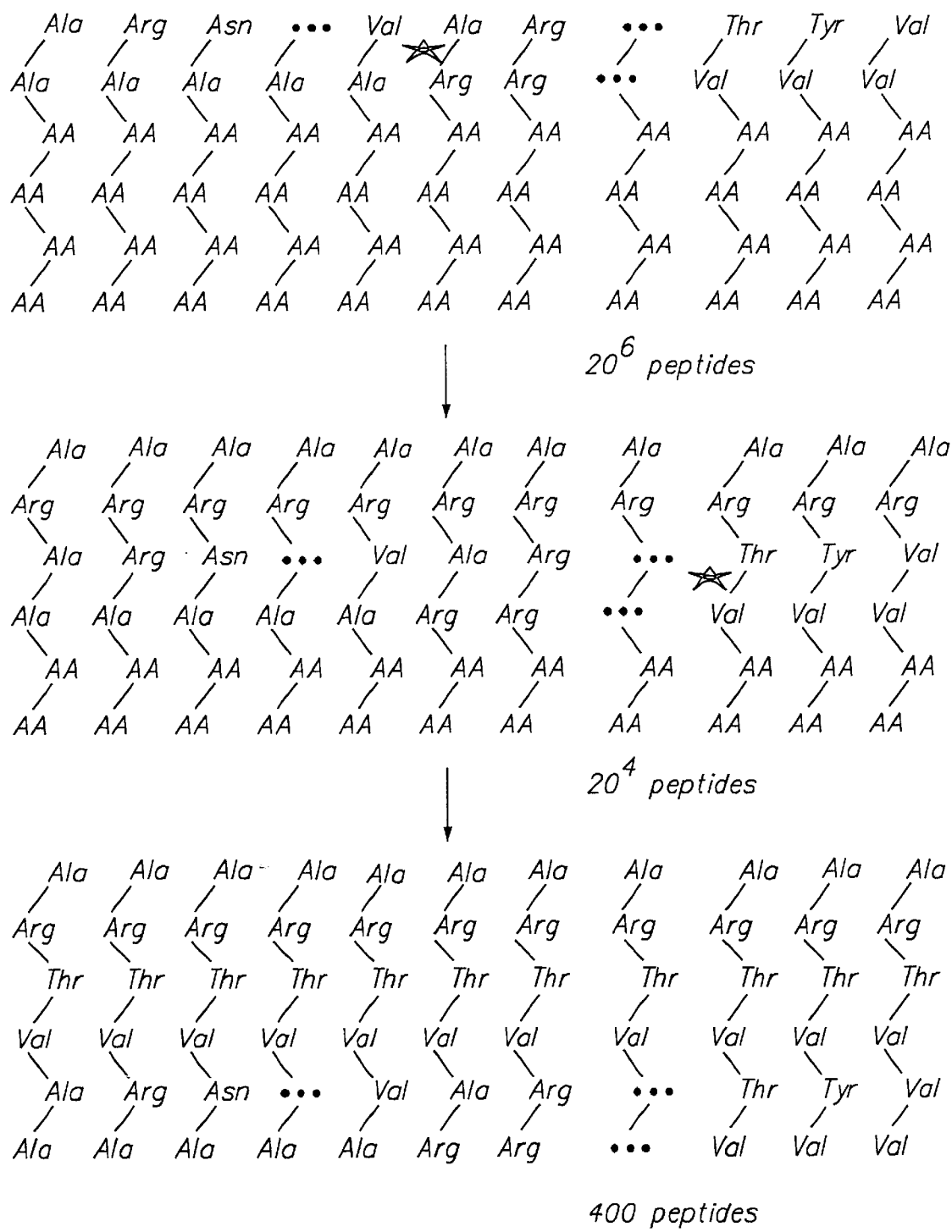
Figure 26:
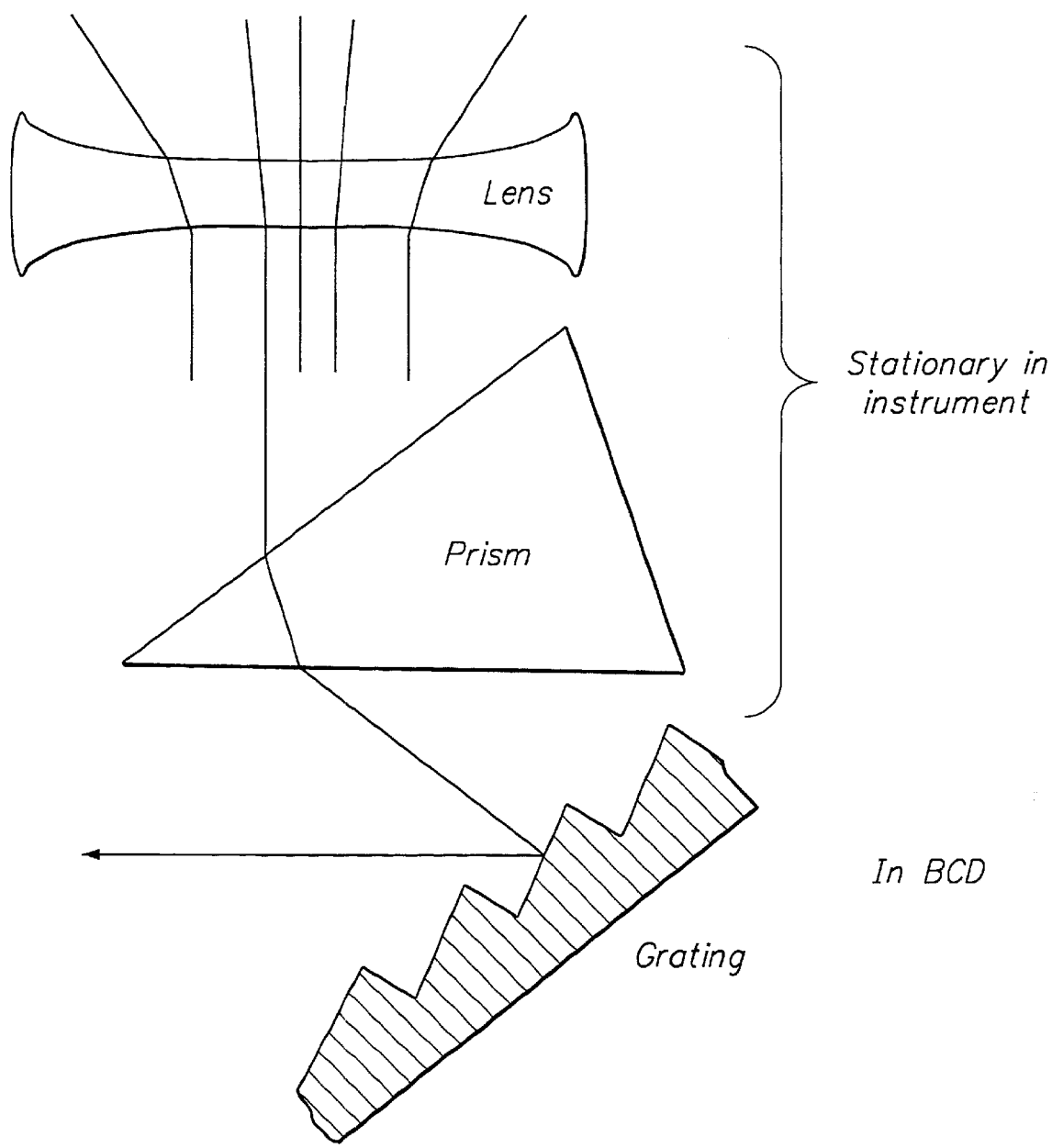
Figure 27A:
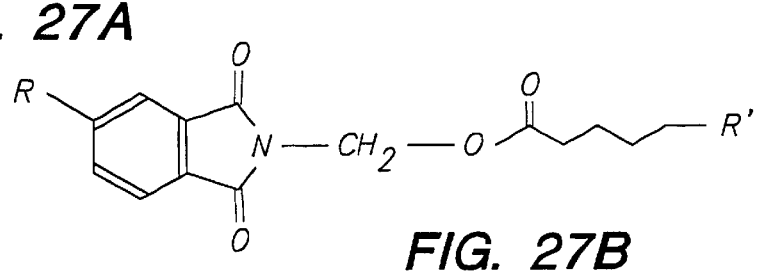
Figure 27B:
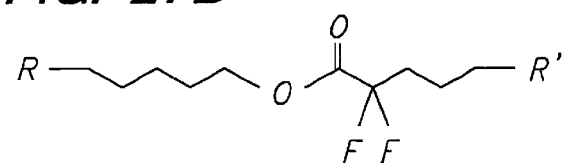
Figure 27C:
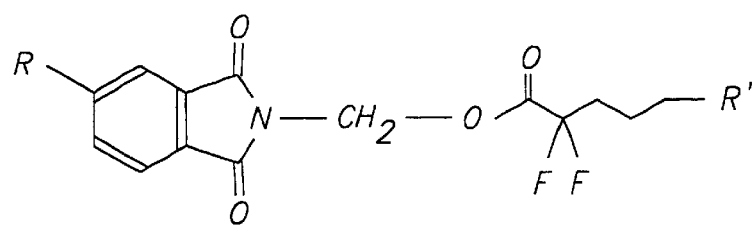
Figure 28A:
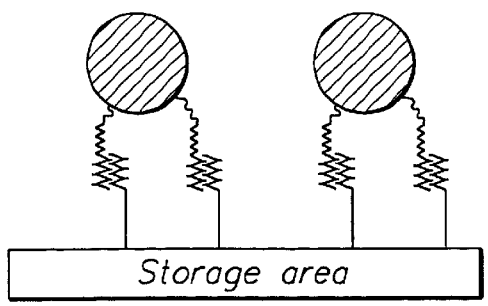
Figure 28B:
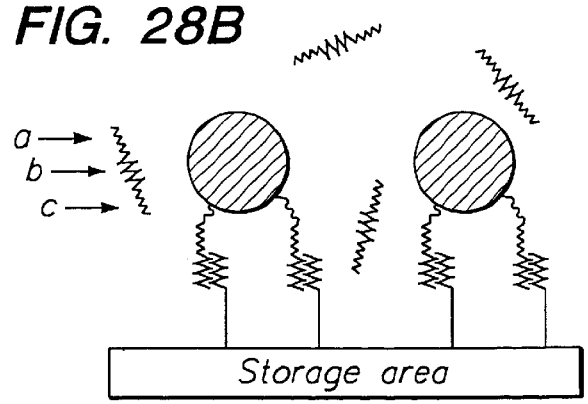
Figure 28C:
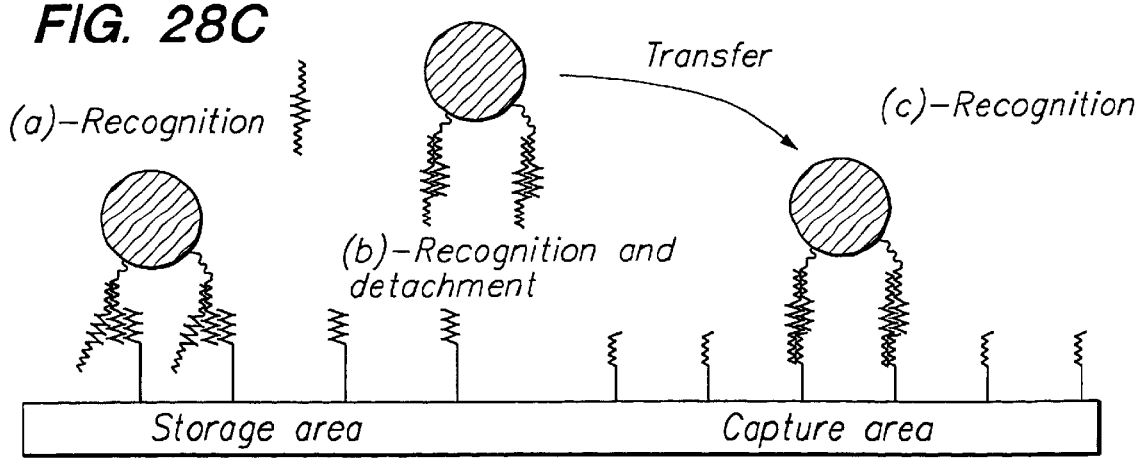

FIG. 2F is a schematic representation, in a nucleic acid detection assay adapted to use the cleavable reflective signal elements of the present invention, of the use of DNA ligase to increase the strength with which analyte-specific binding adheres the signal responsive end of the cleavable spacer to the derivatized substrate of the assay device, thus permitting increased stringency of wash and increased specificity of the assay;

FIG. 3A schematically represents an immunoassay adapted to use the cleavable reflective signal element of the present invention. FIG. 3A illustrates antibodies, adapted to bind to an epitopic site of an antigen suspected to be in a test sample, attached to the side members of the cleavable spacers of a plurality of signal elements;

FIG. 3B is a schematic representation of a later stage in the assay process represented in FIG. 3A and illustrates binding of antigen from the sample to two antibodies of one cleavable signal element, but failure of antigen from the sample to bind to a second set of antibody side members attached to a second cleavable signal element;

FIG. 3C is a schematic representation of the assay of FIGS. 3A and 3B at a still later stage in the assay process, following cleaving of the signal element spacers. The reflective gold microsphere that is not tethered by the specific bridging association of antigen from the sample to signal element antibodies is removed from the surface of the assay device, providing a spatially-addressable, differentially reflective signal;

FIGS. 4A through 4G illustrate schematically the preparation of the solid support substrate upon which cleavable reflective signal elements are deposited in predetermined patterns to create the spatially addressable assay device of this invention;

FIG. 5 is a schematic representation of the chemical structure of an exemplary cleavable spacer molecule of the cleavable reflective signal element of this invention, subsequent to its attachment to the derivatized plastic substrate surface of the assay device but prior to derivatization with oligonucleotide side members, in which piv denotes a pivaloyl protective group, MMT denotes monomethoxytrityl, and n and m each independently represents an integer greater than or equal to one;

FIG. 6 is a further schematic representation of a cleavable spacer molecule, particularly illustrating the site on the spacer molecule that is susceptible to cleaving, and further indicating the sites for attachment of side members, shown protected by Piv and MMT groups;

FIGS. 7A through 7C illustrate in schematic a means for attaching the cleavable spacer molecules to the activated surface of the assay device substrate. In the example illustrated, the aminated surface of the substrate shown in FIG. 7A is converted to active esters as shown in FIG. 7B. The cleavable spacer molecules are attached via the activated esters to the solid support as shown in FIG. 7C;

FIGS. 8A and 8B illustrate intermediate steps during the attachment of a first oligonucleotide side member on the surface-attaching side of the cleavage site of a plurality of cleavable spacer molecules;

FIGS. 9A and 9B are schematic representations illustrating the intermediate steps in the attachment of a second oligonucleotide member on the signal responsive side of the cleavage site of a plurality of cleavable spacer molecules;

FIG. 10A is a schematic representation illustrating the substantially complete cleavable spacer molecule of the cleavable reflective signal element of the present invention, as attached to the solid substrate of the assay device, and prior to the attachment of the microspheres to the signal-responsive end of the cleavable spacer molecules;

FIG. 10B illustrates the attachment of a single reflective particle to the signal responsive end of the cleavable spacers of FIG. 10A, completing the cleavable reflective signal element of the present invention;

FIGS. 11A through 11G illustrate various patterns of spatially addressable deposition of cleavable reflective signal elements on circular, planar disk substrates, in which:

FIG. 11A particularly identifies an address line, encodable on the disk substrate, from which the location of the cleavable spacers may be measured. In FIG. 11A, the cleavable spacer molecules are deposited in annular tracks;

FIG. 11B demonstrates spiral deposition of cleavable signal elements, and particularly identifies a central void of the disk annulus particularly adapted to engage rotational drive means;

FIG. 11C demonstrates deposition of cleavable signal elements in a pattern suitable for assay of multiple samples in parallel, with concurrent encoding of interpretive software on central tracks;

FIG. 11D schematically represents an embodiment in which the assay device substrate has further been microfabricated to segregate the individual assay sectors, thereby permitting rotation of the assay device during sample addition without sample mixing;

FIG. 11E schematically represents an embodiment in which the assay device substrate has further been microfabricated to compel unidirectional sample flow during rotation of the assay device;

FIG. 11F demonstrates deposition of cleavable signal elements in a spatial organization suitable for assaying 20 samples for 50 different analytes each;

FIG. 11G demonstrates the orthogonally intersecting pattern created by superimposition of spiral patterns with spiral arms of opposite direction or chirality;

FIG. 12 is a schematic representation of detection of analyte-specific signals generated by the assay device of FIG. 11A;

FIGS. 13A–F are a schematic example of a stamp for use in printing oligonucleotide side members onto cleavable spacers previously attached to a solid substrate. The stamp as shown is made of two pieces, a stamp piece and a feeding piece. The stamp piece contains holes, which are filled by the required chemicals through a feeding piece containing channels. The channels in turn are connected to a glass capillary array. In this arrangement, one row of holes is filled with the same chemical Different hole and channel patterns can be used as needed;

FIGS. 14A and B are a schematic representation of the pattern of oligonucleotide side member deposition resulting from a two-stage orthogonal printing using the stamp depicted in FIGS. 13A–F. Numbers 1, 2, 3 and 4 represent different phosphoramidite sequences used in the synthesis. In oligonucleotide synthesis using trimers, for example, number 1 can be AAA, number 2 AAC, number 3 AAG and number 4 AAT. The first number in each spot gives the oligonucleotides building block that is most proximal to the cleavable spacer backbone; the second number (if any) represents the next building block. Orthogonal printing is particularly advantageous when depositing the cleavable reflective signal elements of the present invention on a substrate shaped as a disk;

FIGS. 15A and B are a schematic representation of a complementary concave printing process for printing large numbers of oligonucleotide side members simultaneously onto cleavable spacers previously attached to a solid substrate. The cleavable spacers are not themselves shown;

FIG. 16 demonstrates one geometry in which a single sample is channeled in parallel into four distinct sectors of the assay device. If either the density of biobits or affinity of the biobits in the four sectors differs, a large dynamic range of concentration may be determined by detecting the position in each sector of the positive cleavable signal element most distal from the sample application site;

FIGS. 17A–C demonstrate an alternative assay device geometry that dispenses with cleavable spacers, in which a first analyte-specific side member is attached directly to the assay device substrate, while a second analyte-specific side member is attached directly to the signal responsive moiety, shown here as a plastic microsphere;

FIGS. 18A–C demonstrate a further alternative geometry dispensing with cleavable spacers, in which a first side member is attached directly to the assay device substrate, a second side member is attached directly to the signal responsive moiety, and analyte causes agglutination of signal responsive moieties;

FIG. 19 shows a top view of an assay device adapted for continuous monitoring, in which a radially disposed mirror directs incident light into the plane of the assay device substrate which functions as an optical waveguide. Also shown are circumferentially disposed sample application inlets for each of 20 independent assay sectors;

FIGS. 20A–B show further detail of the continuous monitoring assay device of FIG. 19, with FIG. 20A showing a top view of a single assay sector and FIG. 20B showing a side view of a single assay sector;

FIGS. 21A–F show side views of an assay site during continuous monitoring for analytes;

FIGS. 22A–C show the assay device of FIG. 21 after sample application, with subsequent cleavage of cleavable spacers for detection using reflectance of incident light;

FIGS. 23A–C show continuous monitoring of solid support particles;

FIG. 24 shows synthesis of dimers;

FIG. 25 shows screening of hexapeptides;

FIG. 26 demonstrates the alternative use of a diffraction grating for directing incident light into the assay device substrate adapted for use as an optical waveguide;

FIGS. 27A–C shows a cleavable ester moiety, the ease of hydrolysis of which is modified by the addition of an n-pthalimidomethyl group on the alcohol side, shown in FIG. 27A, by the addition of an α, α difluoroacid moiety on the carboxylic acid side, shown FIG. 27B, or by addition of both, shown in FIG. 27C;

FIGS. 28A–C show an alternative geometry for nucleic acid hybridization assays that increases the fidelity of sequence detection, useful in assays for defined sequences, as in assays for detection of in vitro amplified nucleic acids, and also useful in nucleic acid sequencing.

FIG. 28A shows signal responsive moieties, shown as spheres, maintained by noncovalent sequence-specific hybridization in a storage area of the assay device.

FIG. 28B shows the presence of a single-stranded nucleic acid analyte, and further identifies three subsequences therein.

Figure 29:
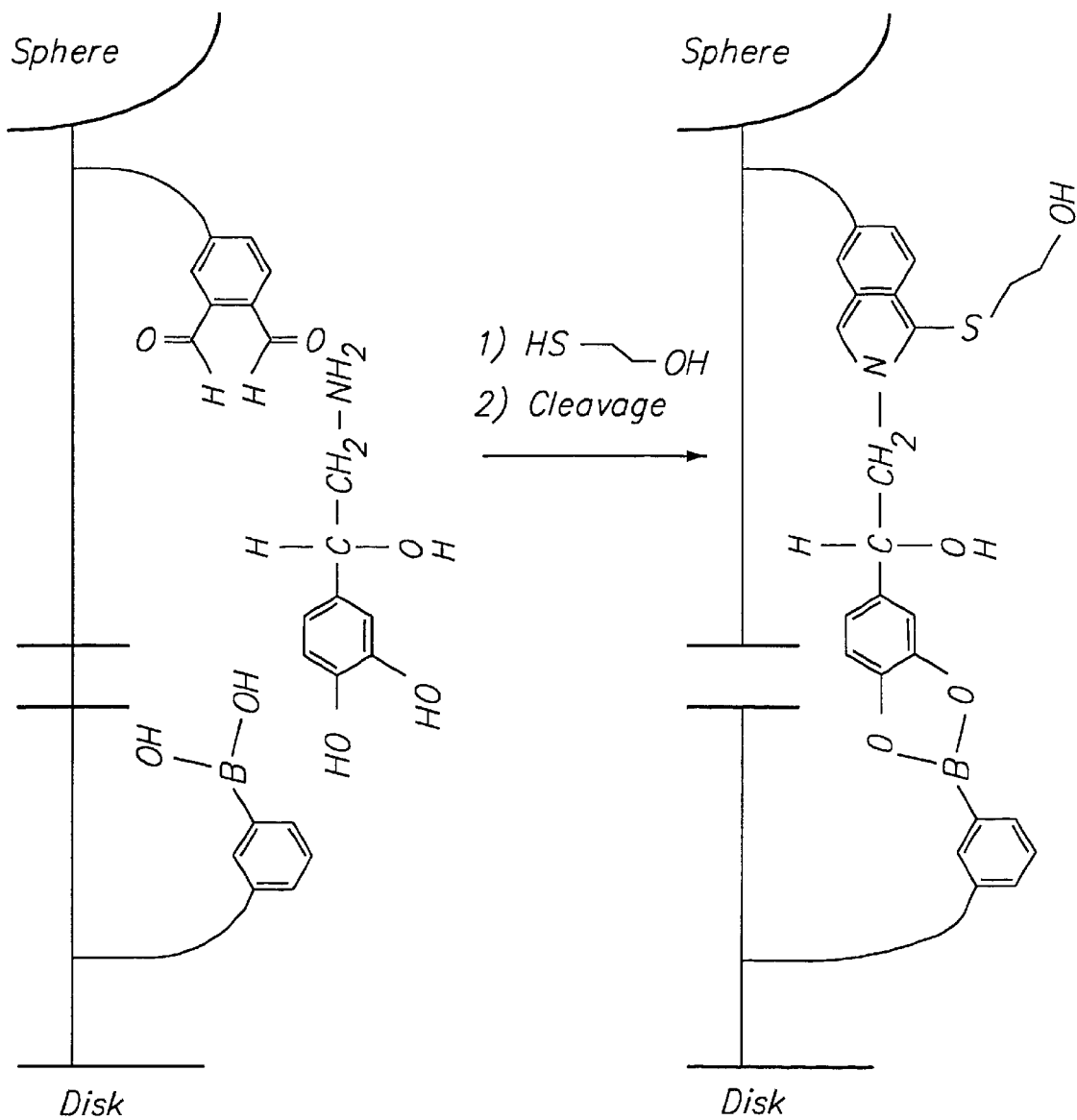
Figure 30:
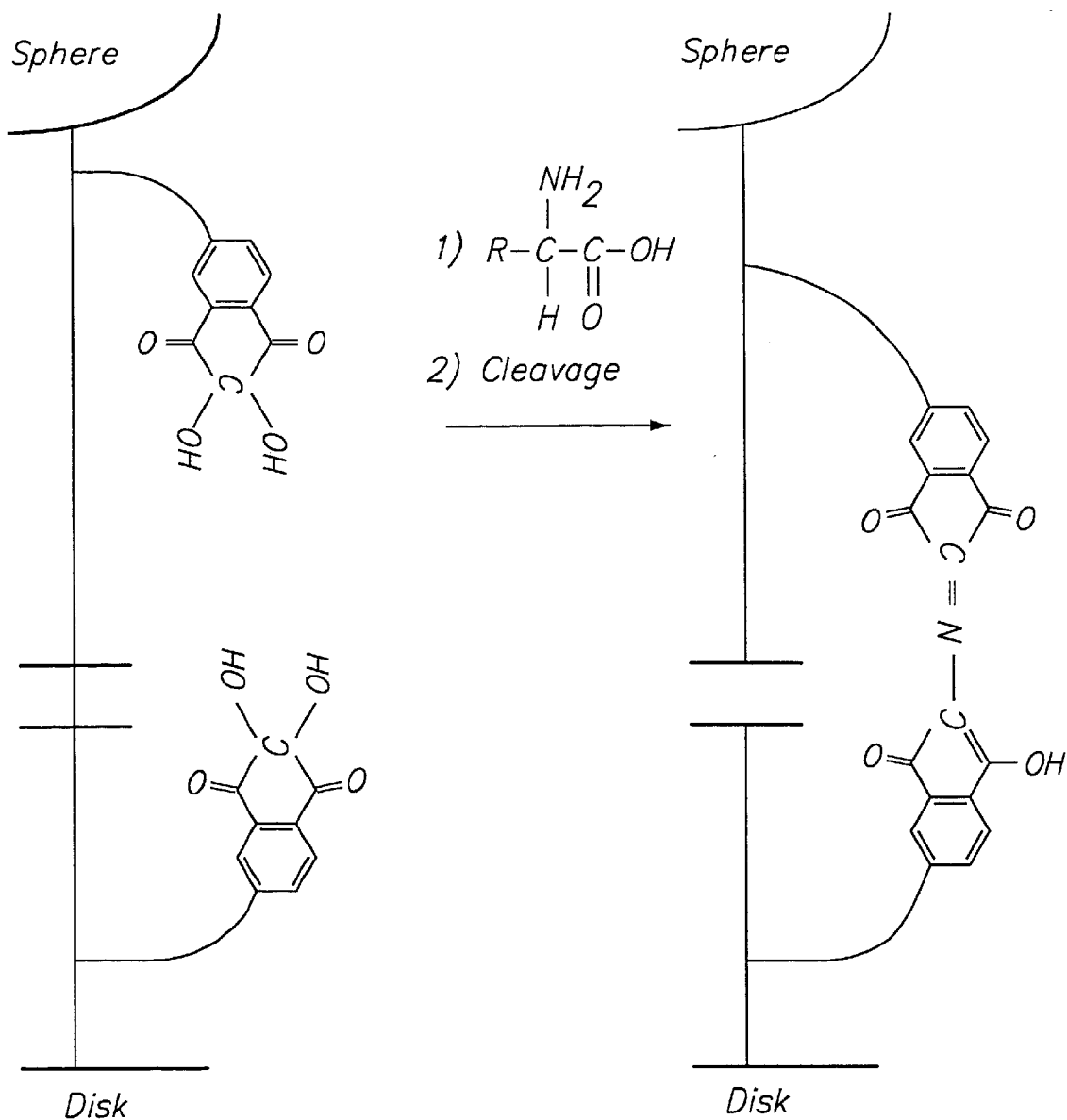
Figure 31A:
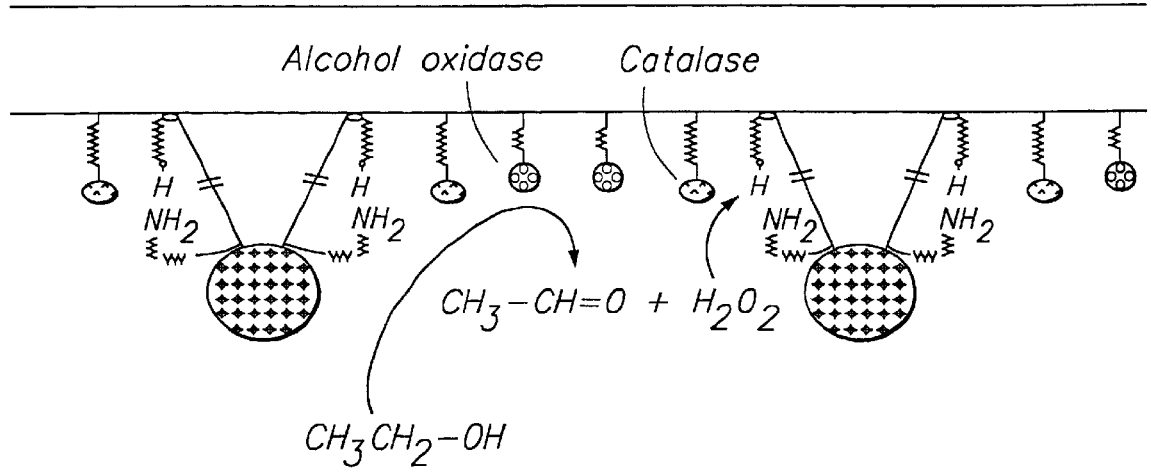
Figure 31B:
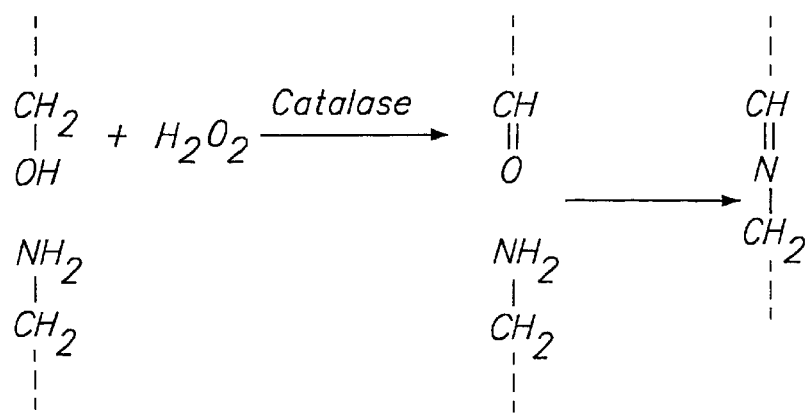
Figure 32A:
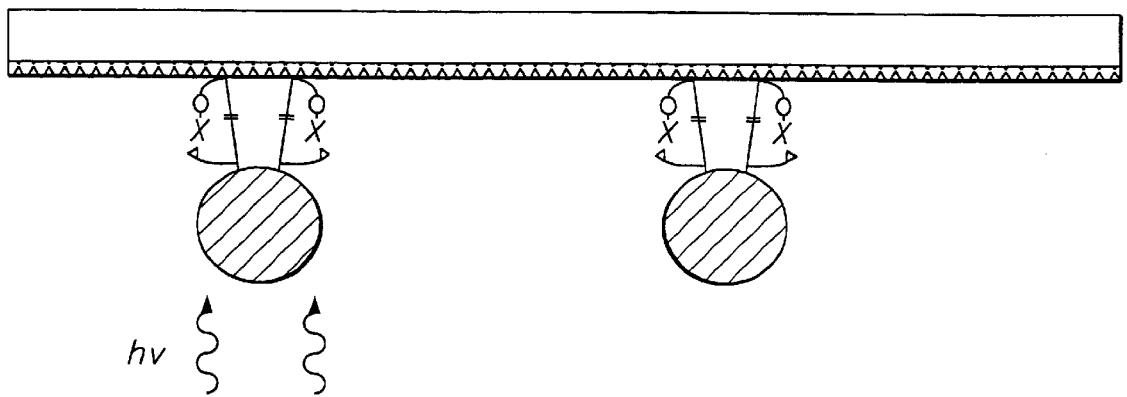
Figure 32B:
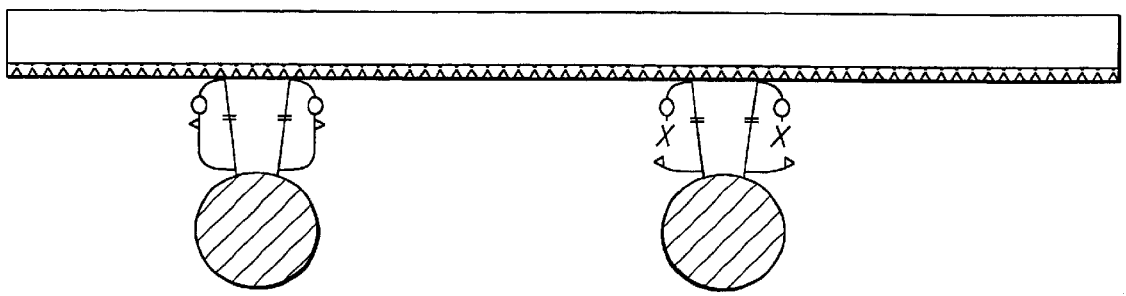
Figure 32C:
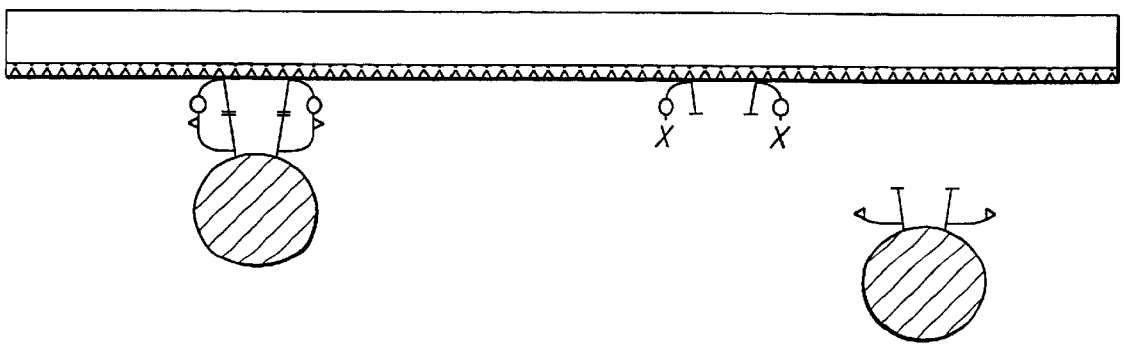
Figure 33A:
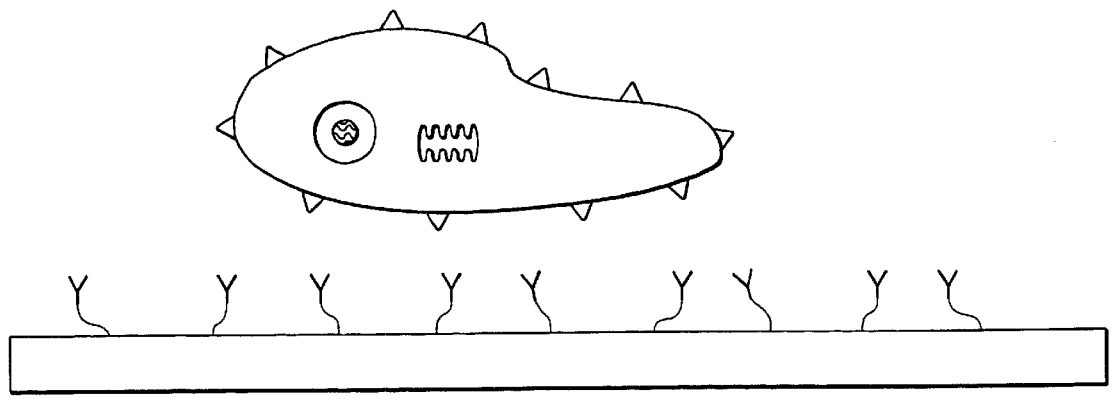
Figure 33B:
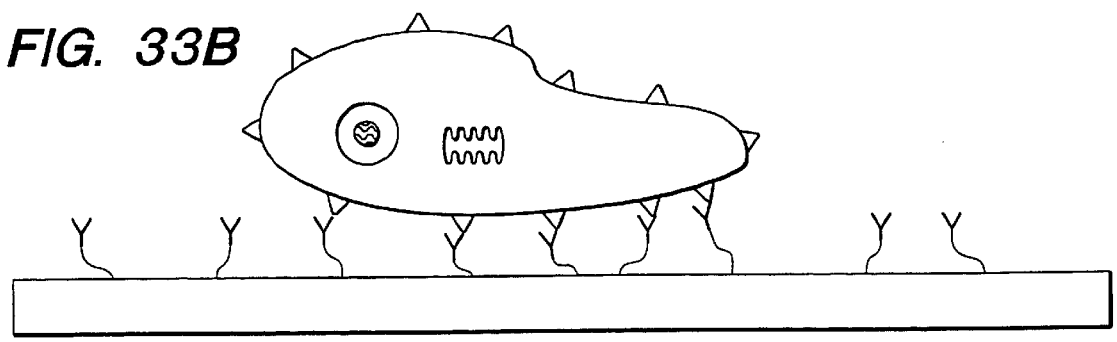
Figure 33C:
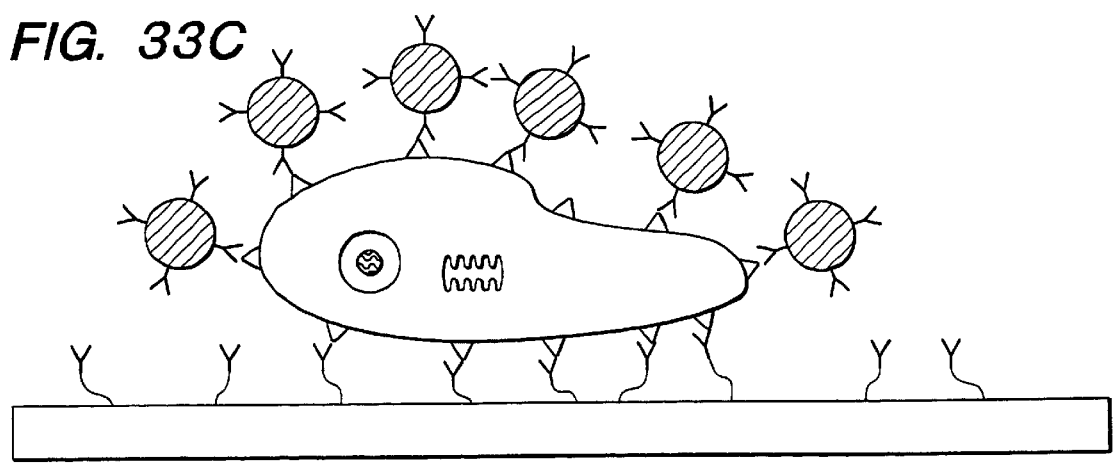

FIG. 28C shows recognition of subsequence "a" of the analyte, causing detachment from the storage area of the signal responsive moiety, transfer of the detached signal-responsive moiety and transfer to a capture area, and recognition and binding of the signal responsive moiety mediated by subsequence "c" of the analyte;

FIG. 29 shows the adaptation of the cleavable spacer invention for detection of a small organic molecule, norepinephrine;

FIG. 30 demonstrates the adaptation of the cleavable spacer invention for detection of amino acids in a sample;

FIGS. 31A–B demonstrate the adaptation of the cleavable spacer invention for detection of ethanol, using alcohol oxidase and catalase;

FIGS. 32A–C show the use of photoactivatable groups on the side members of a cleavable spacer, for detection of incident radiation;

FIGS. 33A–C show an alternative assay geometry for for cell counting and cell shape detection, using an optical disk without cleavable spacers.

FIG. 33A shows a plurality of first cell type-specific recognition elements disposed on the substrate surface of an assay device, shown schematically FIG. 33B shows binding of the cell to the cell type-specific recognition elements.

Figure 34A:
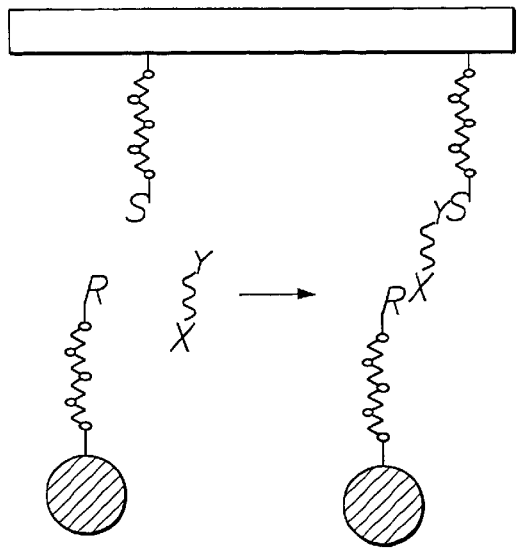
Figure 34B:
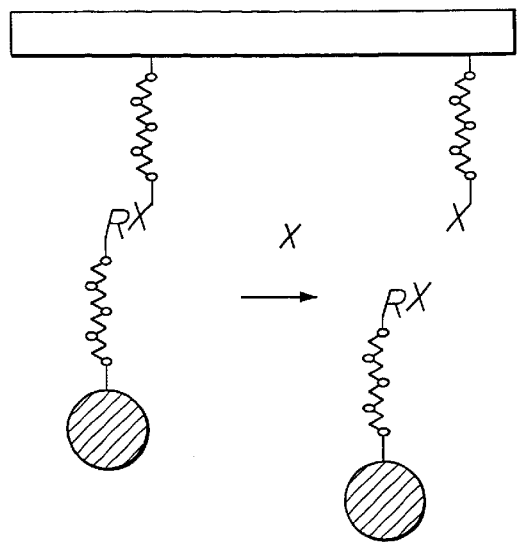
Figure 34C:
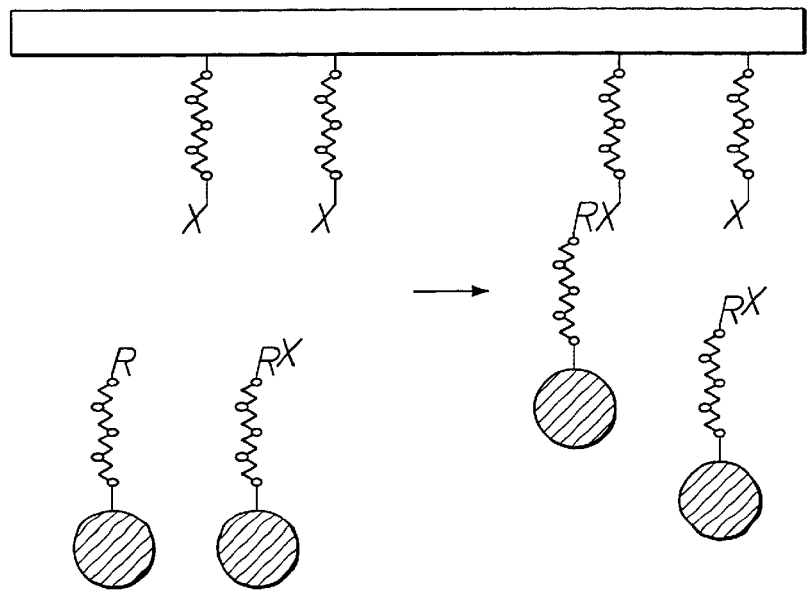

FIG. 33C shows signal responsive moieties, added subsequently, decorating the surface of the cell, rendering it suitable for detection;

FIGS. 34A–C present a classification of assay geometries that may be practiced using the detection methods and assay devices of the present invention, without the need for cleavable spacers.

FIG. 34A shows analyte-mediated binding of signal-responsive moieties in a sandwich assay.

FIG. 34B shows an analyte-mediated displacement of signal responsive moieties, a replacement assay.

Figure 35A:
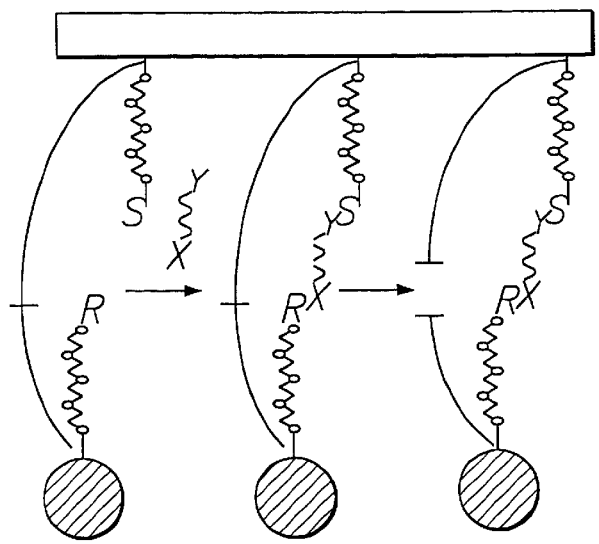
Figure 35B:
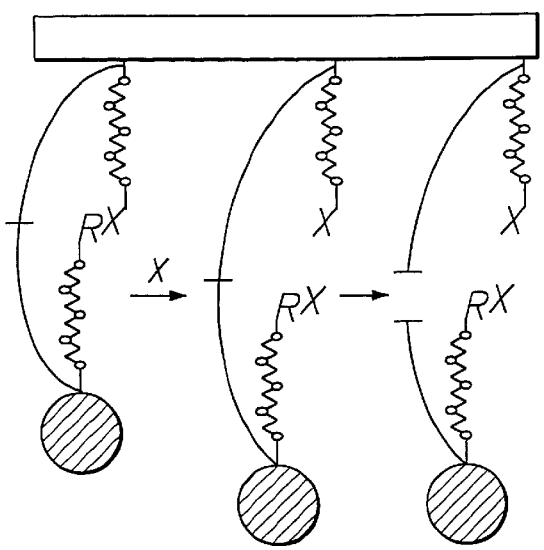
Figure 35C:
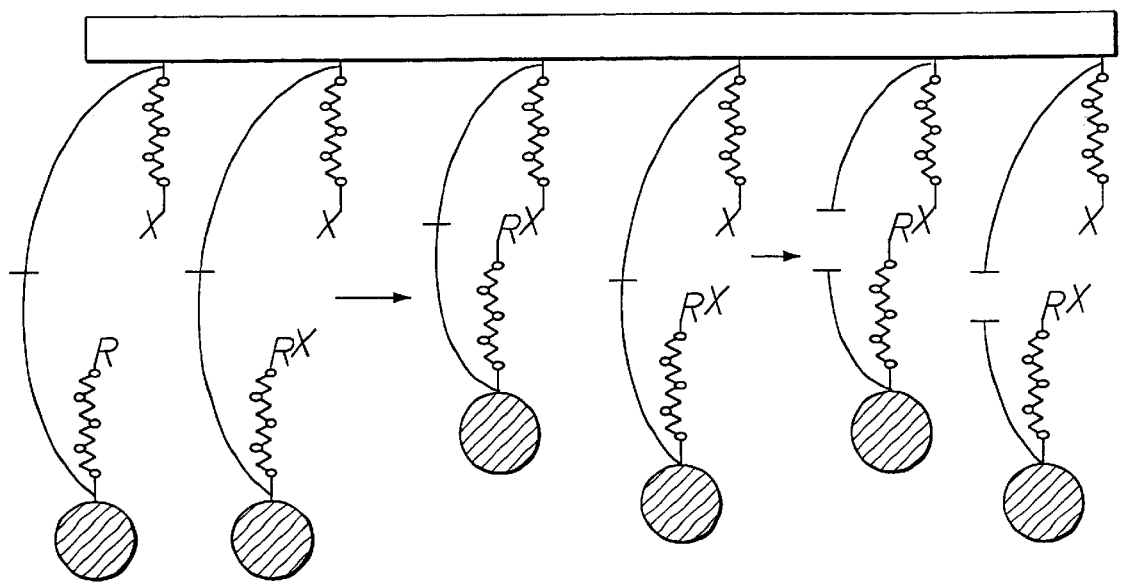

FIG. 34C shows a competitive assay;

FIGS. 35A–C present a classification of assay geometries that may be practiced using the detection methods and assay devices of the present invention, additionally using the cleavable spacers of the present invention.

FIG. 35A shows analyte-mediated binding of first and second side members of a cleavable spacer in a sandwich assay.

FIG. 35B shows an analyte-mediated displacement of connected first and second side members, a replacement assay.

Figure 36:
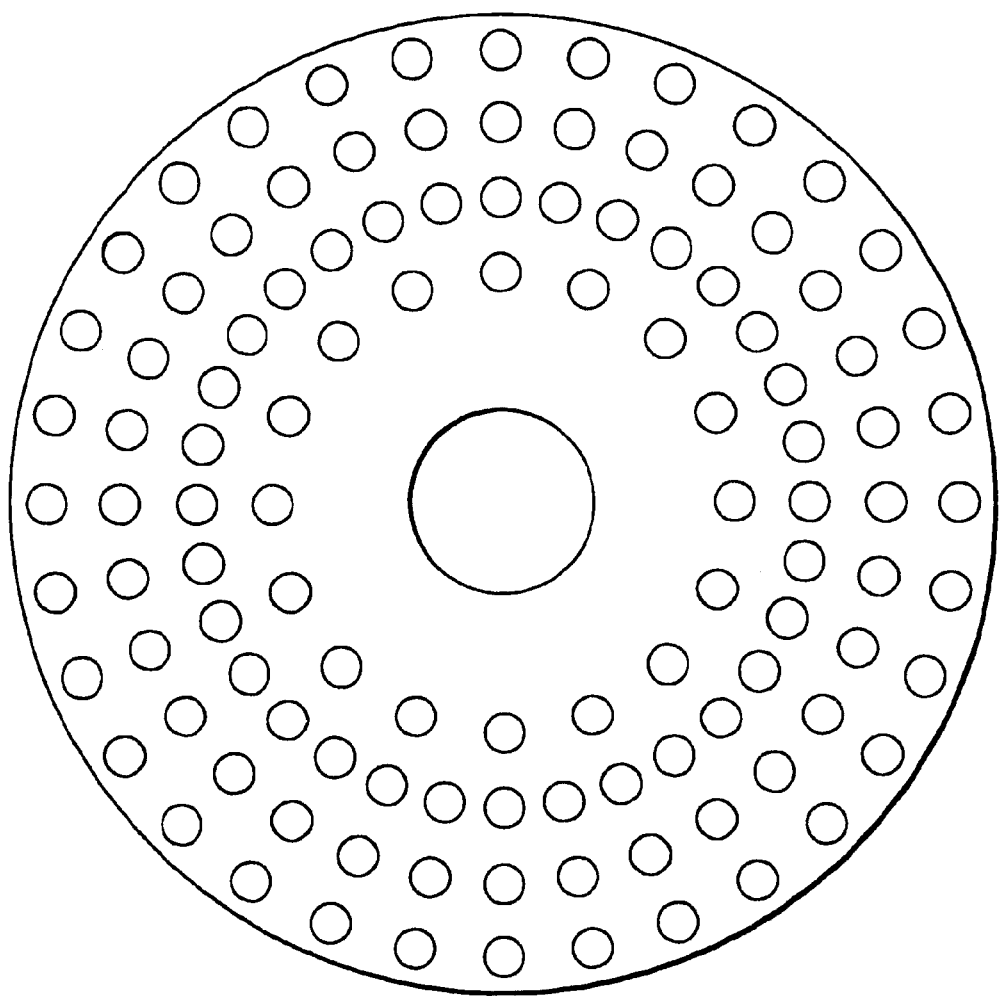
Figure 36:
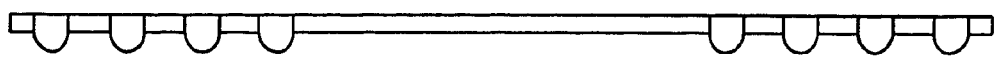

FIG. 35C shows a competitive assay;

FIG. 36 shows a top view and side view of a sample application plate, in which wells suitable for holding liquid samples are disposed in a spatial orientation suitable for applying in parallel a plurality of individual samples to the assay sites of an assay device of the present invention;

FIGS. 37A–F show sample application using the sample application plate of FIG. 36.

Figure 37A:
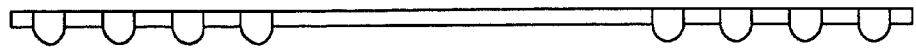

FIG. 37A shows a side view of the sample application plate.

Figure 37B:
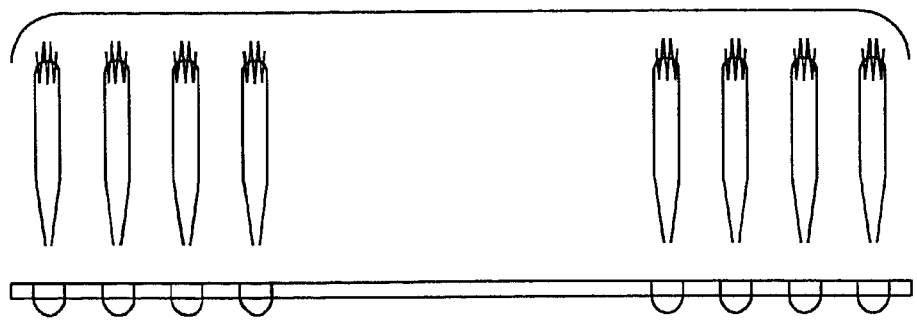

FIG. 37B shows addition of samples to the wells of the sample application plate using a robotic pipetting station with multiple pipettes.

Figure 37C:
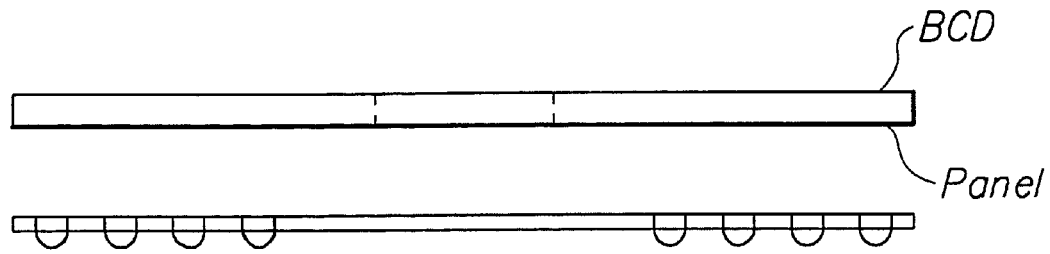

FIG. 37C shows the assay device oriented for sample addition, with assay areas disposed upon the assay device in registration with the wells of the sample application plate.

Figure 37D:
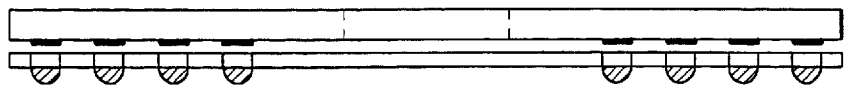

FIG. 37D shows direct approximation of the assay device to the sample application plate.

Figure 37E:
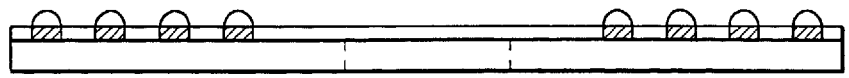

FIG. 37E shows gravity driven application of samples to the assay device through inversion of the approximated sample application plate and assay device.

Figure 37F:
Figure 38:
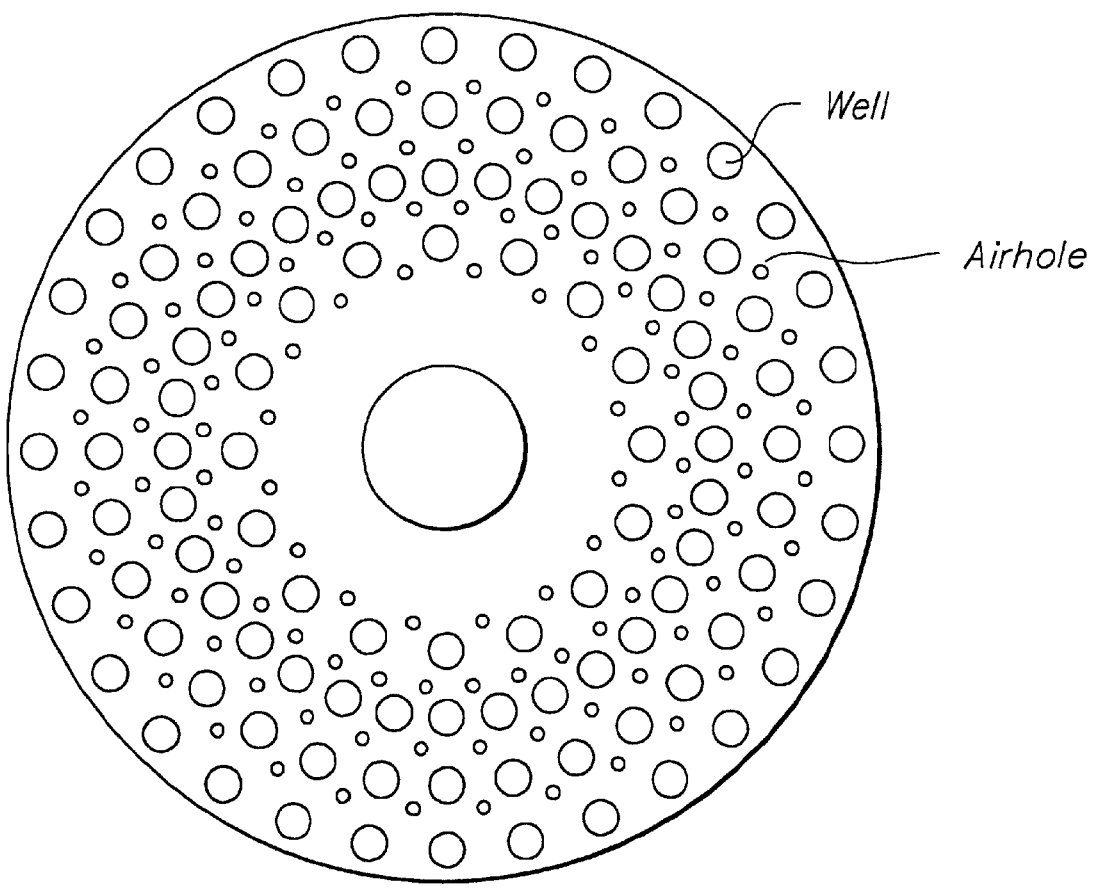
Figure 38:
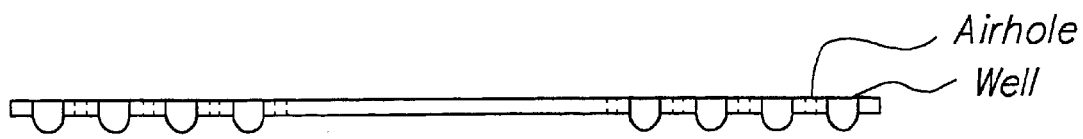
Figure 39:
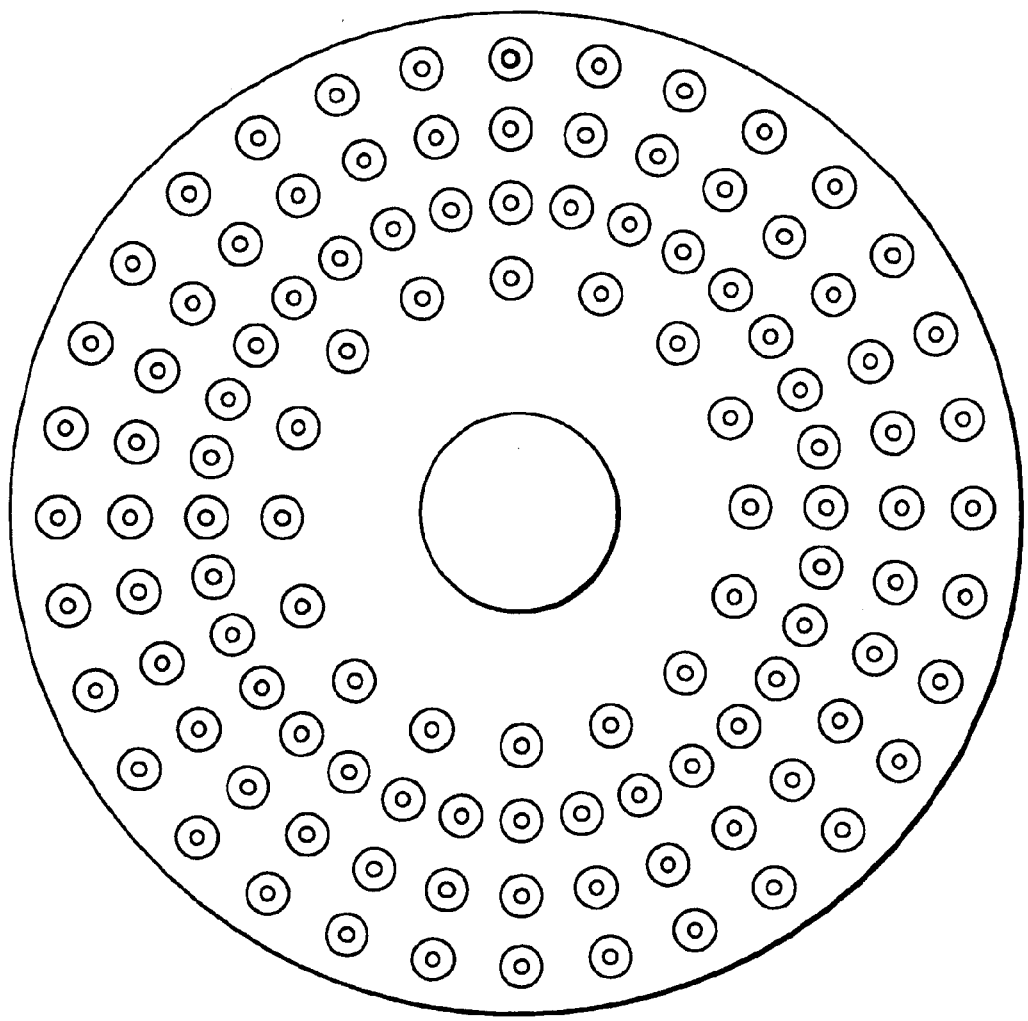
Figure 39:
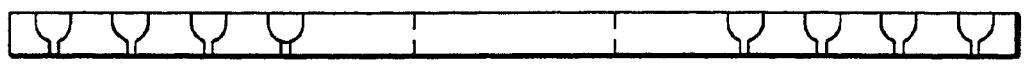
Figure 40:
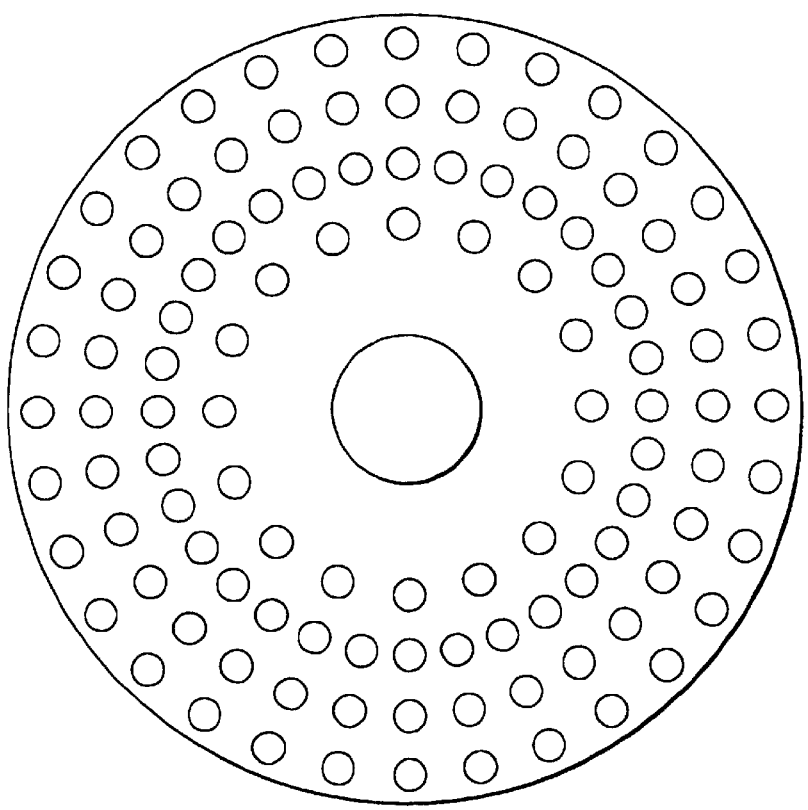
Figure 40:
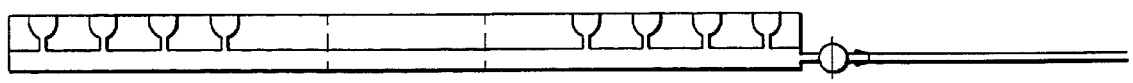

FIG. 37F shows further processing of the assay device to which multiple samples have been applied and shows disposal of the sample application plate;

FIG. 38 shows an alternative geometry for a sample application plate, in which full-thickness air holes, suitable for application of vacuum, are interpolated between sample application wells to prevent sample spread between wells;

FIG. 39 shows an alternative geometry for a sample application plate, suitable for small samples. The cross-sectional view shows hydrophobic channels exiting the sample well to prevent air bubbles from displacing sample;

FIG. 40 shows a sample application plate in which the hydrophobic channels of individual sample wells communicate with a channel to which a vacuum line, controlled by a stopcock, is attached;

FIGS. 41A–L show the use of the sample application plate of FIG. 40.

Figure 41A:
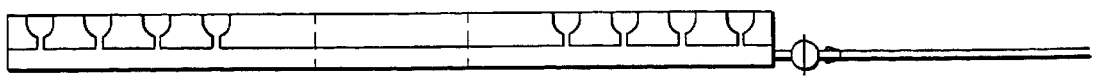

FIG. 41A shows a cross-sectional view of the sample application plate.

Figure 41B:
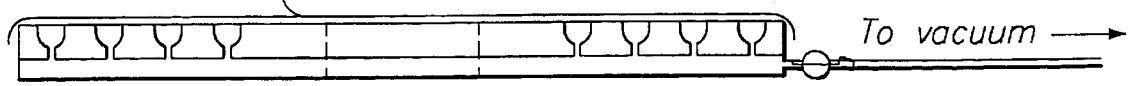

FIG. 41B shows the application of a disposable thin plastic film.

Figure 41C:
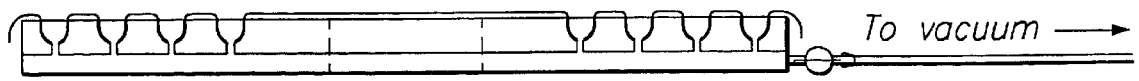

FIG. 41C demonstrates molding of the disposable film to the sample wells upon application of vacuum.

Figure 41D:
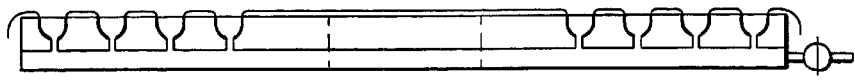

FIG. 41D shows retention of shape due to air pressure differences after closing of the vacuum stopcock.

Figure 41E:
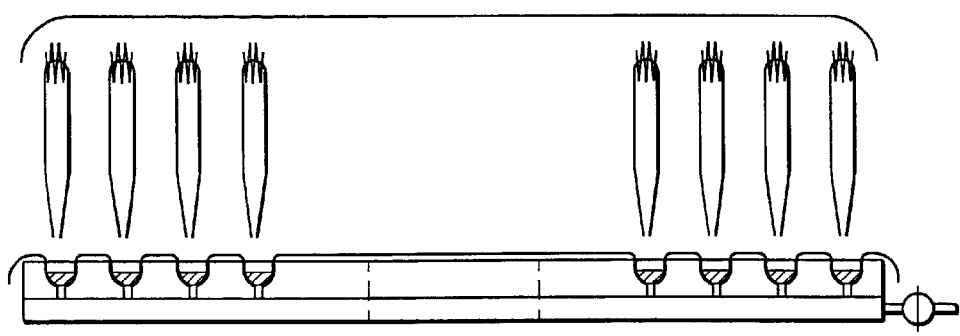

FIG. 41E shows sample addition.

Figure 41F:
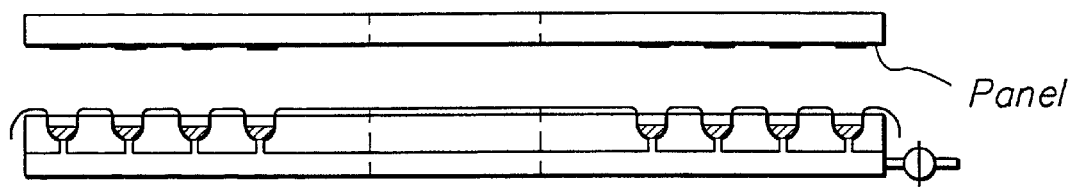

FIG. 41F shows approximation of the assay device to the sample application plate.

Figure 41G:
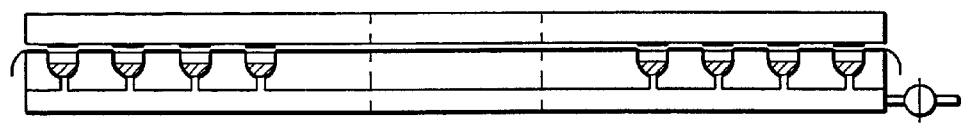

FIG. 41G shows contact, in correct registration, of the assay device to the sample application plate.

Figure 41H:
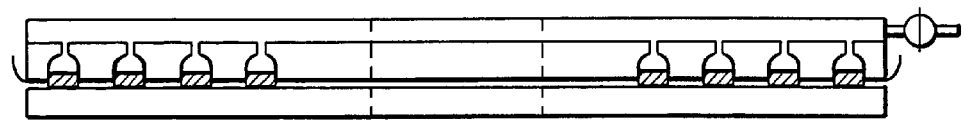

FIG. 41H shows inversion of the approximated devices, permitting gravity-fed application of samples.

Figure 41I:
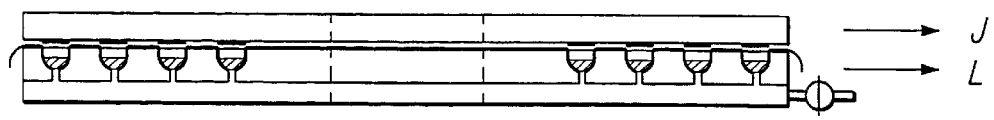

FIG. 41I shows inversion to the original orientation after sufficient time for sample application.

Figure 41J:
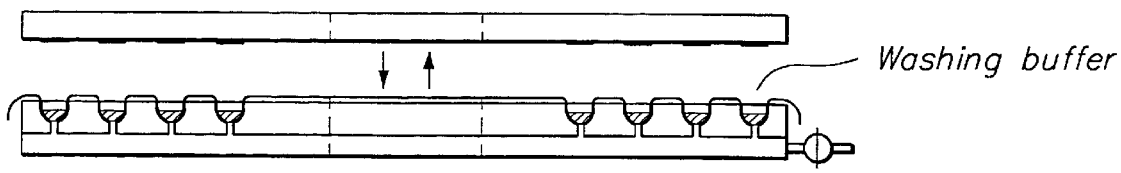

FIG. 41J shows removal of the assay device, addition of washing buffer to the sample application plate, and application in correct registration to the assay device.

Figure 41K:
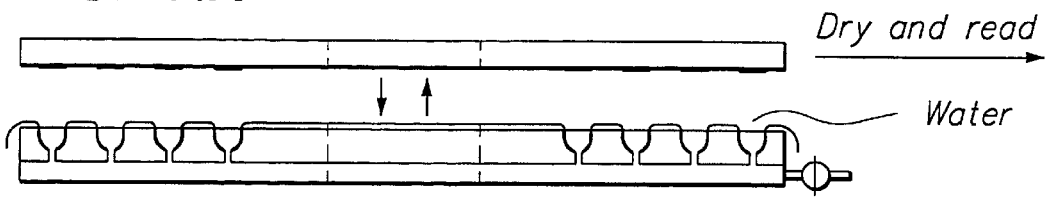
Figure 41L:
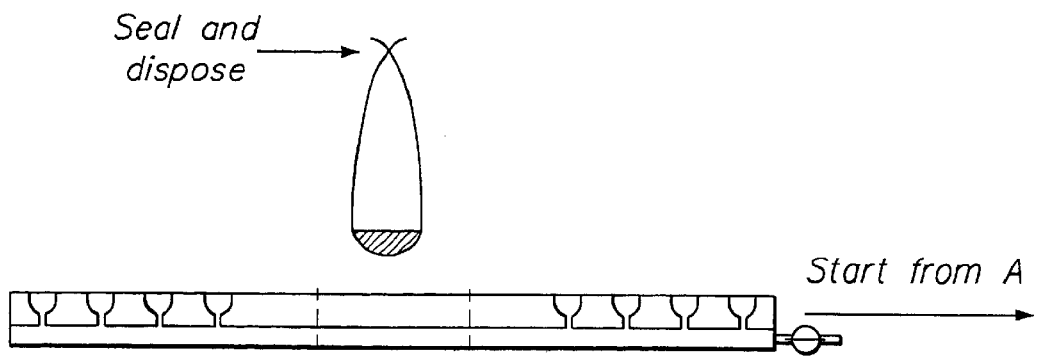
Figure 42A:
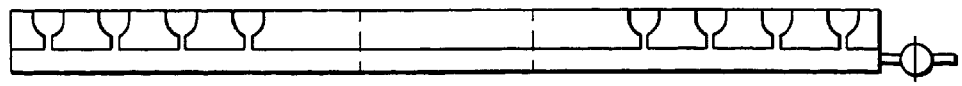
Figure 42B:
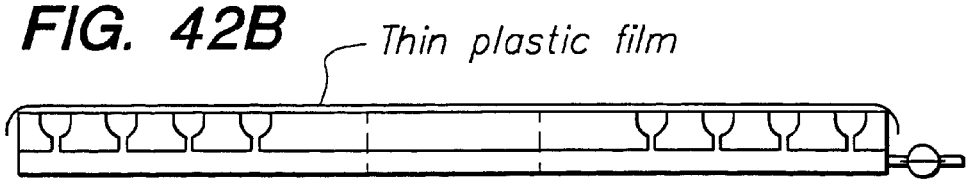
Figure 42C:
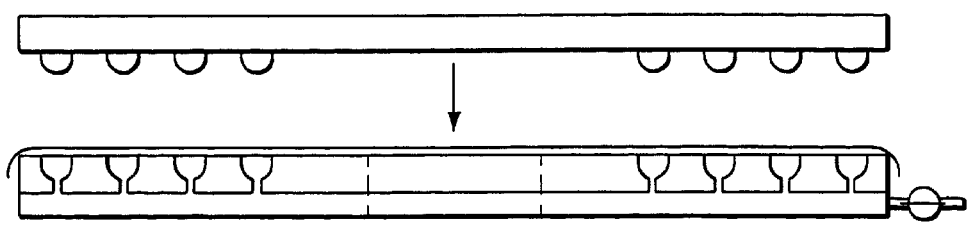
Figure 42D:
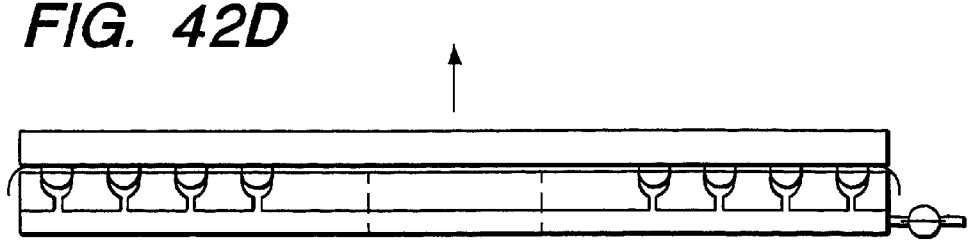
Figure 42E:
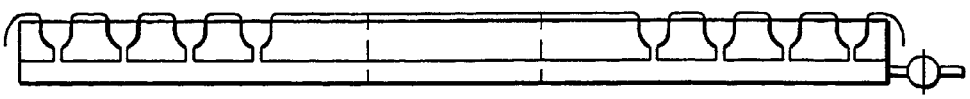
Figure 43A:
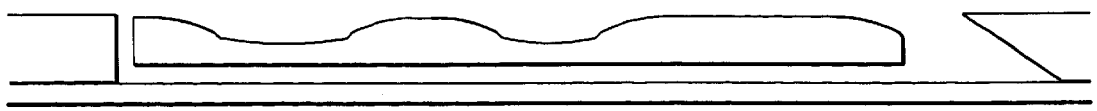
Figure 43B:
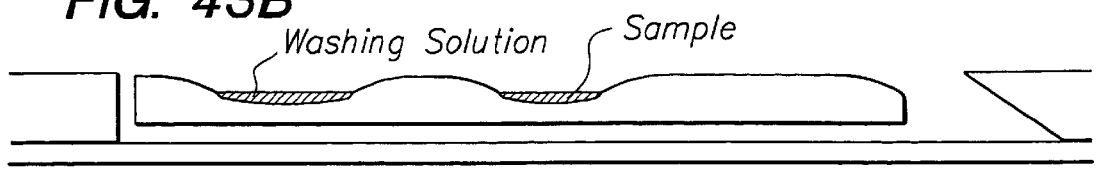
Figure 43C:
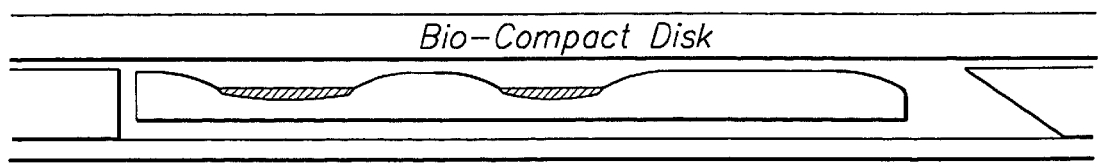
Figure 43D:
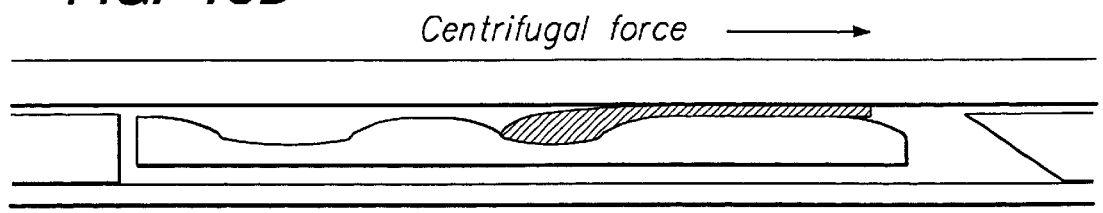
Figure 43E:
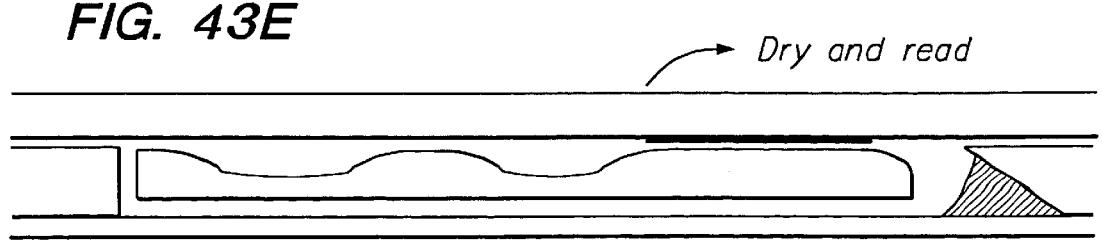
Figure 44:
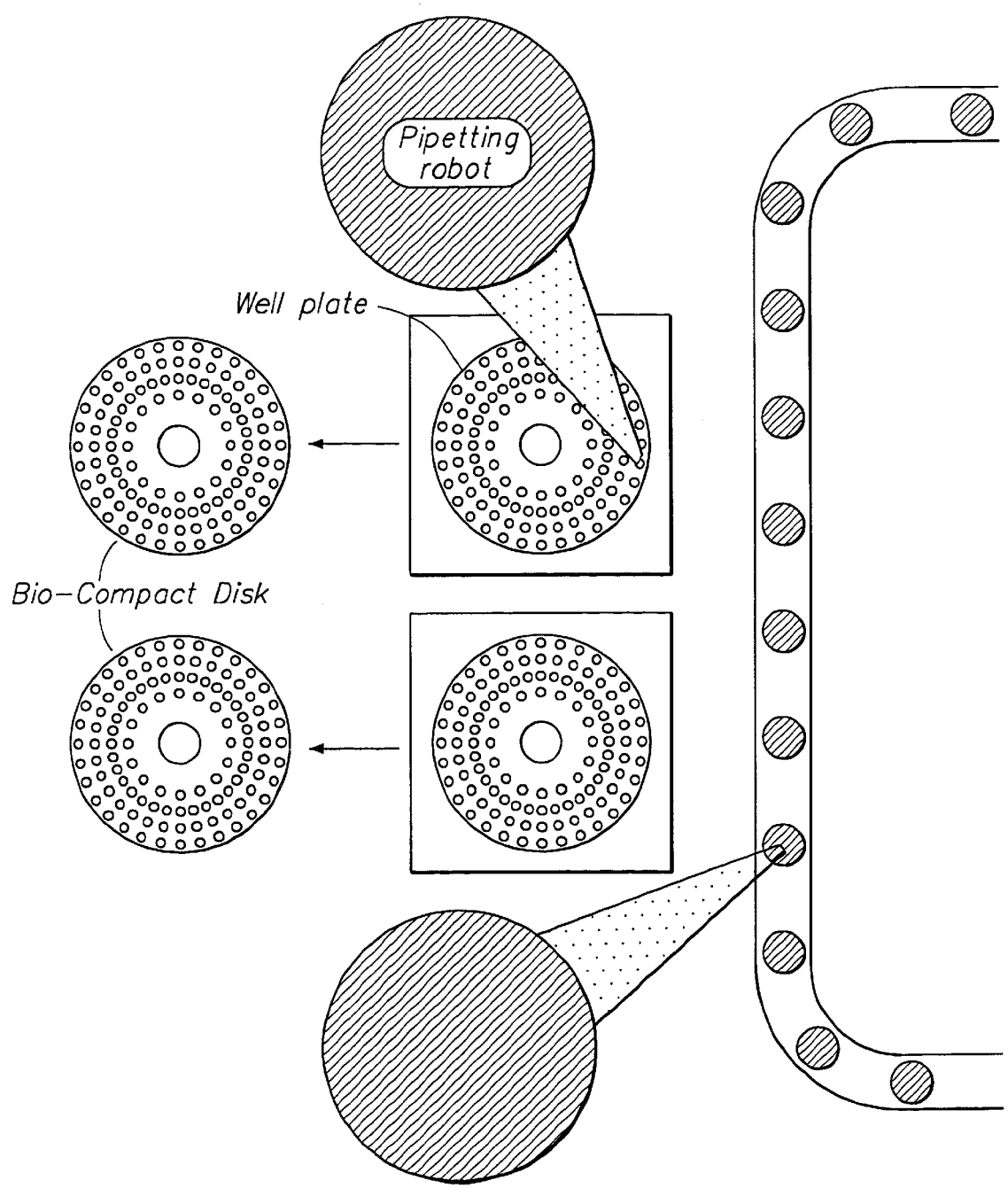

FIG. 41K shows removal of the assay device, further addition of water to the sample application plate, and application thereof in correct registration to the assay device. FIG. 41L shows disposal of the plastic film upon release of vacuum, permitting reuse of the sample application device;

FIGS. 42A–E show a sample application plate similar to that shown in FIG. 41, in which a stamp, shown in FIG. 41C, is used to mold the disposable film to the application plate wells instead of vacuum as in FIG. 41;

FIGS. 43A–E show sequential addition to the assay device, here termed a bio-compact disk, of washing solution and sample, by application of centrifugal force through rotation of the assay device and sample applicator. The assay area is shown as a thick line;

FIG. 44 shows a clinical laboratory embodiment for applying sample.

5. DETAILED DESCRIPTION OF THE INVENTION

The present invention provides an assay device for detecting analyte, comprising an optical disk having analyte-specific signal elements that are disposed readably thereon. The optical disk may be read, and the analyte detection thus performed, using optical disk readers, including those capable of reading audio CD disks, CD-ROM disks, DVD disks, DiVX disks, laser disks, or by readers for other optical disk formats that are similarly useful for digitally-encoding information. In some embodiments the signal elements are readable with the optical disk's tracking features: that is, the analyte-specific signal elements are readable by the optics that read the tracking features, although modified or additional optics are not thereby precluded Unless otherwise specified, terms used herein have their usual and customary meaning, as appropriate to the optical disk and assay arts.

In particular, "analyte", for purposes of this invention, includes any substance, chemical or biological, that one wishes to detect. Thus, "analyte" is intended to include cells when the assay device is adapted for use in cell counting or cell shape detection, to include nucleic acids when the device is adapted for nucleic acid probe detection or nucleic acid sequencing, small organic or inorganic molecules when the device is adapted for chemical assay. The term "analyte" is also intended to cover radiation when the device is adapted, as for example by the use of photoactivatable groups, to detect incident radiation.

In preferred embodiments, the assay device and assay methods of this invention utilize a cleavable signal element for detection of analytes in test samples. Binding of the analyte preselected for detection prevents the loss—through cleavage—of the signal element's signal responsive moiety. Generation of a signal from the signal responsive moiety of the constrained signal element is then used to signal the presence of analyte in the sample.

In a preferred embodiment, the signal responsive moiety reflects or scatters incident light, or is otherwise light addressable. Binding of the analyte preselected for detection prevents the loss—through cleavage—of the signal element's light responsive moiety. Reflection or scattering of incident light, preferably incident laser light, from the reflective moiety of the constrained signal element is then used to signal the presence of analyte in the sample.

The cleavable reflective signal elements of the present invention are particularly adapted for detection using existing laser reflectance-based detectors, including audio compact disk (CD) readers, CD-ROM (compact disk read-only memory) readers, laser disk readers, DVD (digital video disk) readers, and the like. The use of the cleavable reflective signal elements of the present invention thus permits the ready adaptation of existing assay chemistries and existing assay schemes to detection using the large installed base of existing laser reflectance-based detectors. This leads to substantial cost savings per assay over standard assays using dedicated detectors.

Furthermore, the wide and ecumenical distribution of laser-reflection based detection equipment further permits assays—as adapted to use the cleavable reflective signal element of the present invention—to be distributed for point-of-service use, assays that must currently be performed at locations determined by the presence of a dedicated detector. Among these assays are immunoassays, cell counting, genetic detection assays based upon hybridization, genetic detection assays based upon nucleic acid sequencing, nucleic acid sequencing itself, chemical assays, assays for incident radiation, and the like. The current invention thus allows distribution of assay devices to research laboratories, physician's offices, and individual homes that must currently be performed at centralized locations.

Each of the laser-reflectance based detectors mentioned hereinabove—including CD-ROM readers, DVD readers and the like—is adapted for detecting, discriminating, and interpreting spatially addressable digital information on their respective media: audio CD readers are capable of specifically and separately addressing individual digitally encoded audio tracks; CD-ROM readers are capable of specifically and separately addressing multiple binary files, including binary files encoding computer programs (ISO 9660, incorporated herein by reference, defines a common addressable file structure); so too DVD readers are capable of specifically and separately addressing binary files and MPEG-encoded digital video signals.

The spatially addressable capabilities of the laser reflectance-based detectors currently used to detect and interpret information encoded on CDs and the like confer particular advantages on assays adapted to use the cleavable reflective signal elements of the present invention.

Thus, patterned deposition of multiple signal elements on a single supporting member or substrate, coupled with use of a detector capable of addressing the spatial location of these individual signal elements, permits the concurrent assay of a single sample for multiple different analytes. The present invention is thus further directed to assay devices, commonly referred to herein as disks, bio-compact disks, bio-CDs, BCDs, and bio-DVDs, comprising spatially addressable combinations of cleavable reflective signal elements of different analyte specificity. Among such useful combinations are those that increase the predictive value or specificity of each of the individual assays, combinations that inculpate or exculpate particular diagnoses in a differential diagnosis, combinations that provide broad general screening tools, and the like.

Patterned deposition of multiple signal elements with identical specificity further permits the detection, using a single assay device, of large concentration ranges of a single analyte. It is thus another aspect of the present invention to provide assay devices comprising spatially addressable cleavable reflective signal elements of identical specificity, the physical location of which is capable of conveying concentration information.

The spatially addressable capabilities of the laser reflectance-based digital detectors further permits the combination of interpretive software and the assay elements themselves on a single assay device. Another aspect of the current invention, therefore, is an assay device upon which software is encoded in an area spatially distinct from the patterned deposition of cleavable-reflective signal elements. The software may include information important for correct tracking by the incident laser, assay interpretive algorithms, standard control values, self-diagnostics, and the like. The software may include device drivers and software capable of uploading the diagnostic information to remote locations. The software may include patient education information for clinical assays, and may be adapted for chosen audiences.

The substantially binary nature of assay data signaled by the cleavable reflective signal elements of the present invention presents the further advantage of rendering assays adapted to their use substantially resistant to instrumental noise. For example, small variations in light reflection—as from small variations in light intensity provided by the laser source and small variation in reflective particle size—generally do not affect the assay result because the detectors only register a signal when light reflection reaches a threshold. Similarly, electronic noise of the detection device itself and noise associated with an analog to digital conversion do not affect assay results. This advantage is particularly appreciated in designing and manufacturing robust detection instruments useful for field testing or for performing assays under difficult environmental operating conditions.

Furthermore, the substantially binary nature of assay data signaled by the cleavable reflective signal elements of the present invention permits digital correction of imperfections in signal element spatial deposition: the assay device (disk) is read before analysis, the software stores the signal pattern, which pattern is later subtracted from that read after sample application and development of the assay disk.

Figure 1A:
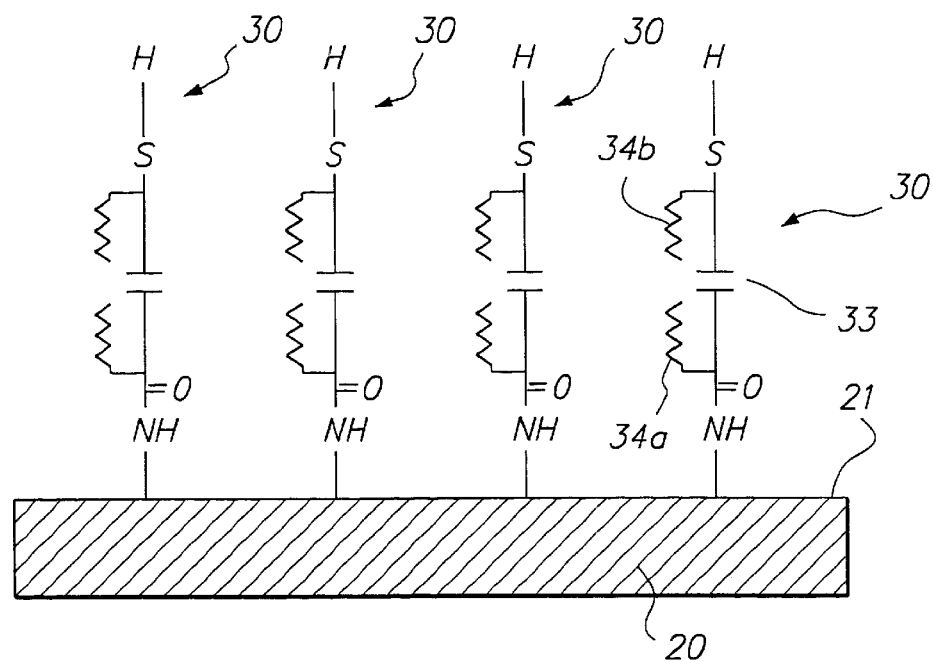
FIG. 1A is a schematic representation of a plurality of cleavable spacers covalently attached at their surface-attaching end to a derivatized site on the assay device substrate.
Figure 1B:
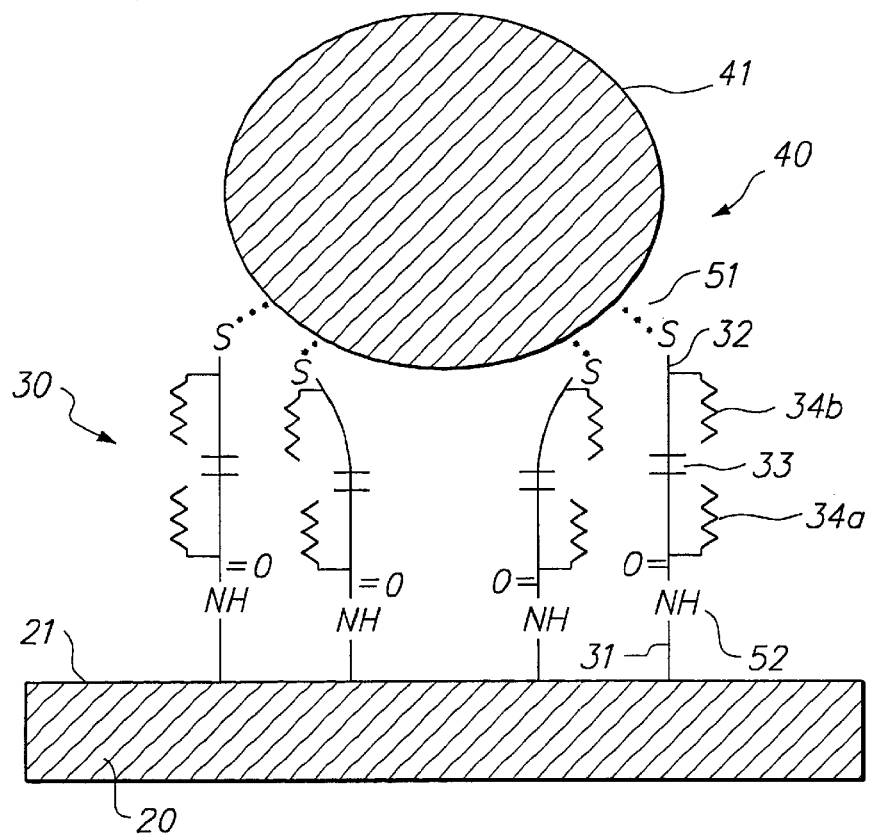
FIG. 1B illustrates the attachment of a reflective signaling means, a metal microsphere, to the signal-responsive ends of the plurality of cleavable spacers, creating cleavable reflective signal elements.

5.1 Assays with Spatially Addressable, Cleavable Reflective Signal Elements 5.1.1 Spacer and Cleavable Site The general operation of the cleavable reflective signal element of this invention, also termed a bio-bit or Biobit, can be understood more particularly by reference to FIGS. 1–3, which schematize two embodiments of the present invention. With reference to FIG. 1, a substrate 20 is provided with a derivatized surface 21 to which is attached cleavable spacer molecules 30, each cleavable spacer having, in addition to a surface-attaching end, a signal responsive end, shown proximal to metal microsphere 40. The substrate, which may be porous or solid, although solid is presently preferred, can be selected from a variety of materials such as plastics, glass, mica, silicon, and the like. However, plastics are preferred for reasons of economy, ease of derivatization for attaching the spacer molecules to the surface, and compatibility with existing laser reflectance-based detectors, such as CD-ROM and DVD readers. Typical plastics that can be used are polypropylenes, polyacrylates, polyvinyl alcohols, polyethylenes, polymethylmethacrylates and polycarbonates. Presently preferred are polypropylene and polycarbonate, and most preferred polycarbonate.

The surface 21 of the substrate 20 can be conveniently derivatized to provide covalent bonding to each of the cleavable spacer molecules 30. The metal spheres provide a convenient reflective signal-generating means for detecting the presence of a spacer molecule bound to the assay device substrate 20. Typical materials are gold, silver, nickel, chromium, platinum, copper, and the like, with gold being presently preferred for its ability readily and tightly to bind e.g. via dative binding to a free SH group at the signal responsive end of the cleavable spacer. The metal spheres may be solid metal or may be formed of plastic, or glass beads or the like, on which a coating of metal has been deposited. Also, other reflective materials can be used instead of metal. The presently preferred gold spheres bind 51 directly to the thio group of the signal responsive end of the cleavable spacer.

Each of the cleavable spacer molecules is attached at one end 31 to support surface 21, e.g. via an amide linkage, and at the other end 32 to a signal generating means (also termed a signal-responsive moiety), e.g. via a thio radical to a reflective metal microsphere 40. The spacer molecule has a cleavage site 33 that is susceptible to cleavage during the assay procedure, by chemical or enzymatic means, heat, light or the like, depending on the nature of the cleavage site. Chemical means are presently preferred with a siloxane cleavage group, and a solution of sodium fluoride or ammonium fluoride, exemplary, respectively, of a chemical cleavage site and chemical cleaving agent. Other groups susceptible to cleaving, such as ester groups or dithio groups, can also be used. Dithio groups are especially advantageous if gold spheres are added after cleaving the spacer.

Cleavage site 33 is between the first, surface-attaching end 31 of cleavable spacer molecule and the second, signal-responsive end 32 of cleavable spacer molecule 30. Spacers may contain two or more cleavage sites to optimize the complete cleavage of all spacers.

Analyte specificity is conferred upon the cleavable spacer by side members 34a and 34b, also termed side arms, positioned on opposite sides of the cleavage site 33; that is, positioned proximal to the surface-attaching end and proximal to the signal-responsive end of cleavable spacer molecule 30, respectively. Side members 34a and 34b in their typical configuration include an oligonucleotide, typically 5- to 20-mers, preferably 8- to 17-mers, most preferably 8- to 12-mers, although longer oligonucleotides can be used. The side members may also include, without limitation and as required, peptides, organic linkers to peptides or proteins, or the like. A large number of cleavable spacer molecules 30 will be present at any particular derivatized site on the solid surface 21 of the assay device, also termed a disk, a blo-compatible disk, or BCD.

5.1.2 Nucleic Acid Assays

In one aspect of the invention, the oligonucleotide side members are adapted to bind complementary single strands of nucleic acids that may be present in a test sample. The complementary oligonucleotides comprise members of a specific binding pair, i.e., one oligonucleotide will bind to a second complementary oligonucleotide.

As is described more particularly in FIGS. 2A through 2C, schematizing one embodiment of the invention, cleavable spacer molecules 30 at different sites on the surface of the assay device will have different oligonucleotide side members. As shown in FIG. 2A, one such cleavable signal element has oligonucleotide side members 34a and 34b, whereas the second cleavable signal element has oligonucleotide side members 35a and 35b.

As further depicted in FIGS. 2A through 2C, when contacted with a test sample containing an oligonucleotide 36, the complementary oligonucleotide side members 34a and 34b will bind with the oligonucleotide present in the sample to form a double helix as is shown in FIG. 2B. Since there is no complementarity between oligonucleotide 36 and oligonucleotide side members 35a and 35b, there is no binding between those groups as is further illustrated in FIG. 2B.

When the cleavage site 33 is cleaved, but for the binding by the double helix coupled oligonucleotides, the metal microspheres 40 will be free of the surface and removed therefrom. This is illustrated more fully in FIG. 2C. If it is desired to assay multiple samples for a single oligonucleotide, the spacer molecules at different sites will generally have the same oligonucleotide side members. Presence and absence of the metal microsphere 40 may then be detected as reflectance or absence of reflectance of incident light, particularly incident laser light.

FIG. 2F is a schematic representation of the use of DNA ligase in a further embodiment of the nucleic acid detection embodiment of the present invention to increase the strength with which analyte-specific binding adheres the signal responsive end of the cleavable spacer to the derivatized substrate of the assay device, thus permitting in this embodiment increased stringency of wash, affording increased specificity of the assay.

It will be appreciated by those skilled in nucleic acid detection that the cleavable reflective signal elements of the present invention are particularly well suited for detecting amplified nucleic acids of defined size, particularly nucleic acids amplified using the various forms of polymerase chain reaction (PCR), ligase chain reaction (LCR), amplification schemes using T7 and SP6 RNA polymerase, and the like.

5.1.3 Immunoassays

In a further embodiment of the invention described in FIGS. 3A through 3C, the oligonucleotide side members 34a, 34b, 35a, and 35b are coupled noncovalently to modified antibodies 38a, 38b, 38c, and 38d to permit an immunoassay. The noncovalent attachment of modified antibodies to side members is mediated through complementarity of cleavable spacer side member oligonucleotides and oligonucleotides that are covalently attached to the antibodies. Use of complementary nucleic acid molecules to effectuate noncovalent, combinatorial assembly of supramolecular structures is described in further detail in co-owned and copending U.S. patent applications Ser. No. 08/332,514, filed Oct. 31, 1994, 08/424,874, filed Apr. 19, 1995, and 08/627,695, filed Mar. 29, 1996, incorporated herein by reference. In another embodiment, antibodies can be attached covalently to the cleavable spacer using conventional cross-linking agents, either directly or through linkers.

The antibodies comprise a first member of a first specific binding pair and a first member of a second specific binding pair. The second member of the first specific binding pair and the second member of the second specific binding pair will be different epitopic sites of an antigen of interest. More specifically, oligonucleotide side member 35a is attached to the antibody-oligonucleotide 38c and oligonucleotide side member 35b is attached to antibody-oligonucleotide 38d. The antibodies 38c and 38d are adapted to bind different epitopic sites on an antigen that may be present in the test sample. By different epitopic sites on an antigen is intended different, spatially separated, occurrences of the same epitope or different epitopes present at distinct sites. At a second assay element, the oligonucleotide side members 34a and 34b are attached to different antibodies 38a and 38b, again each of such antibodies being adapted to attach to a different epitopic site of an antigen.

With further reference to the immunoassay schematized in FIGS. 3A–3C, upon application of the test solution containing antigen 39 to the collection of cleavable reflective signal elements illustrated in FIG. 3A, antigen 39 binds antibodies 34a and 34b, thus preventing decoupling of the metal sphere 40 from the assay device surface 20 when the cleavage site 33 is cleaved, such as, for example, by contact with a chemical cleaving agent. In contrast, the second cleavable signal element, which was not bound by antigen 39 because the lack of binding affinity of the antibodies 35a and 35b to the antigen 39, allow the metal microsphere 40 to separate from the solid surface and be removed from the sample.

Presence and absence of the metal microsphere 40 may then be detected as reflectance or absence of reflectance of incident light, particularly incident laser light.

As should be apparent, coupling of antibodies as depicted permits the ready adaptation of standard immunoassay chemistries and immunoassay geometries for use with the cleavable reflective signal elements of the present invention. Some of these classical immunoassay geometries are further described in U.S. Pat. No. 5,168,057, issued Dec. 1, 1992, incorporated herein by reference. Other immunoassay geometries and techniques that may usefully be adapted to the present invention are disclosed in Diamandis et al. (eds.), *Immunoassay*, AACC Press (July 1997); Gosling et al. (eds.), *Immunoassay: Laboratory Analysis and Clinical Applications*, Butterworth-Heinemann (June 1994); and Law (ed.), *Immunoassay: A Practical Guide*, Taylor & Francis (October 1996), the disclosures of which are incorporated herein by reference. Thus, it should be apparent that the direct detection of analyte (a capture assay) schematized in FIG. 3 is but one of the immunoassay geometries adaptable to the cleavable reflective signal elements and assay device of the present invention.

For example, replacement immunoassays can readily be adapted. In this geometry, a first side member of the cleavable spacer contains an antibody specific for an epitopic site of the analyte, as in the geometry shown in FIG. 3. In contrast to the geometry shown in FIG. 3, however, the second side member has a moiety that displays the determinant recognized by the antibody on the first side member. The default state of the side members, therefore, is a direct binding of the first side member to the second side member, mediated by recognition of the second by the antibody of the first. All signal responsive moieties are thus tethered to the assay device substrate, and addition of cleavage agent releases none of the signal responsive moieties. a more generalized depiction of such a geometry is give in FIG. 35B.

Antigen present in the sample and displaying the appropriate epitopic determinant will displace the immobilized antigen and cut the antigen-antibody loop. As a result, the signal responsive moiety will be liberated after addition of cleavage agent. To increase sensitivity, the immobilized antigen, in this example part of the second side member, should have lower affinity for the immobilized antibody than does the antigen in the sample. For many antibodies a series of antigens having a range of affinities is well known.

Competitive immunoassay is also amenable to adaptation for use with the cleavable spacer and optical disk of the present invention. This geometry is particularly well suited for detection of analytes that are either too small to bridge the gap between first and second side members, or that present a single antigenic epitope.

In this geometry, the first and second side member antibodies are tethered in the default state by a multimeric synthetic antigen. Univalent analyte in the sample displaces one or both antibodies, permitting subsequent loss of the signal responsive moiety after cleavage.

When sample is flowing across the detection surface of the assay device, for instance, through radial flow incident to rotation of the disk, it is possible to combine replacement and capture. In the default state, signal responsive moieties are bound by antigen-antibody interaction to the surface of the assay device. When a sample flows over this area, the antigen or antibody present in this sample serves to detach the signal responsive moieties. These signal responsive moieties, for example metal microspheres, will be captured again in an area that is coated with the corresponding antigen or antibody. The number of spheres reports the concentration of the analyte. The pattern of sphere deposition reports information on the binding kinetics and is characteristic for each analyte. Thus, the binding pattern can be used, e.g., to report the purity of the analyte.

The cleavable signal element embodiments of the present invention present particular advantages for immunoassays. Because the first and second side member antibodies are spatially constrained and in close proximity, the immunoassay is expected to be both fast and sensitive; diffusion of antibodies through a fluid phase is obviated. Moreover, because neither antibody may diffuse from its original site, transient dissociation of analyte from one or the other need not lead to permanent dissociation of the complex: the components will almost certainly recombine before the antigen dissociates from the second antibody. This will increase sensitivity as compared with traditional fluid phase, or semi-solid, immunoassays.

The present invention will prove particularly valuable in immunoassays screening for human immunodeficiency viruses, hepatitis a virus, hepatitis B virus, hepatitis C virus, and human herpes viruses.

It will further be appreciated that antibodies are exemplary of the broader concept of specific binding pairs, wherein the antibody may be considered the first member of the specific binding pair, and the antigen to which it binds the second member of the specific binding pair. In general, a specific binding pair may be defined as two molecules the mutual affinity of which is of sufficient avidity and specificity to permit the practice of the present invention. Thus, the reflective cleavable signal elements of the present invention may include other specific binding pair members as side members. In such embodiments, the first side member of the cleavable signal element includes a first member of a first specific binding pair, the second side member of the cleavable spacer includes a first member of a second specific binding pair, wherein said second member of said first specific binding pair and said second member of said second specific binding pair are connectably attached to one another, permitting the formation of a tethering loop of the general formula: first member of first specific binding pair-second member of first specific binding pair-second member of second specific binding pair-first member of second specific binding pair.

Among the specific binding pairs well known in the art are biologic receptors and their natural agonist and antagonist ligands, proteins and cofactors, biotin and either avidin or streptavidin, alpha spectrin and beta spectrin monomers, and antibody Fc portions and Fc receptors.

5.1.4 Chemical Assays

In yet another embodiment of the present invention, the analyte-specific side members are chosen to react with specific functional groups presented by an analyte, as exemplified in FIGS. 29, 30 and 31.

In general, functional groups that are present in small organic or biological molecules, such as amino, aldehydo, keto, carboxylic and thiol groups can readily be detected using the cleavable spacer embodiment of the present invention, so long as the molecule contains at least two such functional groups and is large enough to form a bridge between recognition molecules, thus tethering the signal responsive moiety to the assay device substrate.

The bridge need not necessarily lead to formation of a covalent bond. Acid-base interaction, hydrogen bonding, coordinate bonding and even van der Walls interaction can be used to secure the signal responsive moiety to the disk assay substrate. For example, both side-elements can contain alkylamine diacetic acid unit, i.e., half of EDTA. These side-elements will bind strongly to divalent cations, such as calcium and magnesium ions. To confer greater analyte specificity, crown ethers and cryptands can be used.

Furthermore, if the analyte is too small to bridge the space between first and second side members, a competitive assay geometry may usefully be employed, the analyte serving, either directly or indirectly, to displace the binding of the signal responsive moiety, as further exemplified in Example IV, below. And as further discussed below with respect to spacer cleavage chemistries, it should be appreciated that in certain circumstances the analyte specificity may be conferred directly by the cleavage site, or by the cleavage site in association with auxiliary recognition molecules, without the need for spacer side members or further addition of a cleavage agent.

Turning, then, to the figures, FIG. 29 presents cleavable spacers that contain a first and second side member that permit selective detection of norepinephrine.

The first side member, proximal to the solid support substrate, here an optical disk, contains a phenyl boronic acid moiety, which will react with a molecule presenting two hydroxyl molecules in close proximity. The second side member, proximal to the signal responsive moiety, here a gold sphere, contains a pthalaldehyde group, which will react with a primary amine.

Upon contact with norepinephrine under reducing conditions the two side members react, thus forming a covalent bridge between the side members. Upon cleavage, the signal responsive moiety is securely tethered to the disk substrate, giving a positive signal indicative of the presence of norepinephrine in the sample.

FIG. 30 depicts cleavable spacers adapted to detect amino acids using the ninhydrin reaction. Traditionally, the ninhydrin reaction has been adapted to generate a colored end product that can be detected visually or spectrophotometrically. Here, the reaction is adapted to permit detection on an optical disk.

Many such existing analytic reactions may be adapted to the optical disk-based devices and methods of the present invention.

Although it is the spacer side members that confer analyte specificity in the two examples given above, analyte specificity may also be conferred by auxiliary molecules distinct from the spacer side members. In particular, analyte specificity may be enhanced by coupling the high substrate specificity of enzymes to the chemical reactivity of the side members, as exemplified in FIG. 31.

FIG. 31 presents an example of adapting existing enzymatic chemistries to the detection of ethanol using the cleavable spacer embodiment of the present invention. In FIG. 31A, the assay device solid support substrate is shown above, with the cleavable spacers depending below. Each signal responsive moiety is attached in this example by two identical cleavable spacers, the first and second side members of which contain the terminal hydroxyl of polyethylene glycol and a primary amine, respectively. In addition to the cleavable spacers with their signal responsive moieties, two enzymes are also attached to the assay device substrate surface. One is alcohol oxidase, the other catalase.

As shown in FIG. 31A, ethanol in the sample serves as a substrate for alcohol oxidase present on the substrate surface, producing acetic acid and hydrogen peroxide. As shown in FIG. 31B, the hydrogen peroxide, in the presence of catalase, oxidizes the terminal hydroxyl group of the first side member, coupling the first side member to the second, thus tethering the signal responsive moiety to the assay device substrate It will be appreciated that in this example it is the enzyme, alcohol oxidase, that provides the analyte specificity. Conversely, the same chemistries may equally be adapted to detect the presence of the enzyme itself in the sample. In the assay given in FIG. 31, for example, omitting the enzyme alcohol oxidase from the substrate surface allows assay for alcohol oxidase in the applied sample. In this altered geometry, ethanol is added to the sample to drive formation of peroxide in those samples in which ethanol oxidase is present.

It will also be appreciated that the specificity of enzymes for biological substrates serves as the basis for many existing assays, all of which may be adapted, as exemplified here, for detection in optical disk-based assays.

5.1.5 Assays for Electromagnetic and Ionizing Radiation

In yet another embodiment, the cleavable spacer of the present invention can be used to detect electromagnetic radiation (FIG. 32). High resolution imaging applications will particularly benefit from the nanometer scale resolution that can be obtained by this method.

As with chemical detection, two distinguishable geometries are readily suggested: (1) the first and second side members are coupled by electromagnetic radiation, or (2) the spacer is directly cleaved by electromagnetic radiation. In the first case, it is the retention of the signal responsive moieties in a spatially-identified area after addition of cleavage agent that reports the location of electromagnetic signal; in the second case, it is the loss of signal responsive moieties from a spatially-identified area, without further addition of a cleavage agent, that reports the electromagnetic signal. Both detection methods can be made sensitive for particular wavelengths by using chromophores.

Examples of functional groups that are sensitive to UV and/or visible wavelengths include diacetylenes and azido groups. If both members of a binding pair are diacetylenes, they can dimerize and even polymerize, provided that the spacer side members contain a sufficiency of diacetylenes, or the spacer side members are close enough so that interspacer reaction is possible. As for azido groups, upon receipt of a photon they generate a free radical, which will couple with almost anything.

X-ray or γ-radiation as well as ionizing or free radical forming radiation will couple many kinds of binding pairs or, alternatively, cleave the spacers. Scintillation compounds may be used to control the process so that the high energy is transformed either to UV or visible radiation Regular film, such as IR-, visible, or X-ray film, can be applied directly to the substrate surface of the assay device, either before the exposure or after the development of the film. In this case the assay device will has a reflective metal coating. The laser light will be absorbed according to the darkness of the film and the reflection is reduced. The film can be visualized and processed on the computer screen.

5.1.6 Modifications of Cleavable Spacer Assays

While the above-exemplified embodiments of assays using the cleavable reflective signal elements of the present invention—detection of nucleic acid analytes, immunoassay, assay for functional groups on small organic molecules, and detection of radiation—have been described with signal responsive moieties, such as reflective metal spheres, attached to the cleavable spacer molecules prior to conducting the assay, it is contemplated in these and other embodiments further described herein that cleavable spacer molecules lacking a signal generating means can first be exposed to sample, then cleaved, and the metal spheres added later so as to attach to only those spacer molecules remaining on the surface. After addition of the metal spheres, the surface can then be read with an appropriate detector to identify the bound spacer molecules and analytes.

In yet another modification, the spacer cleavage site may contain, instead of a chemically-cleavable functional group such as siloxane, a specific binding pair that is dissociated by binding of the analyte. One such geometry is shown in FIG. 35B, and is further discussed below in section 5.9.

Furthermore, the cleavable spacer of the present invention, which in preferred embodiments of the present invention are particularly adapted for detection in optical disk readers, may also usefully be employed on other substrates. These include, but are not limited to, paper and plastic strips, multiwell plates, magnetic disks (floppy disks), and silicon chips. For example, gating by a field effect transistor depends upon the local electric field; the field, in turn, may usefully be modified by the analyte-specific binding of signal responsive moieties such as metal, salts, such as strontium titanate, or polymers, such as polyacetylene, polyaniline, polyphenylene, or carbon nanotubes.

5.1.7 Sample Application, Wash, and Cleavage

In each of the assay method embodiments of the invention, a sample to be tested must be introduced. Devices particularly designed to facilitate sample application are further described in a section below. General aspects of sample addition will be discussed here.

In one aspect, the assay device is rotated and a fluid sample, preferably diluted, is applied near the center of the circular assay device substrate. The centrifugal forces associated with the rotation of the assay device disk distribute the fluid sample across the planar face of the solid substrate. In this manner the surface of the substrate is uniformly covered with a constant and uniformly distributed fluid sample.

In this method of sample application, the test sample, initially about 100 μl, is diluted for processing to about 1 ml. This solution is added dropwise near the center of the rotating disk. The assay sites and possibly the surface of the disk are hydrophilic and a fluid will form a very thin layer on the rotating assay device disk. The thickness of the fluid layer can be regulated by the frequency of drop addition and frequency of disk rotation. a preferred thickness is less than 10 μm, because all molecules in the sample can then interact with the stationary molecules bound by the spacers. About 100 μl of the sample solution is needed to cover the disk.

Other methods of sample application may be used with the cleavable reflective signal element and assay device of the present invention. In particular, it should be appreciated that the rotational application above-described is suitable principally for application of a single sample per assay device. In other aspects of the present invention, separate samples may be applied to discrete areas of a stationary disk. In this aspect, the assay system can assay approximately one thousand different samples. Approximately one million gold spheres, which are applied onto a predetermined areas on the disk, can be dedicated for each sample.

FIG. 11D shows an assay device of the present invention having 16 separate assay sectors. FIG. 11E shows a possible direction for sample flow, with barriers to fluid flow shown as lines.

Thus, in one embodiment of the invention, the assay device is designed to assay, for example, 1024 patient samples simultaneously, one analyte per assay device (i.e., per disk, each disk comprising a plurality of cleavable spacers with identical side members conferring identical analyte specificity). In such an embodiment, each of the spacer molecules on the disk may be identical, so as to assay for the same analyte; spacer molecules at particular locations on the disk will be identical to spacer molecules at other locations on the disk. This application is particularly useful in mass analysis conducted in clinical laboratories where a large number of patient samples are analyzed at the same time for the presence or absence of a single analyte.

It will also be appreciated that multiple samples may be assayed for multiple analytes on a single assay device comprising cleavable reflective signal elements with various analyte specificities. FIG. 11F shows an assay device that can be used to screen 20 samples for 50 different biomolecules.

In the latter case, it is possible to assay for a limited number of the same analytes in a multiplicity of test samples. Patient samples may be applied to the disk at specific locations by known methods such as ink jet printing and micropipet arrays with disposable tips, or a combination thereof. For large through-put operations, the assay disks may be loaded into a cassette and test samples loaded hermetically either directly onto the disk or into the wells in a circular plate.

After an appropriate incubation period, which may only be a few seconds to allow the sample to traverse the surface of the support, a wash step may be, but in some embodiments need not be, performed to remove unbound sample. Wash stringency may be adjusted as in conventional assays to adjust sensitivity and specificity. For example, in nucleic acid detection embodiments, the salt concentration of the wash solution may be decreased to increase the stringency of wash—thus reducing mismatch as between analyte and specificity-conferring side members—or increased, to decrease the stringency of wash, thereby permitting mismatch to occur. Adjusting the stringency of wash in the nucleic acid hybridization and immunoassay embodiments of the present invention is well within the skill in the art.

In one aspect, the surface of the circular disk is washed, when necessary, by adding a wash solution near the center of the rotating disk. The sample solution is removed as it pushes out from the periphery of the disk and is collected. Because of the rotation of the disk, the wash step may be eliminated if the fluid sample is adequately removed from the disk by normal centrifugal forces and no adjustment to stringency is required.

After the wash step, if any, a solution including a cleaving agent is added and again distributed over the surface of the disk. With reference to FIGS. 1–3, the spacer molecule has a cleavage site 33 that is susceptible to cleavage during the assay procedure, by chemical or enzymatic means, heat, light or the like, depending on the nature of the cleavage site. Chemical means are presently preferred with the siloxane cleavage group, and a solution of sodium fluoride is exemplary as a chemical cleaving agent for the siloxane group. Other groups susceptible to cleaving, such as ester groups or dithio groups, can be used. Dithio groups are especially advantageous if gold spheres are added after cleaving the spacer.

In the case of the cleavage site being a siloxane moiety, which can be made stable against spontaneous hydrolysis but is easily cleaved under mild conditions by a fluoride ion, a solution of sodium or ammonium fluoride is introduced, with concentration of 1 mM to 1 M, preferably 50 mM to 500 mM, most preferably 100 mM (0.1 M). The cleavage step will last only a few seconds. Although all spacers are cleaved during this step, the amide bond between the cleavable spacer and the derivatized substrate of the assay device remains stable to these conditions.

After application of sample and cleavage of the spacers, the detached signal-generating moieties, preferably a reflective moiety, more preferably a metal sphere, most preferably a gold sphere, must be removed to provide differential signal during detection. The removal step may include a second wash step, which may include introduction of wash solutions.

Several means exist by which differential wash stringencies may be developed at this stage of the assay, thereby permitting variation in the specificity and sensitivity of the various assay methods.

In one aspect, the detached reflective moieties may be removed by rotating the assay device, with or without addition of wash solution. In this aspect, three parameters may be varied to provide differential stringency: gold particle size, rotational speed, and the valency of spacer attachment.

Gold spheres suitable for use in the cleavable reflective signal element and assay device of the present invention are readily available in varying diameters from Aldrich Chemical Company, British BioCell International, Nanoprobes, Inc., and others, ranging from 1nm to and including 0.5–5 micrometers in diameter. It is within the skill in the art to create gold spheres of lesser or greater diameter as needed in the present invention. At a given rotational speed, the largest gold spheres experience larger centrifugal (relative to $r^3$) and drag forces (relative to r) and are removed before smaller spheres with equal bonding. This provides a basis for differential stringency of wash, and also of quantitative analysis.

The centrifugal force affecting the gold spheres may also be adjusted by rotation frequency so that the loose and weakly bound gold spheres are removed. Only the spacers which have bound to a complementary molecule from the sample will continue to bind the gold spheres to the substrate Furthermore, while the above embodiments of the invention have been described with a single metal sphere attached to the signal-responsive end of a single cleavable spacer, it should be appreciated that when gold is used in a preferred embodiment of the invention, thousands of spacers may bind one gold sphere, depending upon its diameter. Thus, the stringency of the assay wash may be adjusted, at any given rotational speed, by varying the diameter of the gold sphere, and by varying additionally the relative density of cleavable spacers to gold spheres.

Thus, if virtually all spacers under a certain gold sphere are connected by complementary molecules, the binding is very strong. If the spacers are fixated only partially under a certain gold sphere, the sphere may remain or be removed depending on the radius of the sphere and the frequency of the rotation.

In extreme cases all spheres are either fixed or are removed. These are expected alternatives for DNA analysis. In immunoassays the intermediary cases are preferred Accordingly, the system should be optimized so that the normal control level corresponds to 50% fixation of the gold spheres. Higher or lower fixation corresponds to higher or lower concentrations of the analyte, respectively, when using two antibodies for binding as illustrated in FIG. 3.

a strong centrifugal force can be used to remove weakly bound gold spheres. The centrifugal force pulling one gold sphere will be in the order of 0.1 nN, although this force can vary within large limits depending on the mass of the gold sphere and the frequency of the rotation of the disk. The force is strong enough to rupture nonspecific binding of antibodies and to mechanically denature mismatching oligonucleotides. This is a very strong factor for increasing the specificity of the interaction between analyte and the cleavable signal elements of the present invention.

In embodiments of the present invention in which the reflective moiety of the cleavable spacer is ferromagnetic, as, for example, in which the reflective moiety is a gold-coated iron bead or an iron alloy, those reflective moieties detached through cleavage and not secured to the assay device substrate by analyte may be removed through application of a magnetic field. In such embodiments, those signal elements that remain attached to the assay device (disk) substrate will also be responsive to the magnetic field, but their motion will be constrained by the length and flexibility of the loop formed by the first side member-analyte-second side member. The ability to shift the position of all attached signal elements through application of an external magnetic field, even though that shift will necessarily be constrained by the length and flexibility of the first side member-analyte-second side member loop, may add, in this embodiment, additional information. In particular, brief application of a magnetic field will facilitate discrimination of analyte-induced signal from random noise, the noise being unresponsive to the application of an external magnetic field.

After removal of cleaved reflective signal moieties that are not protected by the specific binding of analyte, the disk may be read directly. Alternatively, the disk may first be disinfected before reading. In yet another embodiment, the disk may be covered by an optically clear plastic coating to prevent the further removal of the gold spheres through spin coating with a polymerizable lacquer that is polymerized with UV-light. Spin coating of compact disks is well established in the art. The assay disk is expected to have a shelf-life of well over ten years.

Subsequently, the disk can be scanned by a laser reader which will detect, through reflection, the presence of a microsphere or other reflective element at the various spatially predetermined locations. Based on the distance of the microsphere from the axis of rotation of the disk and the angular distance from an address line forming a radial line on the disk, the location of a particular metal sphere can be specifically determined. Based on that specific location and the predetermined locations of specific binding pairs as compared to a master distribution map, the identity of the bound material can be identified. Thus, in the foregoing manner it is possible in one fluid sample to analyze for thousands, or even greater numbers, of analytes simultaneously.

5.2 Derivatization of Substrate

Figure 4A:
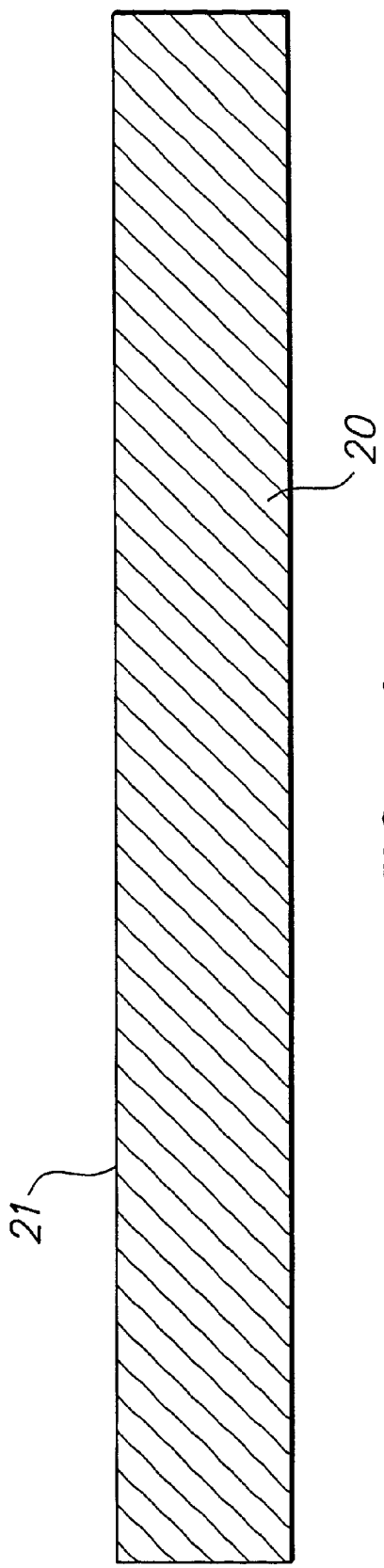
Figure 4B:
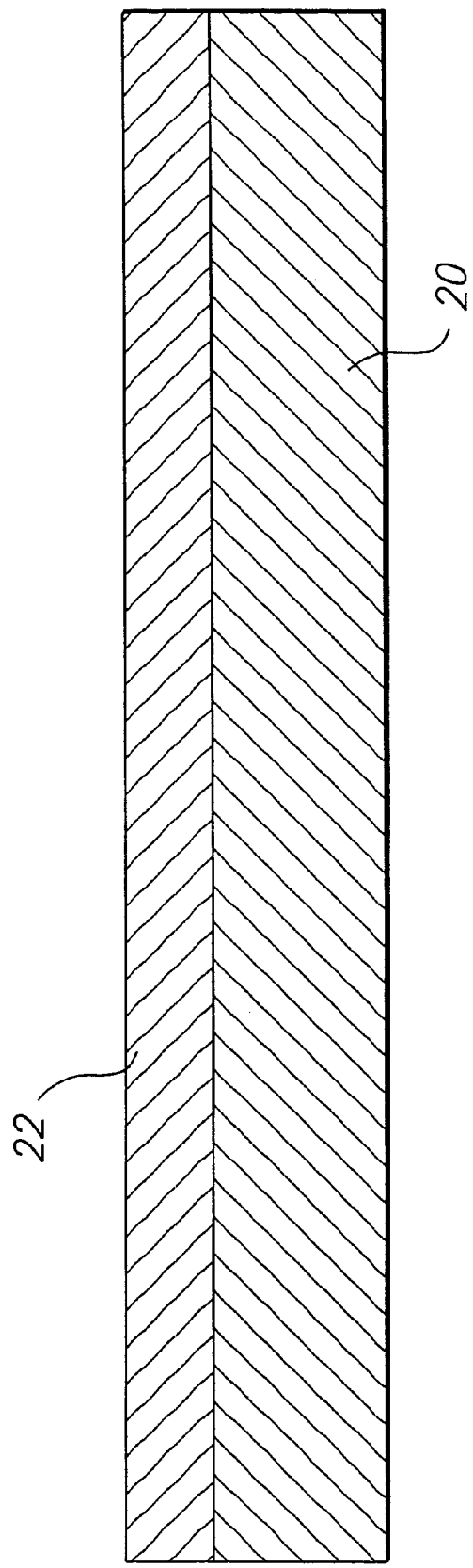
Figure 4C:
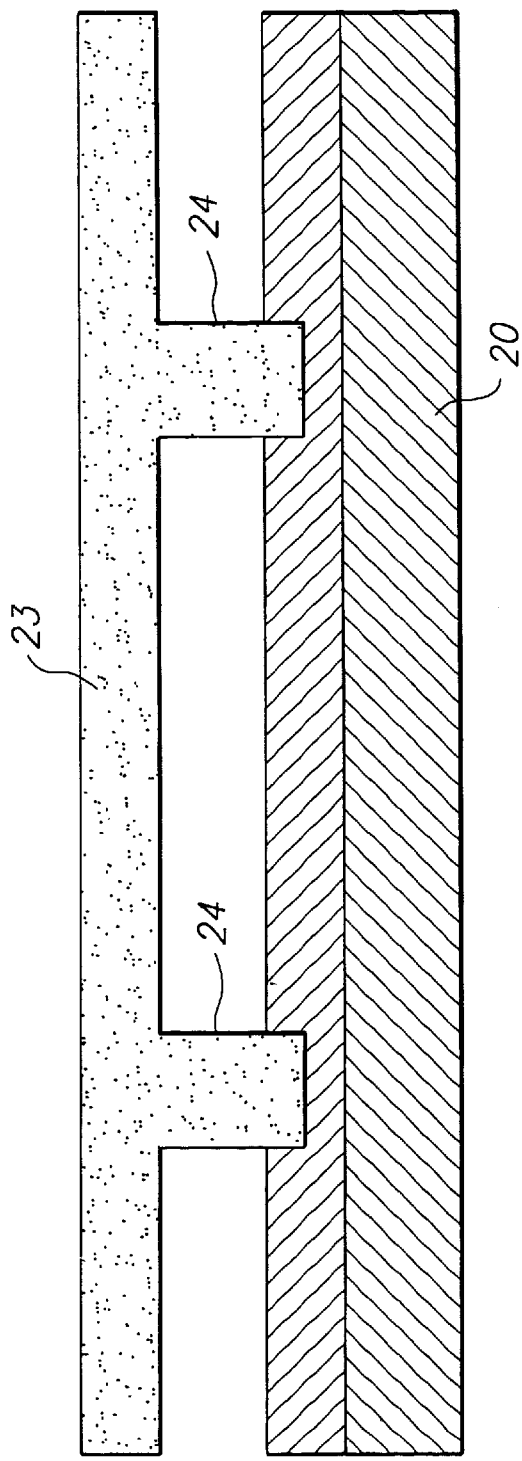
Figure 4D:
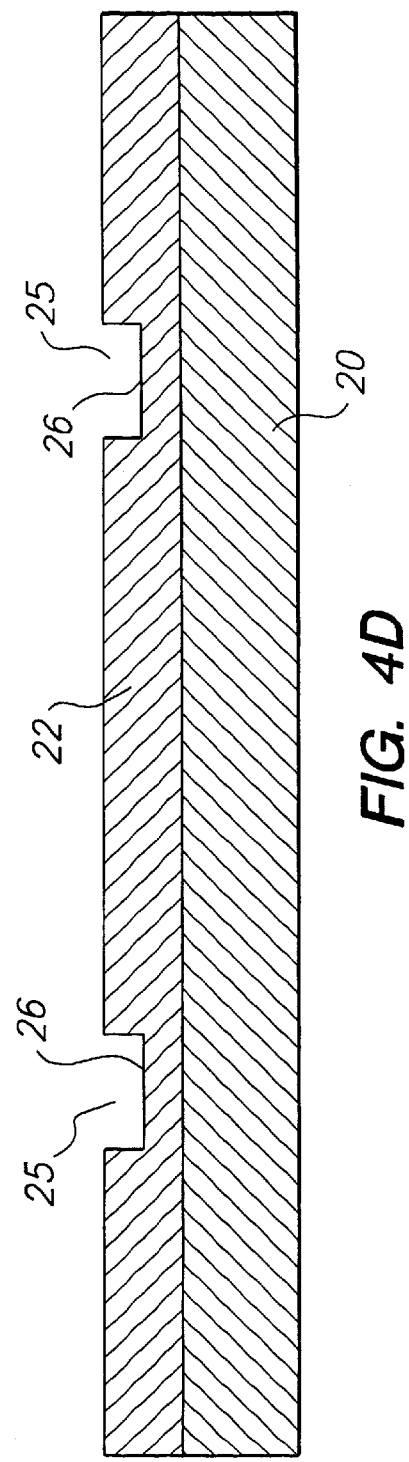
Figure 4E:
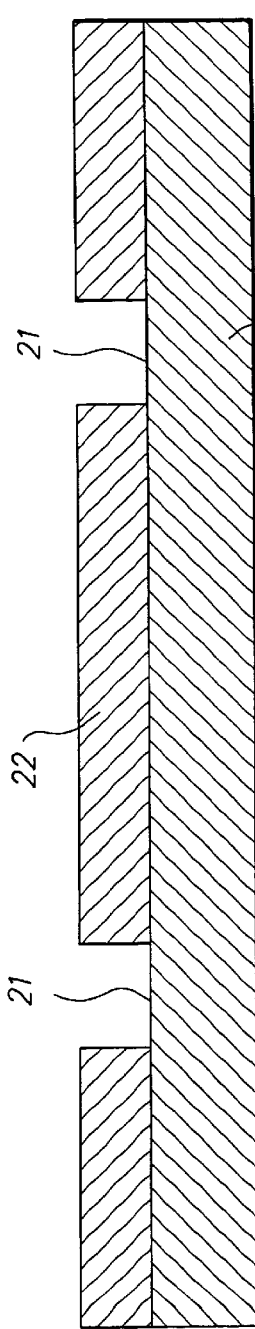
Figure 4F:
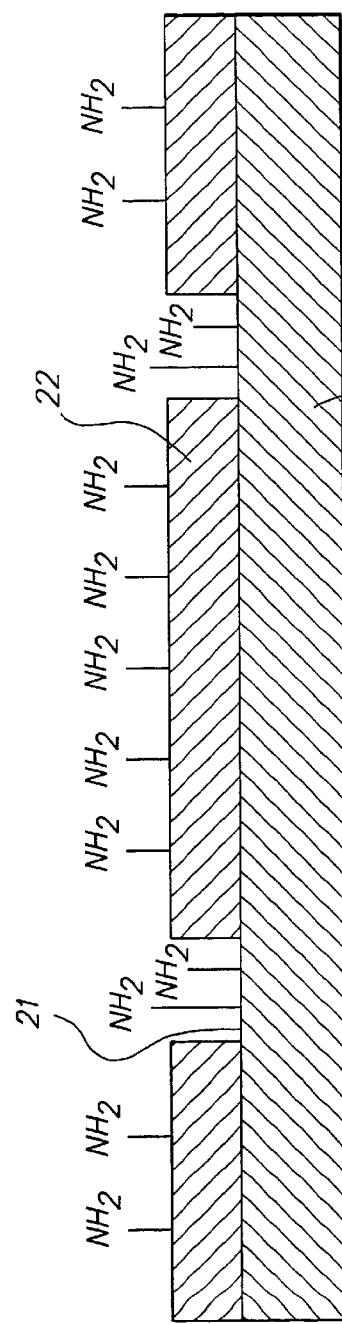
Figure 4G:
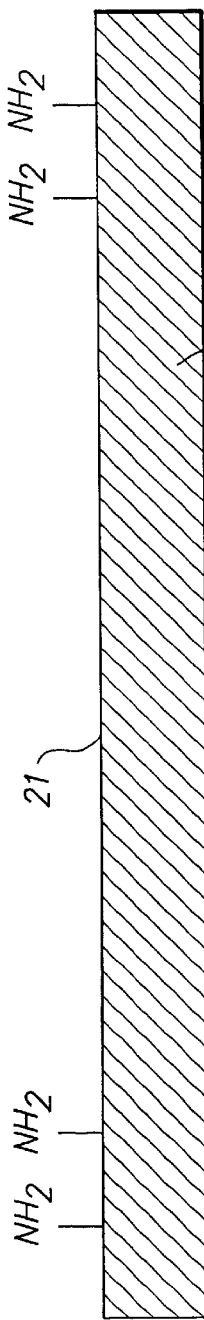

FIGS. 4A through 4G illustrate schematically one way in which the solid support substrate is prepared for deposition of cleavable reflective signal elements to create an assay device of this invention a portion of a generally planar solid support is illustrated in FIG. 4A. As illustrated in FIG. 4B, the surface of the support is coated with a resist 22, e.g., a high melting point wax or the like. Next a pattern of indentations or holes 25 in the resist is created by stamping with stamp 23 containing protrusions 24, as illustrated in FIG. 4C. The pattern is highly regular and indentations are made in all sites at which cleavable spacer molecules will desirably be located on the surface of the support. Any resist remaining at the bottom of the indentations, as illustrated in FIG. 4D, is removed, as shown in FIG. 4E. The exposed areas of the substrate 21, as illustrated in FIG. 4E, are activated or derivatized to provide for the attachment of bonding groups (e.g., amino groups) to the surface of the substrate and to any remaining resist 22, as represented in FIG. 4F. Finally, the remaining resist is removed to expose the original surface of the substrate to which amino groups are coupled at certain predetermined sites as illustrated in FIG. 4G.

Blank disks are available from Disc Manufacturing, Inc. (Wilmington, Del.). Amino derivatization may be performed by ammonia plasma using a radio frequency plasma generator (ENI, Rochester, N.Y.).

More generally, when the assay device substrate is plastic, as in many of the optical disk embodiments of the present invention, the plastic substrate surface onto which spacers are to be deposited should contain enough reactive groups, such as amino, thiol, carboxyl, aldehydo, or keto, to enable the covalent attachment of spacers, biomolecules, and coating agents. These active groups may be introduced in any of a number of ways well known in the art, e.g., by mixing of surface active compounds, such as polyethylene glycol ammonium halogenide, with the plastic polymer during synthesis of the assay device substrate; by ammonia, oxygen, halogen or other reactive plasma etching; or by wet chemical reaction, such as acid or alkaline hydrolysis, nitration and subsequent reduction, etc. It should be kept in mind that on some occasions, some of the structures to be applied to the device surface can be attached by van der Waals and other nonspecific or noncovalent forces.

Other physical and chemical properties of the assay device detection surface (that is, the solid support substrate to which analyte-specific signal elements are attached) can be modified, for purposes additional to facilitating the bonding of signal elements.

For instance, wettability can be adjusted.

Hydrophilicity may be achieved by the amination of the surface, which also facilitates binding of signal elements, and may also be achieved by attaching hydrophilic molecules to the device surface. These molecules include detergents, carbohydrates, oligonucleotides, peptides, proteins, synthetic polymers, such as polyvinyl alcohol, polylactic acid, polyethylene glycol, and polyethyleneimine. Similarly, hydrophobic areas can be created by molecules that contain aliphatic alkyl groups or perfluorinated alkyl groups. For binding to the solid support substrate, these molecules can have carboxyl, hydroxyl, amino, carbonyl, or another group that can be easily coupled with a surface. Coupling can be covalent or based on weaker bonding, such as van der Waals interaction.

The surface may also be modified to reduce nonspecific binding. One general method is silylation (Virtanen J. A. et al., "Organosilanes and their hydrolytic polymers as surface treatment agents for use in chromatography and electronics," U.S. Pat. No. 4,756,971, incorporated herein by reference).

Alternatively, it is known that polyethyleneglycol (PEG)-coated particles have much less interaction with biomolecules than do uncoated particles. However, direct PEG-coating of the elements that confer analyte specificity will also significantly reduce specific binding. For this reason, binding molecules, such as antibodies, may be tethered with PEG onto supporting surfaces. The PEG serves to prevent nonspecific binding to the surface; specific binding by the recognition molecules, displayed away from the surface, is unaffected.

The cleavable spacers of the present invention, the backbone of which consists, in preferred embodiments, of PEG, are themselves an example of this principle: the reduction in nonspecific binding, with concomitant increase in specificity, occasioned by removing the recognition moieties from the device substrate to a PEG spacer, is a significant advantage of the present invention, and further argues for adapting existing nucleic acid detection and immunoassays to the cleavable spacers of the present invention.

To reduce nonspecific binding of sample components, the assay device detection surface, and/or other surfaces of the assay device that contact sample, may also be coated with soluble proteins that do not have any specific interaction with other proteins or large biomolecules. Examples of these are albumin, ovalbumin, prionex, avidin, streptavidin, gelatin, casein, neutral IgG, α1-acid glycoprotein, and hemocyanin. Thus, albumin is a very good coating material for all assays, but especially for the immunoassays.

For nucleic acid assay devices, the surfaces can be made negatively charged by carboxylate, sulfonate or phosphate groups, to reduce nonspecific binding. Phosphorylated soluble proteins, such as casein and its fragments, can be immobilized to provide a negatively-charged surface. To effect the immobilization, the proteins can first be thiolated, for example, by 3-(2-pyridyldithio)propionic acid N-hydroxysuccinimide ester (SPDP) and then attached either on gold or on a plastic surface via thiol group. Alternatively, proteins can simply be adsorbed on surfaces due to hydrophobic interaction. Adsorption is best done at the isoelectric point (for human IgG, pH=7.8) or slightly higher pH of the protein. In order to mask charges during adsorption, the salt concentration should be at least 100 mM NaCl. Increased temperature and mixing favors adsorption. If the protein being adsorbed is to function not only to reduce nonspecific binding, but also for other purposes, such is the case when primary or auxiliary recognition molecules are adsorbed, too high a temperature is of course detrimental, as it may lead to denaturation. For similar reasons, high detergent concentration should be avoided, because they solubilize proteins. However, for the same reason, detergents are favored during the assay, because they diminish nonspecific binding. For this reason the covalent binding of proteins is preferred so that detergents can be used in the actual assay.

Coating the assay device surface, or portions thereof, with proteins offers the additional advantage of presenting, via the protein's many functional groups, further opportunities for coupling molecules to the surface of the device. Thus, proteins often have several reactive aliphatic amino groups that are amenable to cross-linking. Similarly, carboxylic or thiol groups can be further derivatized. The carbohydrates presented by glycoproteins can be oxidized and the aldehydo groups coupled with amino groups in the presence of reducing agent. Several other coupling chemistries are well known in the art. Avidin-biotin or streptavidin-biotin interaction is very well known and routinely used in immuno- and other assays.

In yet another approach, adsorption or coupling of specific antibodies onto the assay device signal detection surface allows specific localization of other molecules onto these sites by using antigen conjugates.

Detergents can be used as surface-modifying agents. In particular, detergents originally designed and tested for their ability to solubilize biomolecules may be used. Examples of detergent classes and detergents that can be used for the surface treatment and solubilization include, but are not limited to

| | |
|---|---|
| Anionic | Linear alkylbenzene sulfonate |
| | Alkyl sulfates |
| | α-Olefin sulfonates |
| | Alcohol ether sulfates |
| | Sulfosuccinates |
| | Phosphate esters |
| | Fatty acid salts |
| | Perfluorocarboxylic acid salts |
| | Abietic acid |
| Cationic | Cetyl trimethylammonium bromide |
| | Alkylated pyridium salts |
| Zwitterionic | Alkyl betaine |
| Neutral | Alkyl phenol PEG |
| | Alkyl PEG |
| | Alkanolamides |
| | Glycol and Glycerol esters |
| | Propylene glycol esters |
| | Sorbitan and PEG sorbitan esters |
| | Polydimethylsiloxan PEG |
| Amphoteric | Dodecyl dimethyl amine oxide |
| Polymeric | Polyacrylic acid |

Particularly useful are nonionic Tween 20 and Triton X-100.

Other methods for the derivatization of the surface of the assay device include spreading of liquid-crystals and deposition of Langmuir-Blodgett (LB) films. LB-films can consist of only one monolayer or hundreds of layers. The surface layer can be hydrophobic or hydrophilic depending on the deposition cycle.

5.3 Synthesis of Cleavable Spacers

The two essential features of the cleavable spacers used in the cleavable signal element embodiments of the present invention are (1) a water soluble backbone, typically polymeric, and (2) at least one cleavage site. As noted at several places herein, analyte-specific side members are often present, but may be unnecessary in some embodiments.

The water soluble backbone typically will consist of a polymer, such as polyethylene glycol, polylactic acid, polyvinylalcohol, dextran, oligonucleotide, or polypeptide. The backbone polymer may contain side groups, such as hydroxyls, amino groups, carboxylates, sulfonates, or phosphates to increase the solubility, or may include such charged groups within the backbone itself, as, for example, in the phosphodiester bonds of an oligonucleotide.

A wide variety of cleavage sites may be used. One common class, set forth below in Table 2, are sites subject to hydrolytic cleavage.

TABLE 2

Hydrolytically cleavable sites

| | Hydrolysis pH | |
|---|---|---|
| Cleavable site | Acidic | Basic |
| Alcohols, Ethers | | |
| Alkoxymethyl ether | 2–4 | |
| Bis(2-chloroethoxy)methyl ether | 2–6 | |
| Tetrahydropyranyl ether | 2–6 | |
| Tetrahydrothiopyranyl ether | 2–4 | |
| 4-Methoxytetrahydropyranyl ether | 2–6 | |
| 4-Methoxytetrahydrothiopyranyl ether | 2–6 | |
| Tetrahydrofuranyl ether | 4–6 | |
| Triphenylmethyl ether | 2–4 | |

TABLE 2-continued

Hydrolytically cleavable sites

| Cleavable site | Hydrolysis pH Acidic | Hydrolysis pH Basic |
|---|---|---|
| Methoxytriphenylmethyl ether | 2–6 | |
| Dimethoxytriphenylmethyl ether | 2–6 | |
| Trimethoxytriphenylmethyl ether | 4–6 | |
| α-Naphtyldiphenylmethyl ether | 2–4 | |
| Trimethylsilyl ether | 1–7 | 7–12 |
| Isopropyldimethylsilyl ether | 2–6 | 12 |
| t-Butyldimethylsilyl ether | 2–4 | 12 |
| Tribenzylsilyl ether | 2–4 | 12 |
| Triisopropylsilyl ether | 2–4 | 12 |
| Alcohols, Esters | | |
| Acyl ester | | 12 |
| α,α-Dichloroacyl esters | | 10–12 |
| α,α-Difluoroacyl esters | | 8.5–11 |
| Phenoxyacetate ester | | 8.5–11 |
| Benzoyl ester | | 10–12 |
| Carbonate | | 10–12 |
| Bis (α,α-dichloroalkyl)carbonate | | 8.5–11 |
| Bis (α,α-difluoroalkyl)carbonate | | 8.5–10 |
| p-Nitrophenyl carbonate | | 8.5–10 |
| Benzyl carbonate | | 10–12 |
| p-Nitrobenzyl carbonate | | 10–12 |
| S-Benzyl thiocarbonate | | 10–12 |
| 2,4-Dinitrophenylsulfenate ester | 1 | 10–12 |
| 1,2- and 1,3-Diols | | |
| Ethylidene acetal | 1–4 | |
| Acetonide | 1–4 | |
| Benzylidene acetal | 2–4 | |
| p-Methoxybenzylidene acetal | 2–6 | |
| Alkoxymethylene acetal | 4–6 | |
| Alkylmethoxymethylenedioxy derivative | 4–6 | |
| Cyclic boronates | 1–7 | 7–12 |
| Phenols and Catechols | | |
| Methoxymethyl ether | 1–4 | |
| Methylthiomethyl ether | 1–4 | |
| t-Butyl ether | 1 | |
| t-Butyldimethyl silyl ether | 2–6 | |
| Aryl alkyl ester | 1 | 10–12 |
| Aryl benzoate | 1 | 10–12 |
| Aryl 9-fluorene carboxylate | | 10–12 |
| Aryl alkyl carbonate | 2–4 | 10–12 |
| Aryl α,α-dichloroalkyl carbonate | | 8.5–11 |
| Aryl α,α-difluoroalkyl carbonate | | 8.5–10 |
| Aryl vinyl carbonate | | 10–12 |
| Aryl benzyl carbonate | | 10–12 |
| Acetonide | 1–4 | |
| Diphenylmethylenedioxy derivative | 2–4 | |
| Cyclic borate | 1 | 12 |
| Carbonyl groups | | |
| Dimethyl acetal | 1 | |
| Dimethyl ketal | 1 | |
| Bis(α,α-dichloroalkyl) acetal | 1 | |
| Bis(α,α-dichloroalkyl) ketal | 1 | |
| Bis(α,α-difluoroalkyl) acetal | 1 | |
| Bis(α,α-difluoroalkyl) ketal | 1 | |
| 1,3-Dioxane | 1 | |
| 5-Methylene-1,3-dioxane | 1 | |
| 5,5-Dibromo-1,3-dioxane | 1 | 10–12 |
| 1,3-Dioxolane | 1–4 | |
| 4-Bromomethyl-1,3-dioxolane | 1–4 | |
| 4-o-Nitrophenyl-1,3-dioxolane | 1–4 | |
| 1,3-Oxathiolane | 2–4 | |
| O-Trimethylsilyl cyanohydrin | 1–7 | 7–12 |
| O-Phenylthiomethyl oxime | 0–1 | |
| Bismethylenedioxy derivatives | 0–4 | |
| Carboxyl group | | |
| Alkoxymethyl ester | 1–4 | |
| Tetrahydropyranyl ester | 2–4 | 10–12 |
| Benzyloxymethyl ester | 1–4 | 12 |
| Phenacyl ester | | 10–12 |
| N-Phthalimidomethyl ester | | 8.5–10 |
| α,α-Dichloroalkyl ester | | 8.5–11 |
| α,α-Difluoroalkyl ester | | 8.5–10 |
| α-Haloalkyl ester | 0–1 | 10–12 |
| 2-(p-Toluenesulfonyl) ethyl ester | | 8.5–11 |
| α,α-Dimethylalkyl ester | 2–4 | |
| Cinnamyl ester | 1 | 10–12 |
| Benzyl ester | | 10–12 |
| Triphenylmethyl ester | 2–6 | 10–12 |
| Bis(o-nitrophenyl)methyl ester | | 10–12 |
| 9-Anthrylmethyl ester | 0–1 | |
| 2-(9,10-Dioxo)anthrylmethyl ester | | 10–12 |
| Piperonyl ester | 1 | |
| t-Butyldimethylsilyl ester | 4–6 | 8.5–10 |
| S-t-Bytyl ester | 0–1 | 13 |
| 2-Alkyl-1,3-oxazoline | 0–1 | 13 |
| N-7-Nitroindoylamide | | 10–12 |
| Alkylhydrazide | 0–1 | |
| N-Phenylhydrazide | 0–1 | |
| Thiol group | | |
| S-p-Alkoxybenzyl thioether | 0–1 | |
| S-2-Picolyl N-oxide thioether | 0–1 | |
| S-Triphenylmethyl thioether | 0–1 | |
| S-2,4-Dinitrophenyl thioether | 7 | 8.5–10 |
| S-α-Cyanoalkyl thioether | | 10–12 |
| S-2-Nitro-1-phenylethyl thioether | | 8.5–10 |
| S-Benzoyl thioester | | 8.5–11 |
| S-Ethyl disulfide | 7 | 8.5–10 |
| Amino groups | | |
| 2-(α,α-Dimethylalkylsilyl)ethyl carbamate | 1–4 | |
| α,α-Dimethylalkynyl carbamate | 1 | |
| α-Methyl-α-phenylethyl carbamate | 0–1 | |
| α-Methyl-α-(4-biphenylyl)ethyl carbamate | 1 | |
| α, α(-Dimethyl-β-haloalkyl carbamate | 0–1 | |
| α,α-Dimethyl-β-cyanoalkyl carbamate | | 8.5–11 |
| α,α-Dimethylalkyl carbamate | 0–4 | |
| Cyclobutyl carbamate | 0–1 | |
| 1-Methylcyclobutyl carbamate | 1–4 | |
| 1-Adamantyl carbamate | 1–4 | |
| Vinyl carbamate | 2–6 | |
| Allyl carbamate | 0–4 | |
| Cinnamyl carbamate | 0–4 | |
| 8-Quinolyl carbamate | 0–4 | 12 |
| 5-Benzisoxazolylmethyl carbamate | 0–1 | |
| Diphenylmethyl carbamate | 1–4 | |
| S-Benzyl carbamate | | 12 |
| N-(N'-Phenylaminothiocarbonyl) derivative | 0–1 | 12 |
| α,α-Dichloroacetyl amide | | 8.5–11 |
| α,α-Difluoroacetyl amide | | 8.5–10 |
| N-Benzoyl amide | 1 | 12 |
| N-Dithiasuccinoyl amide | | 10–12 |

The chemical groups set forth in Table 2 are Cleavable, at the indicated pH ranges, by reagents such as 1 M HCl (pH 1), 0.01 M HCl and 0.01–1 M AcOH (pH 2–4), 0.1 N H₃BO₃ and phosphate buffer (pH 4–6), 0.1 N NaHCO$_3$ and 0.1 M AcONa (pH 8.5–10), 0.1 N Na$_2$CO$_3$ and Ca(OH)$_2$ (pH 10–12) and 0.1–1 M NaOH (pH>12).

Table 3 sets forth another class of cleavage sites that will prove useful in the cleavable signal element embodiments of the present invention.

TABLE 3

Other chemically-cleavable moieties

| Type of cleavage | Cleavage agent |
|---|---|
| Oxidative cleavage | |
| Tetrahydrofuranyl ether | Organic peracids |
| Methoxytriphenylmethyl ether | Organic peracids |
| Hydroquinone diether | AgNO$_3$ |
| Allyl carbonate | KMnO$_4$ |
| Alkylmethyl hydrazones | H$_2$O$_2$; Organic peracids |
| S-2,4-Dinitrophenyl thioether | Organic peracids |
| 4,5-Diphenyl-3-oxazolin-2-one | Organic peracids |
| S-Benzyl carbamate | H$_2$O$_2$; Organic peracids |
| Boronates | H$_2$O$_2$; Organic peracids |
| Carbon-carbon double bond | OsO$_4$ + HIO$_4$ |
| 1,2-Diol | HIO$_4$ |
| Reductive cleavage | |
| Tetrahydrofuranyl ether | NaBH$_3$CN |
| 2,4-Dinitrophenylsulfenate ester | NaBH$_3$CN |
| Boronates | NaBH$_3$CN |
| Oxygen-oxygen bond | Electrochemical cleavage; NaBH$_3$CN |
| Sulfur-sulfur bond | Electrochemical cleavage; Thiols |
| Azobenzene | Electrochemical cleavage; NaBH$_3$CN; Zn + HCl |
| Ferrocene | Electrochemical cleavage |
| Photochemical cleavage | |
| Dinitrophenyl ether | |
| Ion bond dissociation | |
| Alkyl ammonium carboxylate | HCl; Formic acid; Citric acid; Na$_2$CO$_3$; Polyamines |
| Calsium di- or polycarboxylate | HCl; Formic acid; EDTA |
| Hydrogen bond dissociation | |
| Hybridized oligonucleotides | Urea; Chaotropic salts; Heat |
| Carboxylic dimer | pH > 6–7; Carboxylic acids |
| Coordination bond dissociation | |
| Histidine-Copper-Histidine | Alkyl amines; HCl; Organic acids |

As shown in table 3, a variety of reagents can be used to effect oxidative cleavage. These include osmium tetroxide, potassium permanganate, silver nitrate, sodium periodate, peracids, iodine and hydrogenperoxide. Furthermore, where the assay device substrate, such as an optical disk, is metal coated, electrochemical oxidation can be used. In this latter case, the cleavable group is positioned close to the metal surface. At the completion of incubation of the assay device with the sample, the metal is used as an anode.

Reductive cleavage can be accomplished chemically by (substituted) hydroquinone, sodiumcyanoborohydride, zinc, magnesium, or aluminium. Sodiumcyanoborohydride is often preferred, because it dissolves in water, has high reduction potential, and is relatively stable in water. Electrochemical reduction can be used analogously to electrochemical oxidation.

In some assay geometries, cleavage of the cleavable moiety may itself be used directly to signal presence of the desired analyte. In these cases, first and second side members are not required on the cleavable spacer, as specificity for analyte is conferred directly by the cleavage moiety itself. For example, a boronate group in the cleavable spacer may be used directly to signal the presence of hydrogen peroxide. If there is no hydrogen peroxide present in the sample, the spacers will remain intact. In the presence of the hydrogen peroxide, the spacers will be cleaved in a concentration dependent manner.

Because hydrogen peroxide is a side product of many enzymatic reactions, hydrogen peroxide-cleavable spacers find use in many assay geometries in which the analyte is the enzyme substrate. As further discussed elsewhere herein, FIG. 31 demonstrates an assay for ethanol in which hydrogen peroxide is used to signal ethanol presence.

Although Tables 2 and 3 present the cleavable moieties individually, several different cleavable groups may usefully be employed in one spacer. Furthermore, different areas on the assay device can have different cleavable groups that can be cleaved orthogonally. This allows independent cleavage of the spacers.

Tables 2 and 3 are exemplary, not exhaustive. The pH ranges and reactivities given in the tables refer specifically to the case in which the identified cleavage site or moiety is incorporated within a saturated aliphatic straight chain compound, for instance, an alkoxymethoxy group with aliphatic alcohol, such as decanol. The skilled artisan would understand that cleavage conditions will change predictably with changes in the backbone structure.

Furthermore, the reactivities can be adjusted, and the range of cleavage conditions expanded or altered, by addition of chemical moieties that affect the cleavage site. For example, the reactivity of an ester may be adjusted using chemical moieties on either its alcohol or carboxylic acid sides, or both, as shown in FIG. 27.

FIG. 27A shows an aliphatic spacer containing an ester group. On the alcohol side, between R, indicating further backbone, and the ester itself, is an n-pthalimidomethyl group. This group renders the ester readily cleaved. FIG. 27B shows the same spacer, but with an α, α difluoroacid moiety between R', indicating further backbone, and the ester itself. This acid also renders the ester more readily cleavable.

The n-pthalimidomethyl α,α-difluoroalkanoate of FIG. 27C combines the two. Accordingly, while separately these groups would give derivatives that are hydrolyzed between pH 8.5–10 (albeit slowly at pH 8.5), the combination will be hydrolyzed rapidly at pH 8.5.

Thus, tens of thousands, if not hundreds of thousands, of combinations that are useful in the cleavable signal element embodiments of the present invention can be created from the moieties described in Tables 2 and 3.

It will also be appreciated that the spacers may contain moieties that are hydrolytically cleavable by enzymes, rather than by inorganic chemical agents. Table 4 provides a nonexhaustive list of such moieties and their cleavage enzymes.

TABLE 4

Hydrolytic enzymes and their substrates

| Hydrolytic enzyme | Substrate |
|---|---|
| Lipases | |
| Lipase (pancreas) | Primary acyl bond in triglycerides (micelle or monolayer, pH 8.0, $Ca^{2+}$) |
| Lipase (castor oil) | pH 4.7 |
| Lipoprotein lipase | |
| Phospholipases | |
| Phospholipase $A_2$ | sn-2-Acyl bond in phospholipids (pH 8.9, $Ca^{2+}$) |
| Phospholipase C | Bond between glycerol and phosphate (pH 7.3, $Ca^{2+}$) |
| Phospholipase D | |
| Proteases | |
| Chymotrypsin(ogen) | Amides and esters of leucine, methionine, asparagine, glutamine, etc. |
| Clostripain | Arginine carbonyl |
| Collagenase | Collagen |
| (Pro)Elastase | Elastin, N-acyl-L-alanine 3-p-nitroanilide (pH 8.5) |
| Papain | Proteins, amides and esters (pH 6.5) |
| Lipases | |
| Pepsin(ogen) | Proteins, esters (pH 1.6) |
| Protease S | Aspartic or glutamic moieties in proteins (pH 6) |
| Protease K | Proteins, amides (pH 9) |
| Trypsin(ogen) | Lysine or arginine moieties in proteins (pH 8.1, $Ca^{2+}$) |
| Nucleases | |
| DNase I | Single chain and double stranded DNA (pH 5, $Mg^{2+}$) |
| DNase II | Single chain and double stranded DNA (pH 4.6, $Mg^{2+}$), p-nitrophenyl phosphodiesters (pH 5.7) |
| Rnase | RNA (pH 7.2) |
| RNase T1 | RNA between 3'-guanylic and adjacent nucleotides (pH 7.5) |
| Nuclease S1 | Single stranded DNA and RNA (pH 4.6) |
| Glycosidases | |
| β-Agarase | 1,3-linked β-D-galactopyranose and 1,4-linked 3,6-anhydro-α-L-galactopyranose (pH 6.0) |
| α-Amylase (pancreas) | α-1,4-linked D-glucose units (pH 6.8) |
| α-Amylase (malt) | α-1,4-Linked D-glucose units (pH 4.9) |
| Lipases | |
| β-Amylase (pancreas) | α-1,4-Linked D-glucose units (pH 4.8) |
| Cellulase | β-1,4-Linked D-glucose units (pH 5.0) |
| Dextranase | 1,6-α-glucosidic linkages (pH 6, optional activators $Co^{2+}$, $Cu^{2+}$, $Mn^{2-}$) |
| β-Galctosidase | β-D-Glactosides (pH 7.5, $Mg^{2+}$) |
| Mannosidase | |
| α-Glucosidase | α-D-Glucosides (pH 6.7) |
| β-Glucosidase | β-D-Glucosides (pH 5.0) |
| β-Glucuronidase | Glucuronides (pH 4.8) |
| Hyaluronidase | 1,4-linkages between 2-acetamido-2-deocy-β-D-glucose and D-glucose moieties (pH 5.3) |
| Lysozyme | β-1,4 bond between N-acetyl muramic acid and N-acetylglucosamine (pH 7.0) |
| Neuraminidase | Sialoyl glycoproteins (pH 5.0) |
| Esterases | |
| Cholesterol esterase | Sterol esters (pH 6.8, cholate) |

Enzymes can be used as a cleavage reagents by incorporating into the spacer a moiety that serves as the substrate for the given enzyme. For instance, a spacer can contain a single-stranded oligonucleotide segment, a suitable substrate for S1 nuclease. After incubation of an assay device containing such cleavable spacers with sample, S1 nuclease is added under conditions optimal to cleavage of single-stranded nucleic acid, thus cleaving the cleavable spacers.

If, in such circumstances, the cleavable spacer side members are also oligonucleotides, they too may be cleaved if not rendered double-stranded by contact with fully complementary nucleic acids in the sample itself.

For cleavage of spacers containing, as the cleavable moiety, the substrate for an enzyme, zymogens or proenzymes can be used instead of the active enzyme itself. Such zymogens or proenzymes may be covalently bound with the spacers or onto the assay device surface. After incubation with sample, an activator is added that activates the zymogen or the proenzyme, which then rapidly cleaves the cleavable spacer. Alternatively, active enzymes can be coupled with the spacer or the substrate in the presence of a reversible inhibitor. During the assay the inhibitor is washed away and the spacer will be cleaved.

In yet another alternative, the cleavable spacer may be used directly to detect enzymes in a sample. In this geometry, both the cleavage agent and analyte-specific side members are unnecessary: enzyme that is present in the sample will cleave all spacers that contain the enzyme's substrate. Optionally, the local concentration of enzyme may be increased near the spacer to facilitate cleavage: this may be done by disposing, adjacent to the relevant spacers, a structure that recognizes the desired enzyme, such as an antibody. The recognition molecule so positioned must not, of course, interfere with the enzymatic activity of the analyte.

Taking into account all possible variations in the spacer backbone and in the cleavable group, millions of different spacers can be designed and prepared according this invention. Such preparation is within the skill in the art.

FIGS. 5 and 6 present a representative cleavable spacer molecule with a siloxane cleavage site. Most of the spacer, termed the backbone, is poly(alkyleneglycol), e.g., polyethyleneglycol, having a molecular weight of 400–10,000, preferably 400–2000. Making reference to the nomenclature in FIG. 1, the backbone of the spacer has a first end 31 that is adapted to couple to a derivatized amine group present on surface 21 of substrate 20, and a second end 32, which is adapted to couple with surface 41 of metal microsphere 40 via a thio-linkage 51. The backbone includes a cleavage site 33 between the first end 31 and the second end 32 of spacer molecule 30. In addition, between end 31 and cleavage site 33 is a side member 34a, commonly constructed from an oligonucleotide, and between cleavage site 33 and end 32 is another side member 34b commonly constructed from an oligonucleotide. Alternatively, such side members may be peptides or other organic molecules. More than two side members can be provided, but it is only necessary that two members are capable of forming a connective, molecular loop around the cleavage site to bind the spacer molecule to the surface of the substrate after cleavage at the cleavage site. These side members can be attached to the spacer backbone by linkers, such as polyethylene glycol.

One mode of synthesis of the representative cleavable spacer molecule 30 illustrated in FIG. 5 is substantially and generally as follows. Chlorodimethylsilane is coupled unto both ends of a polyethyleneglycol molecule. The silane group incorporated into the molecule reacts in the presence of catalytic amounts of chloroplatinic acid within N-acryloyl serine. The hydroxyl groups of both serine moieties are to be used later in the synthesis for the construction of oligonucleotide side members. One hydroxyl group is first protected by a monomethoxytriphenylmethyl group and the product is purified by liquid chromatography. The other hydroxyl group is then protected with a pivaloyl or fluorenylmethyloxycarbonyl (FMOC) group. The serine carboxyl groups are coupled with amino terminated poly(ethyleneglycol). The amino group at the other end is further derivatized by 3-(2-pyridyldithio) propionic acid N-hydroxysuccinimide ester. The other amino group is not reacted but is free to react later with the derivatized substrate.

An alternative, but substantially similar, and more detailed description of the spacer molecule synthesis, is provided below in Example I.

Spontaneous hydrolysis of siloxane can be made slower by substituting one or more methylgroups with i-propyl or t-butyl groups. Several functional groups can be used to attach spacer side-elements. These include, but are not limited to: amino, thiol, aldehydo, keto, carboxylic, maleimido, and α-halogenoketo groups. Many of these must be protected during synthesis and fabrication by techniques well known in the art.

5.4 Attachment of Cleavable Spacers and Auxiliary Recognition Molecules to Substrate Each of the spacer molecules is attached at one end 31 to support surface 21, e.g. via an amide linkage. In order to attach the spacer molecules to the amino-activated substrate, glutaric anhydride is reacted with the amino groups to expose a carboxylate group, shown more particularly in FIGS. 7A and 7B. The carboxylate groups can be esterified with pentafluorophenol. The free amino group on the spacer molecule will couple with this active ester. The spacer molecules and their attachment at the discrete sites to the solid support surface 21 are shown particularly in FIG. 7C. At this stage in the fabrication, the hydroxyl groups remain protected. While the oligonucleotide side members could be pre-synthesized on the spacers prior to the attachment to the solid surface support 21, it is preferable that they be attached after the spacer molecule 30 is attached on the solid support.

The chemistry described above for coupling a spacer to the assay device substrate is but one example of the chemistries that may usefully be employed; there are innumerable modifications that would be within the skill in the art. Virtually any reaction that can serve unidirectionally to bond the spacer to the solid support substrate of the assay device can be used. The substrate surface may itself be chemically active, or it can be activated or made otherwise amenable for coupling chemistry by adsorbed molecules or particles, as is well known in the art.

Although the coupling of signal elements to the solid-support substrate of an assay device, especially the coupling of cleavable spacers, is particularly described, it should be recognized that other molecules may additionally be attached to the substrate surface to facilitate particular assays.

As mentioned above, for example, auxiliary recognition molecules may be disposed on the assay device in proximity to the signal elements, such as cleavable signal elements, in order to increase the Local concentration of analyte. The coupling chemistries are identical to those used to attach the spacer to these surfaces.

As would be recognized, any such disposition of auxiliary recognition molecules on the solid support substrate of the assay device must be done with attention to the location and concentration of analyte-specific signal elements. Generally, less than 20% of the surface of an assay device will be covered by the spheres. Were the auxiliary recognition molecules attached in a uniform density across the surface of the device, almost 80% of the recognition molecules on the substrate would be useless. In fact, such molecules would, by capturing analyte in locations where recognition cannot be signalled, interfere with detection. The latter problem can be alleviated by patterning the surface as is described separately.

Auxiliary recognition molecules may also be attached, for analogous purposes, to the surface of the signal responsive moiety of the spacer. As with attachment of such auxiliary recognition molecules to the solid support substrate of the assay disk, attention must be paid to the spatial pattern in which these molecules are disposed. In the case in which the signal responsive moiety is a gold sphere, for example, attachment of auxiliary recognition molecules on the surface distal to the attachment to the spacer would sequester recognized analyte away from the analyte-specific side members of the spacer.

To avoid unnecessary coverage on the spheres, plastic spheres may be used that are partially coated with gold. The auxiliary recognition molecules may be attached to the gold-coated surface using dative bonding of thiols, compelling the attachment of the auxiliary recognition molecules proximal to the attachment of the spacers themselves. Alternatively, these auxiliary recognition molecules can be attached to the uncoated plastic surface using several coupling chemistries, such as amino-carboxylate, amino-iodoacetyl, or biotin-avidin. In any case, the spacers and recognition molecules will be attached onto the same hemisphere as is desirable.

Yet another alternative method for attaching auxiliary recognition molecules allows the random patterning of the substrate and use of symmetrical signal responsive moieties, such as uniform microspheres, yet avoids disposing the auxiliary recognition molecules so as to frustrate productive binding of analyte. In this latter method, the auxiliary recognition molecules are attached to the substrate and/or signal responsive moieties with a photocleavable spacer. For example, the recognition molecule's spacer may contain a dinitrophenyl ether grouping. In this method, the entire solid support substrate and all signal responsive moieties are randomly coated, either in one step or more, with photocleavable auxiliary recognition molecules. Next the surface of the assay device is illuminated by UV-light in such orientation that the photoreactive spacers will be cleaved in places except beneath the spheres. There is no need for a complete cleavage. The purpose is only substantially to reduce the number of spacers in open areas that are not useful for the assay.

As further described below, the assay device substrate may be adapted to function as an optical waveguide in embodiments suitable for continuous monitoring. For such embodiments, plastic is presently preferred as a device substrate, with polycarbonate most preferred, but glass may also be used. If glass is used as substrate, signal elements may be attached as follows. The glass surface is first activated, i.e., silicon oxygen bonds are hydrolyzed by hot hydrochloric acid. Three building blocks are needed to create the spacer molecules directly on the surface of a glass waveguide substrate. First is 11-(chlorodimethylsilyl) undecanoic acid methylester that is coupled directly onto the surface by silicon oxygen bond. The methyl ester is hydrolyzed by a dilute base after the coupling to release the carboxylic group. Second is diamino polyethylene glycol (DAPEG) that is connected with the free carboxylic group on the surface by forming an amide bond. The excess of DAPEG will be washed away, and the free amino group will be allowed to react with 3(2-pyridyldithio)propionic acid N-hydroxysuccinimide ester ("SPDP") which is the third building block. Before attachment of the gold spheres the dithio group will be reduced with dithiothreitol. SPDP is commercially available. The length of DAPEG can be varied between 10 nm and 1000 nm.

5.5 Design and Attachment of Signal Responsive Moieties

One feature of the current invention is the detection of analyte-specific signals from analyte-specific signal elements disposed in a spatially-addressable fashion on an assay device substrate. In preferred embodiments, the signal elements are cleavable and the substrate is an optical disk. Accordingly, this invention provides methods, compositions and devices for attaching signal responsive moieties to spacer molecules, particularly cleavable spacer molecules, disposed in predetermined, spatially-addressable patterns on the surface of the assay device.

5.5.1 Gold Particles as Signal Responsive Moieties

In some preferred embodiments of the present invention, particles that reflect or scatter light are used as signal responsive moieties. a light reflecting and/or scattering particle is a molecule or a material that causes incident light to be reflected or scattered elastically, i.e., substantially without absorbing the light energy. Such light reflecting and/or scattering particles include, for example, metal particles, colloidal metal such as colloidal gold, colloidal non-metal labels such as colloidal selenium, dyed plastic particles made of latex, polystyrene, polymethylacrylate, polycarbonate or similar materials.

The size of such particles ranges from 1nm to 10 $\mu$m, preferably from 500 nm to 5 $\mu$m, and most preferably from 1 to 3 $\mu$m. The larger the particle, the greater the light scattering effect. As this will be true of both bound and bulk solution particles, however, background may also increase with particle size used for scatter signals.

Metal microspheres 1 nm to 10 $\mu$m (micrometers) in diameter, preferably 0.5–5 $\mu$m, most preferably 1–3$\mu$m in diameter, are presently preferred in the light reflecting/light scattering embodiment of the present invention. Metal spheres provide a convenient signal responsive moiety for detection of the presence of a cleaved, yet analyte-restrained, spacer molecule bound to the disk. Typical materials are gold, silver, nickel, chromium, platinum, copper, and the like, or alloys thereof, with gold being presently preferred. The metal spheres may be solid metal or may be formed of plastic, or glass beads or the like, upon which a coating of metal has been deposited. Similarly, the light-reflective metal surface may be deposited on a metal microsphere of different composition. Metal spheres may also be alloys or aggregates.

Gold spheres suitable for use in the cleavable reflective signal element and assay device of the present invention are readily available in varying diameters from Aldrich Chemical Company, British BioCell International, Nanoprobes, Inc., and others, ranging from 1 $\mu$m to and including 0.5 $\mu$m (500 nm)–5 $\mu$m in diameter. It is within the skill in the art to create gold spheres of lesser or greater diameter as needed in the present invention.

Much smaller spheres can be used advantageously when reading is performed with near field optical microscopy, UV-light, electron beam or scanning probe microscopy. Smaller spheres are preferred in these latter embodiments because more cleavable spacers can be discriminated in a given area of a substrate.

Although spherical particles are presently preferred, non-spherical particles are also useful for some embodiments.

In biological applications, the signal responsive moiety—particularly gold or latex microspheres—will preferably be coated with detergents or derivatized so that they have a surface charge. This is done to prevent the attachment of these particles nonspecifically with surfaces or with each other.

The presently preferred gold spheres bind directly to the thio group of the signal responsive end of the cleavable spacer, yielding a very strong bond.

After the oligonucleotide side arm synthesis is completed, as further described below, the pyridyldithio group present at the signal-responsive end of the spacer molecule 30 is reduced with dithioerythritol or the like. The reaction is very fast and quantitative, and the resulting reduced thio groups have a high affinity for gold. Thiol groups bind gold virtually irreversibly; the gold-sulfur bonding energy is 160 kJ/mole. Halo groups similarly have high affinity for gold. Accordingly, gold spheres are spread as a suspension in a liquid (e.g., distilled water) by adding the suspension to the surface of the solid support 21. The gold spheres will attach only to the sites covered by thio terminated spacers and will not attach to the remaining surface of the substrate. Furthermore, while the above embodiments of the invention have been described with a single metal sphere attached to the signal-responsive end of a single cleavable spacer, it should be appreciated that when gold is used in a preferred embodiment of the invention, thousands of spacers may bind one gold sphere, depending upon its diameter. It is estimated that one sphere of 1–3 $\mu$m may be bound by approximately 1,000–10,000 cleavable spacers.

As a result, the stringency of the assay wash may be adjusted, at any given rotational speed, by varying not only the diameter of the gold sphere, but also the relative density of cleavable spacers to gold spheres.

Accordingly, if virtually all spacers under a certain gold sphere are connected by complementary molecules, the binding is very strong. If the spacers are fixated only partially under a certain gold sphere, the sphere may remain or be removed depending on the radius of the sphere and the frequency of the rotation.

5.5.2 Other Light-Responsive Signal Responsive Moieties

In some other embodiments of the cleavable signal element and assay device of the present invention, a light-absorbing rather than light-reflective material can be used as a signal responsive moiety. In this embodiment, the absence of reflected light from an addressed location, rather than its presence, indicates the capture of analyte. The approach is analogous to, albeit somewhat different from, that used in recordable compact disks.

Although similar in concept and compatible with CD readers, information is recorded differently in a recordable compact disk (CD-R) as compared to the encoding of information via pits in a standard, pressed, CD. In CD-R, the data layer is separate from the polycarbonate substrate. The polycarbonate substrate instead has impressed upon it a continuous spiral groove as a reference alignment guide for the incident laser. An organic dye is used to form the data layer. Although cyanine was the first material used for these discs, a metal-stabilized cyanine compound is generally used instead of "raw" cyanine. An alternative material is phthalocyanine. One such metallophthalocyanine compound is described in U.S. Pat. No. 5,580,696.

In CD-R, the organic dye layer is sandwiched between the polycarbonate substrate and the metalized reflective layer, usually 24 carat gold, but alternatively silver, of the media. Information is recorded by a recording laser of appropriate preselected wavelength that selectively melts "pits" into the dye layer—rather than burning holes in the dye, it simply melts it slightly, causing it to become non-translucent so that the reading laser beam is refracted rather than reflected back to the reader's sensors, as by a physical pit in the standard pressed CD. As in a standard CD, a lacquer coating protects the information-bearing layers.

> a greater number of light-absorbing dyes may be used in this embodiment of the present invention than may be used in CD-R. Light absorbing dyes are any compounds that absorb energy from the electromagnetic spectrum, ideally at wavelength(s) that correspond to the wavelength(s) of the light source. As is known in the art, dyes generally consist of conjugated heterocyclic structures, exemplified by the following classes of dyes: azo dyes, diazo dyes, triazine dyes, food colorings or biological stains. Specific dyes include: Coomasie Brilliant Blue R-250 Dye (Biorad Labs, Richmond, Calif.); Reactive Red 2 (Sigma Chemical Company, St. Louis, Mo.), bromophenol blue (Sigma); xylene cyanol (Sigma); and phenolphthalein (Sigma). The Sigma-Aldrich Handbook of Stains, Dyes and Indicators by Floyd J. Green, published by Aldrich Chemical Company, Inc., (Milwaukee, Wis.) provides a wealth of data for other dyes. With these data, dyes with the appropriate light absorption properties can be selected to coincide with the wavelengths emitted by the light source.

In these embodiments, opaque dye-containing particles, rather than reflective particles, may be used as a light-responsive signal moiety, thereby reversing the phase of encoded information. The latex spheres may vary from 1–100 μm in diameter, preferably 10–90 μm in diameter, and are most preferably 10–50 μm in diameter. The dye will prevent reflection of laser light from the metallic layer of the disk substrate.

In yet other embodiments, the signal responsive element may be a fluorescer, that is, an agent capable of fluorescing, such as fluorescein, propidium iodide, phycoerythrin, allophycocyanin, Cy-Dyes®, or may be a chemiluminescer, such as luciferin, high responds to incident light, or an indicator enzyme that cleaves soluble fluorescent substrates into insoluble form. Other fluorescent dyes useful in this embodiment include texas red, rhodamine, green fluorescent protein, and the like. Fluorescent dyes will prove particularly useful when blue lasers become widely available.

Direct fluorescence and luminescence measurements can be performed using detectors and techniques known in the art.

The cleavable spacer embodiments of the present invention permit, inter alia, fluorescer-quencher and donor fluorescer-acceptor fluorescer pairs. If these are bound together by the analyte, no fluorescence is observed in the former case, while acceptor fluorescence is observed in the second case.

In one possible luminescence approach, an enzyme, such as luciferase, is bound to a first side member of the spacer or is bound directly to the assay device substrate in proximity thereto. Luciferin, the enzyme substrate, is attached to a second side member of the spacer, or is sequestered, as in a liposome. If there is no binding of biomolecules, the substrate is removed (alternatively the enzyme). In the case of the binding, a strong luminescence is observed after the suitable chemicals, such as ATP and lysing or pore forming agents, have been added.

Dye deposition may also be used, for detection spectrophotometrically. In these approaches, almost any water insoluble dye can be rendered soluble by attaching polar groups, such as phosphate or glucose. The solubilizing groups can be hydrolyzed enzymatically and the corresponding dye deposited.

The light-reflective, light-scattering, and light-absorptive embodiments of the current invention preferentially employ a circular assay device as the substrate for the patterned deposition of cleavable signal elements. In an especially preferred embodiment, the assay device is compatible with existing optical disk readers, such as a compact disk (CD) reader or a digital video disk (DVD) reader, and is therefore preferentially a disk of about 120 mm in diameter and about 1.2 mm in thickness. By disk is also intended an annulus.

It will be appreciated, however, that the cleavable reflective signal elements of the present invention may be deposited in spatially addressable patterns on substrates that are not circular and essentially planar, and that such assay devices are necessarily read with detectors suitably adapted to the substrate's shape.

The maximum number of cleavable signal elements, or biobits, that can be spatially discriminated on a optical disk is a function of the wavelength and the numerical aperture of the objective lens. One known way to increase memory capacity in all sorts of optical memory disks, such as CD-ROMs, WORM (Write Once Read Many) disks, and magneto-optical disks, is to decrease the wavelength of the light emitted by the diode laser which illuminates the data tracks of the optical memory disk. Smaller wavelength permits discrimination of smaller data spots on the disk, that is, higher resolution, and thus enhanced data densities. Current CD-ROMs employ a laser with wavelength of 780 nanometers (nm). Current DVD readers employ a laser with wavelength between 635 and 650 nm. New diode lasers which emit, for example, blue light (around 481 nm) would increase the number of signal elements that could be spatially addressed on a single assay device disk of the present invention. Another way to achieve blue radiation is by frequency doubling of infrared laser by non-linear optical material.

Current CD-ROM readers employ both reflection reading and transmission reading. Both data access methods are compatible with the current invention. Gold particles are especially suitable for use as a signal responsive moiety for reflection type CD-ROM readers. Light absorbing dyes are more suitable for transmission type readers such as the ones discussed in U.S. Pat. No. 4,037,257.

5.5.3 Other Signal Responsive Moieties

It will be apparent to those skilled in the art that signal responsive moieties suitable for adaptation to the cleavable spacer of the present invention are not limited to light-reflecting or light-absorbing metal particles or dyes. Suitable signal responsive moieties include, but are not limited to, any composition detectable by spectroscopic, photochemical, biochemical, immunochemical, electrical, optical or chemical means. In some preferred embodiments, suitable signal responsive moieties include calorimetric labels such as colloidal gold or colored glass or plastic (e.g., polystyrene, polypropylene, latex, etc.) beads, biotin for staining with labeled streptavidin conjugate, magnetic beads (e.g., Dynabeads™), radiolabels (e.g., $^3$H, $^{125}$I, $^{35}$S $^{14}$C, or $^{32}$p), and enzymes (e.g., horse radish peroxidase, alkaline phosphatase and others commonly used in an ELISA).

It will be apparent to those skilled in the art that numerous variations of signal responsive moieties may be adapted to the cleavable spacers of the present invention. a number of patents, for example, provide an extensive teaching of a variety of techniques for producing detectible signals in biological assays. Such signal responsive moieties are generally suitable for use in some embodiments of the current inventions. As a non-limiting illustration, the following is a list of U.S. patents teach the several signal responsive moieties suitable for some embodiments of the current invention: U.S. Pat. Nos. 3,646,346, radioactive signal generating means; U.S. Pat. Nos. 3,654,090, 3,791,932 and U.S. Pat. No. 3,817,838, enzyme-linked signal generating means; U.S. Pat. No. 3,996,345, fluorescer-quencher related signal generating means; U.S. Pat. No. 4,062,733, fluorescer or enzyme signal generating means; U.S. Pat. No. 4,104,029, chemiluminescent signal generating means; U.S. Pat. No. 4,160,645, non-enzymatic catalyst generating means; U.S. Pat. No. 4,233,402, enzyme pair signal generating means; U.S. Pat. No. 4,287,300, enzyme anionic charge label. All above-cited U.S. patents are incorporated herein by reference for all purposes.

Other signal generating means are also known in the art, for example, U.S. Pat. Nos. 5,021,236 and 4,472,509, both incorporated herein by reference for all purposes. a metal chelate complex may be employed to attach signal generating means to the cleavable spacer molecules or to an antibody attached as a side member to the spacer molecule. Methods using an organic chelating agent such a DTPA attached to the antibody was disclosed in U.S. Pat. No. 4,472,509, incorporated herein by reference for all purposes.

In yet other embodiments, magnetic spheres may be used in place of reflective spheres and may be oriented by treating the disk with a magnetic field that is of sufficient strength. Since the empty sites will not have any magnetic material present, the location of the spacer molecules remaining can be detected and the information processed to identify the materials in the test sample. Additionally, reflective or magnetic material can be added after hybridization of the sample to provide the signal generating means.

Paramagnetic ions might be used as a signal generating means, for example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Colloidal gold label can be detected by measuring scattered light.

A preferred non-reflective signal generating means is biotin, which may be detected using an avidin or streptavidin compound. The use of such labels is well known to those of skill in the art and is described, for example, in U.S. Pat. Nos. 3,817,837; 3,850,752; 3,939,350; 3,996,345; 4,277,437; 4,275,149 and 4,366,241; each incorporated herein by reference for all purposes.

5.6 Attachment of the Cleavable Spacer Side Members

The side members of the cleavable spacers confer analyte specificity. In a preferred embodiment, the side members are oligonucleotides.

The oligonucleotides can be added by stepwise synthesis on the cleavable spacers prior to attachment of the spacers to the derivatized substrate of the assay device (disk). Alternatively, fully prepared oligonucleotides may be attached in single step directly to the spacer molecules prior to the spacer molecule's attachment to the assay device substrate. In such circumstances, the spacer molecule has protected amino- and/or thiol groups instead of two protected hydroxyl groups. One protective group is removed and an oligonucleotide that has, for example, an isocyanate group at one end is added. a second oligonucleotide is similarly attached as a second side member to the cleavable spacer molecule.

Alternatively, side member oligonucleotides can be synthesized after the attachment of the cleavable spacers onto the substrate, either in a single step using fully prepared oligonucleotides or by stepwise addition. The latter alternative is expected to be preferred when incorporating a large number of assays with different analyte specificity on a single assay device substrate. The general process by which the side members are attached to cleavable spacers previously immobilized on the substrate, whether in a single step or by stepwise addition, is herein termed stamping.

Phosphoramidite chemistry is preferred for preparing the oligonucleotide side members, although other chemistries can be used. In conventional solid phase synthesis, oligonucleotides are prepared by using monomeric phosphoramidites. After conventional synthesis, the oligonucleotides are then detached from he resinous support and purified by a liquid chromatograph to remove reactants, including solvents and unreacted mononucleotides, and to remove shorter oligonucleotides that result from incomplete synthesis. In certain instances the oligonucleotides cannot be so purified, and shorter oligonucleotides contaminate the desired oligonucleotide. This leads to unwanted hybridization. The oligonucleotide contaminants missing only one nucleotide relative to the desired product are the most difficult to deal with, because their binding is almost equal in strength to that of the oligonucleotide having the correct sequence.

In the preparation of oligonucleotides for use as side members in the cleavable reflective signal elements of the present invention, use of trimeric or tetrameric phosphoramidites in the synthesis is advantageous and preferred. Using tetrameric starting materials, for example, 12-mers can be synthesized in three steps. Unavoidable products of incomplete synthesis will in this instance be 8-mers and 4-mers, representing failure of 1 or 2 synthesis steps, respectively. Since the binding of 8-mers is much weaker than the binding of 12-mers, these contaminants do not cause any significant interference.

In applying side members to cleavable spacers by the stepwise addition to spacers immobilized on the surface of the assay device substrate, the oligonucleotides may advantageously be attached to the cleavable spacers by chemical printing, which utilizes the formation of the desired oligonucleotide chemical solution on a printed stamp that is complementary to the spacer molecule distribution on the solid support. Printing is rapid and economical. It can also provide very high resolution. a simple printing method is described, for example, in Science, Vol. 269, pgs. 664–665 (1995).

In this printing method, one of the protecting groups is removed from the spacer molecule on the assay device substrate. The desired oligonucleotides are applied to the stamp surface in a manner that will provide specific oligonucleotides at specific, predetermined locations on the stamp, and the stamp surface is then applied to the spacer-covered substrate support surface, thereby depositing the desired oligonucleotides in the discrete areas in which the spacer molecules reside. Subsequently, the second protecting group is removed and a different oligonucleotide is applied to the activated area, again by chemical stamping. Those steps are illustrated particularly in FIGS. 8A, 8B, 9A, 9B, 13 and 14.

Alternatively, the respective oligonucleotides can be applied by ink-jet printing, such as by methods described in U.S. Pat. Nos. 4,877,745 and 5,429,807, the disclosures of which are hereby incorporated by reference.

Either of these direct printing methods is rapid. When trimers or tetramers are used to build oligonucleotides, two printing cycles allows one to create an array of all possible oligos from 6-mers to 8-mers. To contain all 8-mers, the assay device must contain 256×256 different oligos. Additional printing cycles increase the length of oligonucleotides rapidly, although all combinations may not fit onto reasonably sized surfaces and several assay devices may have to be used to represent all such combinations.

Figure 15B:
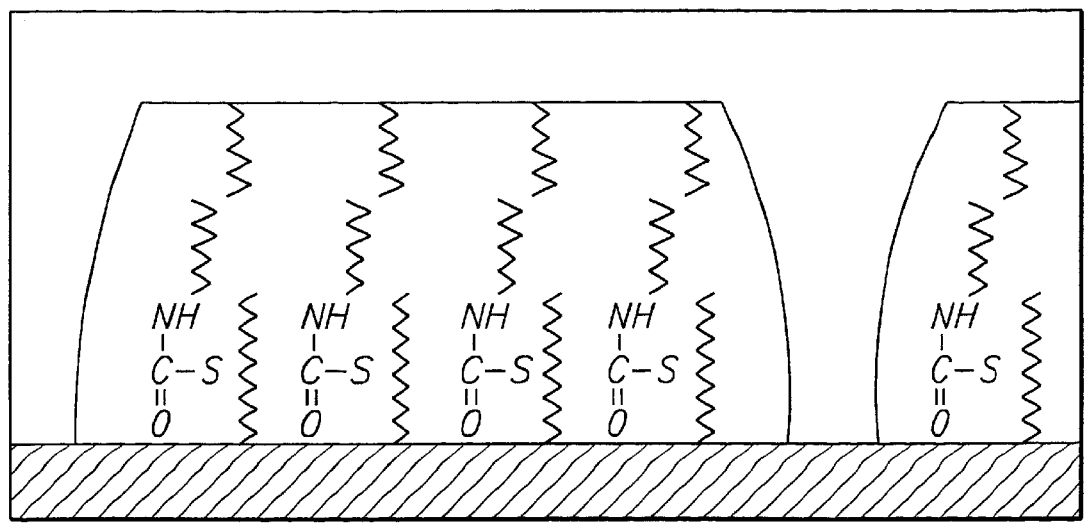

An alternative printing process useful in the present invention, concave complementary printing, is shown in FIG. 15. Although only two steps are shown, very large numbers of oligonucleotides can be printed at the same time. a mixture of oligonucleotides is synthesized; for example, 12-mers can be synthesized using a mixture of four phosphoramidites in each step, and as a last step of the synthesis, a very long spacer is attached to each oligonucleotide. On the other end a reactive group, such as an isothiocyanate, is provided. The mixture of oligonucleotides is incubated with the stamp that will bind complementary oligonucleotides at defined sites. During the printing process the spacer will attach with the substrate. The double helices are denatured, for example by heating, and the stamp and substrate can be separated.

Many other methods for the synthesis of oligonucleotides, and in particular, for spatially addressable synthesis of oligonucleotides on solid surfaces, have been developed and are known by those skilled in the art. Methods that prove particularly useful in the present invention are further described in U.S. Pat. Nos. 4,542,102; 5,384,261; 5,405,783; 5,412,087; 5,445,934; 5,489, 678; 5,510,270; 5,424, 186; 6,624,711; the disclosures of which are incorporated herein by reference.

Other methods that may prove useful in the present invention generally include: (1) Stepwise photochemical synthesis, (2) Stepwise jetchemical synthesis and (3) Fixation of pre-prepared oligonucleotides. Also a glass capillary array system can be used. In this latter case the synthesis can be performed parallel in all capillaries as is done in an automated DNA synthesizer.

Although the oligonucleotide side members have been described herein as DNA oligonucleotides synthesized using standard deoxyribonucleotide phosphoramidites, it is known that certain oligonucleotide analogs, such as pyranosyl-RNA (E. Szathmary, Nature 387:662–663 (1997)) and peptide nucleic acids, form stronger duplexes with higher fidelity than natural oligonucleotides. Accordingly, these artificial analogs may be used in the construction of oligonucleotide side members.

While the oligonucleotide side members are adapted to bind to complementary oligonucleotides, and are thus useful directly in a nucleic acid probe assay, it is a further aspect of the invention to conjugate to these oligonucleotide side members specific binding pair members with utility in other assays.

In these latter embodiments, the noncovalent attachment of binding pair members, such as antibodies, to side member oligonucleotides is mediated through complementarity of side member oligonucleotides and oligonucleotides that are covalently attached to the binding pair member. Use of complementary nucleic acid molecules to effectuate noncovalent, combinatorial assembly of supramolecular structures is described in further detail in co-owned and copending U.S. patent applications Ser. No. 08/332,514, filed Oct. 31, 1994, 08/424,874, filed Apr. 19, 1995, and 08/627,695, filed Mar. 29, 1996, incorporated herein by reference.

As schematized in FIGS. 3A through 3C, oligonucleotide side members 34a, 34b, 35a, and 35b are coupled noncovalently to modified antibodies 38a, 38b, 38c, and 38d to permit an immunoassay. The noncovalent attachment of modified antibodies to side members is mediated through complementarity of side member oligonucleotides and oligonucleotides that are covalently attached to the antibodies.

Although antibodies are exemplified in FIG. 3, it will be appreciated that antibody fragments and derivatives such as Fab fragments, single chain antibodies, chimeric antibodies and the like will also prove useful. In general, binding pair members useful in this embodiment will generally be first members of first and second specific binding pairs, exemplified by antibodies, receptors, etc. that will bind respectively to antigens, ligands, etc.

5.7 Patterned Deposition of Cleavable Reflective Signal Elements on the Assay Device It will be appreciated from the discussion above that the spatial distribution of analyte-responsive cleavable reflective signal elements on the assay device (disk substrate) may be determined at two levels: at the level of attaching the cleavable spacer itself, and additionally at the level of attaching the spacer side members. It will be further appreciated that the spatial distribution of analyte sensitivity may also be determined by a combination of the two.

One method for controlling the distribution of cleavable spacers in the first such step is through patterning the substrate with hydrophilic and hydrophobic domains. At first the hydrophobic surfaces are activated and the hydrophilic surfaces are deactivated so that a hydrophilic and functional spot array separated by a hydrophobic unreactive network is created. If the substrate material is glass, mica, silicon, hydrophilic plastic or analogous material, the whole surface is first rendered reactive by treatment with acid or base. The intermediate space between spots is silanized. This is best performed by using a grid as a stamp. If on the other hand the substrate is a hydrophobic plastic, it can be activated by plasma treatment in the presence of ammonia and then silanized as a hydrophilic substrate. Using resist material in conjunction with lithographic or mechanical printing to remove the resist at desired sites, activation can be performed at those sites.

Onto the reactive spots is preferably attached a hydrophilic spacer such as polyethyleneglycol (PEG). If the substrate contains an amino or a thiol group, PEG can be preactivated in the other end with a variety of functional groups, which are known to couple with an amino or thiol group. These include isocyanate, maleimide, halogenoacetyl and succinimidoester groups.

A photoresist may also profitably be used to pattern the deposition of cleavable signal elements. The resist is partially depolymerized by incident laser light during fabrication and can be dissolved from these areas. The exposed plastic or metalized plastic is treated chemically, for example, aminated by ammonia plasma. After the resist is removed, the spacer, side members, and signaling moiety are connected into the treated area as needed. The use of photoresists for the patterning of master disks is well known in the compact disk fabrication arts.

Alternatively, instead of using a resist, a solid mask containing small holes and other necessary features can be used during ammonia plasma treatment. Holes have a diameter of about 1 to 3 micrometers. The holes are located circularly in the mask, forming a spiral track or a pattern that is a combination of spiral and circular paths. The mask can be metal or plastic. Several metals, such as aluminum, nickel or gold can be used. Polycarbonate is a preferred plastic, because it will retain shape well. Plastics are reactive with the ammonia plasma, however, and a preferred method for using plastic masks therefore involves depositing a metal layer on the plastic, by evaporation, sputtering, or other methods known in the art. Holes may be made in the mask by laser. Those with skill in the art will appreciate that it is possible to create 1000 1 $\mu$m-sized holes in one second in a thin metal or plastic plate. Alternatively, the holes can be etched by using conventional methods known in the semiconductor industry. In the mask approach to patterning the deposition of signal elements, the mask is pressed against the substrate and the ammonia plasma applied. The mask may be used repeatedly.

As should appreciated, the spatial distribution of analyte sensitivity may also be conferred by the patterned application of spacer side arms.

With reference to the printing method above-described, the schematics of one possible oligonucleotide stamp is shown in FIG. 13. The stamp has holes which are filled with a certain chemical that will be used to provide the desired building block of the oligonucleotide being synthesized. In FIG. 13 each row is filled with the same chemical and accordingly four different chemicals can be used during one stamping cycle in the example given in FIG. 13. In commercial systems the number of rows will be considerably higher, typically 64–256, although lower and higher numbers of rows can be used in special cases. The linear stamp is advantageous if all possible oligonucleotides of certain size are to be fabricated onto the assay device substrate.

In this way all possible hexameric combinations of a given set of oligonucleotide building blocks can be prepared. For instance, trimer phosphoramidites can be formed by two reaction cycles by using a 64-row linear stamp. Each of the 64 different trimer phosphoramidites is fed into one row of holes. After printing the phosphoramidites, the oxidizer, deblocker and cap reagent are printed. As these chemicals are the same at each spot, the stamp can be a flat plate or the whole substrate can be simply dipped into the reagent solution. The substrate is rotated 90° and the same cycle is repeated. In this way all possible combinations of trimers have been fabricated. Analogously all combinations of any set of oligonucleotide amidites can be fabricated.

Figure 14B:
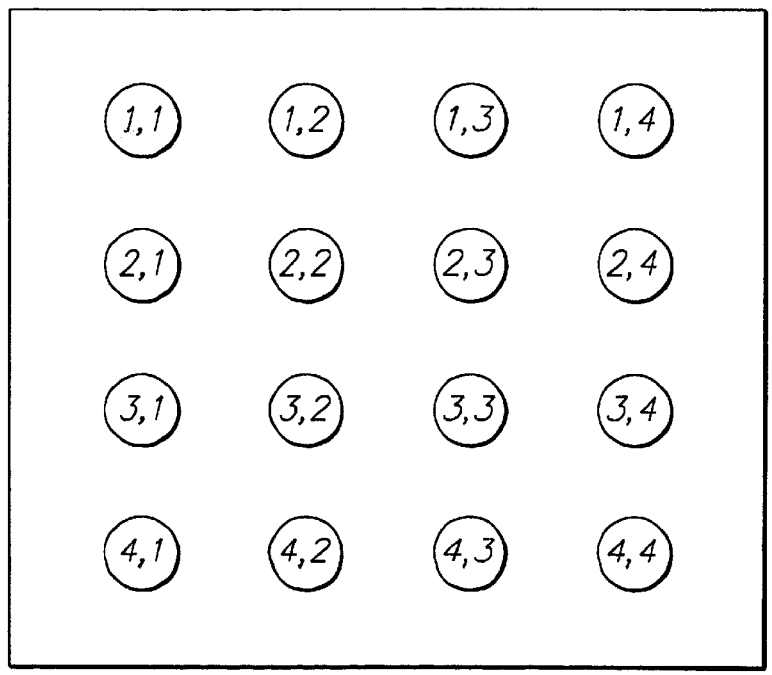

In FIG. 14 is an example showing the fabrication of all possible combinations of four different oligonucleotide amidites. After the first printing cycle all spots in each horizontal row contain the same oligonucleotide, but each row has a different oligonucleotide. These oligonucleotide fragments are denoted by numbers 1, 2, 3 and 4 in FIG. 14. When the stamp is rotated 90° and the printing cycle is repeated all combinations of four oligonucleotides are formed.

The foregoing orthogonal printing process is particularly advantageous in the production of signal elements of this invention in the embodiment of the disk. Orthogonal printing facilitates the distribution of the array of spacer molecules in a pattern of concentric circles, similar to the information that is placed onto audio or CD-ROM compact disks in annular patterns. One preferred variation of an orthogonal printing process employs superimposition of two sets of spiral stamps with opposite chirality.

The positioning of the stamp must be accurate within about 1 $\mu$m. This can be achieved mechanically using two to four guiding spike hole pairs or by an optoelectronically guided microtranslator. a removable reflective coating may be deposited onto two perpendicular sides of the substrate and the stamp and their relative positioning measured by an interferometer. The substrate and stamp can also have a pair of microprisms which must be perfectly aligned in order for the light pass into the photodetector.

FIGS. 11A through 11G illustrate various useful patterns of spatially addressable deposition of cleavable reflective signal elements on circular, planar disk substrates. FIG. 11A particularly identifies an address line, encodable on the disk substrate, from which the location of the cleavable spacers may be measured. In FIG. 11A, the cleavable spacer molecules are deposited in annular tracks. FIG. 11B demonstrates spiral deposition of cleavable signal elements, and particularly identifies a central void of the disk annulus particularly adapted to engage rotational drive means. FIG. 11C demonstrates deposition of cleavable signal elements in a pattern suitable for assay of multiple samples in parallel, with concurrent encoding of interpretive software on central tracks. FIG. 11D schematically represents an embodiment in which the assay device substrate has further been microfabricated to segregate the individual assay sectors, thereby permitting rotation of the assay device during sample addition without sample mixing.

FIG. 11E schematically represents an embodiment in which the assay device substrate has further been microfabricated to compel unidirectional sample flow during rotation of the assay device. Techniques for microfabricating solid surfaces are well known in the art, and are described particularly in U.S. Pat. Nos. 5,462,839; 5,112,134; 5,164,319; 5,278,048; 5,334,837; 5,345,213, which are incorporated herein by reference.

FIG. 11F demonstrates deposition of cleavable signal elements in a spatial organization suitable for assaying 20 samples for 50 different analytes each. FIG. 11G demonstrates the orthogonally intersecting pattern created by superimposition of spiral patterns with spiral arms of opposite direction or chirality.

The spatial distribution of cleavable reflective signal elements, or biobits, on the surface of the assay device may be designed to facilitate the quantitation of analyte concentration.

Thus, in some embodiments, analyte capture is used for quantification. In one implementation, the assay device is patterned with a uniform density of biobits dedicated to each chosen analyte. a test sample is introduced onto the disk in the center of the disk. By applying rotational force, the test sample is spread radially to the periphery. In the process of spreading, analytes are captured by the respective cognate side member of the cleavable signal element, reducing the concentration of analytes at the sample front.

With sufficient density of biobits relative to the incident concentration, all analytes are captured before the sample front reaches the periphery of the assay device. The concentration of each analyte may then be determined according to the location of the positive biobit that is farthest from the sample introduction site.

It will be appreciated that a greater dynamic range of analyte concentration will be detectable if more biobits are dedicated to the detected analyte. In the embodiment just described, the uniform density of biobits would be increased. It will further be appreciated, however, that the density of biobits need not be constant, and that a linear or exponentially changing density of biobits may be employed, as measured from the center of the disk to the periphery, to change the dynamic range of concentration detection.

In other embodiments and aspects of the present invention, biobits with different affinities for the chosen analyte may be attached to the assay device to similar effect, that is, to increase the dynamic range of concentration detection.

It is further contemplated that other geometries may be used to convey concentration information. FIG. 16 demonstrates one geometry in which a single sample is channeled in parallel into four distinct sectors of the assay device. If either the density of biobits, the affinity of the biobits, or both density and affinity of biobits in the four sectors differs, a large dynamic range of concentration may be determined by detecting the position in each sector of the positive biobit most distal from the sample application site.

In other embodiments, equilibrium assays are contemplated. Concentration is thus determined by sampling the entire disk and determining the percentage of positive biobits per analyte.

In each of these embodiments, generally a number of biobits are dedicated to detection of positive and negative controls.

In other embodiments, cleavable reflective signal elements (biobits) specific for multiple different analytes are patterned in a number of different formats. For example, biobits of distinct specificity are mixed in each sector of a disk. Alternatively, they may be separated into different sectors. The ability to pattern specific biobits into predefined locations and the ability to decipher the identity of biobits by detectors such as a CD-ROM reader makes flexible designs possible. One of skill in the art would appreciate that the design of patterns should be tested and adjusted using test samples containing known analytes of different concentrations.

5.8 Alternative Assay Device Geometries Without Cleavable Spacers

Although the use of cleavable spacers with analyte-specific first and second side members is preferred in many cases, alternatives exist that equally take advantage of optical disk readers for detection. Some of these alternatives are discussed in various other sections herein. Alternate geometries that dispense entirely with cleavable spacers are particularly discussed here.

5.8.1 Detection and Counting of Cells

Viruses are typically nearly spherical particles having diameter less than 0.5 $\mu$m. Bacteria are commonly either spherical or rod shaped; their largest dimension is usually less than 2 $\mu$m excluding flagella and other similar external fibers. These pathogens are somewhat smaller than, or about the same size as, the gold spheres used in the cleavable signal elements of the present invention. Their interaction simultaneously with two side members of the cleavable signal element above-described may, therefore, be sterically inhibited.

To detect such pathogens using the cleavable spacer embodiments presented hereinabove, the pathogens in the sample may be lysed, and the proteins and nucleic acid fragments identified as above-described. By detecting several components of the pathogens, the assay can be made highly reliable. However, the lysis and subsequent sample processing take several steps which require instrumentation and take time. Direct detection of cells would be advantageous.

Thus, an alternative geometry dispenses altogether with the cleavable spacers. One analyte-specific side member is attached directly to the substrate surface of the assay device in spatially addressable fashion. The second side member, specific for a second site of the chosen analyte, is attached directly to the signal responsive moiety. In preferred embodiments, that moiety is a gold sphere. In this alternative geometry, recognition of analyte creates a direct sandwich of the formula: substrate-first side member-analyte-second side member-signal responsive moiety. This geometry might be said to be a limiting case in which "m" in the formula for the cleavable spacer is zero.

For detecting *E. coli*, for instance, recognition structures, such as antibodies, may be used that are specific for flagellin. There are about 40,000 molecules of flagellin per flagella, and 0–100 flagella per cell. Flagellin is strikingly diverse among different bacterial species. Other proteins presenting attractive targets for detecting *E. coli* include fimbriae (common pili), F-pilus, OmpA, OmpC, OmpF.

This assay geometry is also useful for detecting, counting, and characterizing eukaryotic cells, that is, for assays in which eukaryotic cells are the analyte to be detected.

Cell counting has been traditionally been done by visual counting of stained cells under a microscope. Automated flow cytometry has, for many purposes, now supplanted or augmented manual inspection. See, e.g., M. G. Ormerod (ed.), *Cytometry: a Practical Approach*, 2d ed., Oxford University Press (1997); J. P. Robinson (ed.) and Z. Darzynkiewicz, *Handbook of Flow Cytometry Methods*, John Wiley & Sons(1993); a. L. Givan, *Cytometry: First Principles* John Wiley & Sons (1992), all of which are hereby incorporated by reference. In addition to the number of cells, automated flow cytometers further report the average size distribution of the cells.

Although they have not previously been so recognized or described, optical disk readers are, in essence, scanning confocal laser microscopes. As such, they can be used, with proper software, to study the detailed structure of biological and other specimens. Cell counting and cell shape measurement are two examples of these applications. FIG. 33 depicts one geometry, based upon this principle, useful for detecting eukaryotic cells.

The detection of eukaryotic cells in the present invention is best performed by attaching, directly to the device substrate surface, a first structure capable of recognizing and binding to the desired cells, such as an antibody. A second structure capable of recognizing and binding to the desired cells, such as a second antibody, is attached directly to the surface of a signal responsive moiety, such as a metal microsphere.

The first and second antibodies (or other recognition structures) may be identical, may be nonidentical but recognize the same protein, or may recognize different structures entirely. Use of distinct antibodies will increase specificity. It is also possible to use a mixture of antibodies, either for the first recognition structure, the second, or both, in order to broaden the detection to several cell types.

As is well recognized, cell surface proteins present particularly good targets for cellular recognition in assays. Extracellular matrix and adhesion proteins may also be used, either as targets or themselves as recognition molecules.

TABLE 5

Cell surface structures

Matrix proteins

MAG (myelin)
MUC18 (melanoma)
Selectins (carbohydrate binding proteins)
Restrictin (neural cells)
Serglycin (mast cells and other myeloid cells)
SPARC/Osteonectin (bone)
Syndecan (epithelial cells)
Tenascin (developing cells, tumor cells, neural and muscle cells)
Thrombospondin (inflammation)
von Willebrand Factor (platelet aggregation)

Selective cell-cell binding protein pairs

| Cell 1 protein | Cell 2 protein |
|---|---|
| GP Ib-IX (platelet) | vWF (platelet) |
| Integrin $\alpha 1\beta 1$ | Collagen, Laminin |
| ICAM-1 and ICAM-2 (endothelium, monocytes, lymphocytes) | LFA-1 (leukocytes) |
| L1 (neurons, Schwann cells) | L1 |
| LFA-5 or CD58 (monocytes, B lymphocytes) | CD2 (T lymphocytes) |
| MBP (hepatocyte) | mannose |
| NCAM (several cell types) | NCAM |
| PECAM-1 or CD31 (platelets, white and endothelial cells) | PECAM-1 |
| PH-20 Protein (sperm) | zona pellucidal protein |
| E-Selectin or ELAM-1 (endothelial cells) | NeuAc$\alpha$2, 3Gal$\beta$1, 4[Fuca1, 3] GlcNAc$\beta$1, 3Gal$\beta$-Carbohydr-Prot |
| TAG-1 (axons) | Integrins |
| VCAM-1 (endothelial cells) | Integrin VLA4 (lymphocytic and monocytic cells) |

To the above nonexhaustive list may be added, as particularly useful, antibodies to CD antigens that have been defined on the surface of immune system cells. Of particular interest in this regard is CD4, for purposes of following T helper counts in individuals with AIDS.

The sample can be any biological fluid, such as blood, saliva, semen, etc. Alternatively, the cells may be cultured, or from a gently homogenized tissue sample.

Prior to assay, certain cell types may be enriched or depleted, as by separation using magnetic beads (Miltenyi Biotec, Auburn, Calif.). In this case, signal responsive moieties, e.g., plastic beads, will already be attached to the cells of interest prior to addition to the assay device, and no other microspheres or other signal responsive moieties are needed on the disk at that specific assay site.

Furthermore, magnetic beads can be used to accelerate the binding of the cells onto the assay device surface. a pulsating and rotating magnetic field will allow the cell to contact, with high frequency, various assay sites at high frequency. Contact with the appropriate recognition structure will thereafter constrain movement. The frequency of pulsing can be 0.1–1,000,000 Hz.

Ultrasound is another way to accelerate the binding. Ultrasound will provide the energy for the high frequency movement of cells in the sample across the assay device substrate, but does not concentrate the sample at the interface. It is advantageous to use a static or pulsating magnetic field in conjunction with application of ultrasound.

By labeling the surface of cells relatively uniformly, their individual sizes and shapes can be measured by the optical disk drive functioning as a scanning confocal microscope. Many staining methods can be used. Cells can be coated by small latex or metal particles, or stained with immunogold silver stain, detection of which does not depend on the wavelength of the incident laser light (M. A. Hayat (ed.), *Immunogold Silver Staining*, CRC Press (1995)). Membrane-specific dyes allow the measurement of cell size, and, through intensity changes associated with the gradient of the membrane surface, permit reconstruction of the approximate topography of the cell.

But staining need not be limited to decoration of the surface by microspheres or other signal responsive moieties. For example, cells may be stained internally, so that they absorb enough laser light to prevent reflection from a reflective layer of the assay device. In yet another class of stains, the degree of staining correlates with some enzymatic activity, permitting study of the specific metabolic activity of the cells. An example is the nitroblue tetrazolium reduction test for neutrophil activity.

The confocal nature of the CD- or DVD-Drive also allows the study of thin tissue specimens. If only the side of the sample that is in contact with the assay device surface is stained, it will be preferentially detected, because the incident laser light is focussed into about micrometer sized spot in that plane. The part of the sample that is further removed from the surface will give only a weak diffuse background, because that part of the sample is not stained, and additionally because the light cone probes a relatively large area and all effects are averaged out.

This particular geometry, in which one analyte-specific moiety is attached directly to substrate and another is attached directly to the signal responsive element, may also prove useful in detecting nucleic acid hybridization, as shown in FIG. 17.

In this alternative geometry, if the signal responsive moiety is reflective, the information encoding is similar to that in the geometries presented earlier—the presence of analyte is signaled by reflection. Alternatively, if the signal responsive moiety is opaque, e.g. through incorporation of dye, the encoding is reversed: the presence of analyte is signaled by absence of reflection from the metallic layer of the device substrate.

Magnetic plastic spheres may provide particular advantages in this alternative geometry. Because they contain magnetic particles inside, they are less transparent than latex spheres. Furthermore, magnetism can be used to remove weakly bound spheres that are otherwise difficult to remove, as, e.g., latex spheres, because their density is close to that of water and centrifugal force would prove ineffectual.

A further variant of this alternative geometry takes advantage of agglutination in a reflection assay, as shown in FIG. 18. In this alternative, the signal responsive moieties are preferably microspheres. These microspheres are relatively small (30–600 nm), so that one alone does not block the light efficiently.

5.8.2 Detection of Aldehydes and Ketones

Chemical assays may also be adapted to detection using optical disk readers, without the use of cleavable spacers.

Aldehydes and ketones can be detected by immobilizing phenylhydrazine onto the detection surface of the assay device, preferably intermediated by a spacer molecule. If the assay device substrate is coated with gold, the spacer may be polyethylene glycol that has a thiol group at the end distal to that with the phenylhydrazine group.

The sample that contains an aldehyde or ketone is added. Hydrazone formation inactivates phenylhydrazine moieties to the extent that is proportional to the carbonyl concentration. Plastic spheres containing aldehyde groups (Bangs Laboratories, Inc., Indiana) are added. These plastic spheres will be bound covalently by the remaining phenylhydrazine moieties. The number of bound plastic spheres, as read by an optical disk reader, is inversely proportional to the concentration of an aldehyde or ketone.

5.9 Classification of Assay Geometries

As has been discussed and demonstrated hereinabove, virtually any analyte-specific assay may be adapted for use with the assay devices of the present invention. The sole requirement is that the assay's analyte-specific recognition be adapted to signal elements suitable for detection by an optical disk reader. Many of these assay methods are known, but their adaptation for detection using an optical disk-based reader is new.

Preferred embodiments of the assays of the present invention use the cleavable reflective signal elements of this invention. Others, however, dispense with the cleavable spacer side members, with specificity conferred by the cleavage site itself, while still others dispense entirely with cleavable spacers. Given the variety of assay geometries that may usefully be employed, a summary of those which prove particularly useful is presented here. The summary is illustrative, not exhaustive, and is not to be construed as limiting.

Assay methods, as adapted for use in the assay devices of the present invention, are schematized in FIGS. 34 and 35. FIG. 34 depicts assays without cleavable spacers; FIG. 35 depicts the corresponding assays with cleavable spacer. In these figures "R" and "S" represent the recognition molecules, whether disposed on cleavable spacer side members or not, and "X" and "Y" represent the analytes to be detected, or detectable moieties thereon. The signal-responsive moiety, suitable for detection in an optical disk reader, is shown as a sphere.

As has been discussed hereinabove, "R" and "X" represent cognate members of a specific binding pair, such as antibody-antigen, receptor-ligand, enzyme-substrate, enzyme-inhibitor, complementary oligonucleotides, or the like. Similarly, "S" and "Y" represent cognate members of a specific binding pair. For the chemical assays described above, the "specific binding pair" may alternatively represent chemical function groups with reactive specificity for one another.

FIG. 34A depicts a traditional "sandwich" assay. If "R" and "S" are antibodies, and "X" and "Y" are epitopes displayed by the analyte to be detected, this represents a sandwich immunoassay If "R" and "S" are oligonucleotides, and "X" and "Y" are complementary sequences on a nucleic acid to be detected, this represents a nucleic acid hybridization assay. In either case, the principle is clear: presence of the appropriate analyte in the sample serves to tether the signal responsive moiety to the assay device substrate, generating a detectable signal at that location.

The geometry also serves the converse purpose. Thus, if "R" and "S" are identical epitopes of an antigen, this geometry permits detection of an antibody that binds thereto.

FIG. 34B depicts a replacement assay. Recognition molecule "R" is attached to the signal responsive moiety. The analyte to be detected, or an analogue thereof, "X", is immobilized on the assay device substrate surface. Analyte present in the sample, shown as free "X", will displace the binding by the surface-immobilized "X", liberating the signal responsive moiety. The signal is lost at that location, the inverse of the signal direction in the first geometry, but equally informative.

FIG. 34C represents a competitive assay. It is analogous to replacement assay, but in this case the sample is mixed first with the recognition molecule-signal responsive moiety conjugate and it is this mixture that is added onto the substrate.

FIGS. 35A–C depict the incorporation of the cleavable spacer into the assays of FIGS. 34A–C. The spacer can be a single molecule, but it may also contain particles or a part of a bulk material, such as substrate plastic, rubber, glass, metal, or the like.

As detailed above, cleavable spacers offer several advantages in these latter geometries. First, all components are immobilized onto the assay site during manufacturing. Second, as a consequence of immobilization, less reagents are needed. Third, the kinetics are improved, because all components are maintained in close proximity to one another.

Several modifications of the schematized methods are readily apparent. For example, with reference to FIGS. 34B and 34C, the recognition molecule can be immobilized, while the analyte or its analog is conjugated with the signal responsive moiety. As would be recognized by those skilled in the assay arts, it is also possible to form various combinations of these assays. For example, even if the antigen is so small that the traditional "sandwich" assay is not feasible, a dimeric antigen, where "X" and "Y" are identical antigens, can be artificially prepared and be used in conjunction with a competitive assay (FIGS. 34C and 35C). The dimeric antigen is added together with the sample, and the univalent sample antigen prevents competitively the bridging by the dimeric antigen.

5.10 Continuous Monitoring Devices Incorporating An Optical Waveguide

It will be appreciated that each of the above-described assay device geometries is particularly suited for discontinuous, also termed static or batch, assay. That is, the obligatory cleavage step precludes repeated or continuous assay using the same cleavable signal elements. While physical segregation of cleavable spacers on the assay device, e.g. as exemplified in FIG. 11D, will permit multiple uses of the assay device itself, it remains true even in this geometry that each of the cleavable signal elements may be used only once to signal the presence or absence of analyte.

Another embodiment of the invention thus combines the cleavable signal elements above-described with an optical waveguide, thereby permitting repeated, or even continuous, monitoring for analyte. In another aspect, the continuous monitoring embodiment may be converted, after detection of analyte, to spatially-addressable static detection, as above-described.

The continuous monitoring assay devices profit from the ability to adapt the assay device substrate to serve as an optical waveguide. Incident light is directed into the device substrate via a radially disposed mirror integrated into the assay device itself; upon application of incident light, an evanescent wave propagates through the device substrate through internal reflectance. The presently preferred plastic compositions of the assay device substrate are particularly well suited for adaptation to serve as optical waveguides, although glass may also be used.

The internal reflectance of the evanescent wave is not total, however; light necessarily escapes the substrate. Escaping light interacts with the light-scattering or light-reflective signal moiety of attached signal elements; the light so scattered or so reflected may be measured.

The degree of interaction of the evanescent wave with a light-scattering or light-reflective signal moiety of an attached signal element will depend exponentially on the distance between the signal moiety (e.g., a gold microsphere) and the internally-reflective substrate; this distance, in turn, depends upon the differential presence or absence of the chosen analyte. With deposition of a plurality of signal elements, the intensity of the light scattered or reflected from the waveguide is strongly correlated with the concentration of the analyte.

In general, light will travel radially through the waveguide. To detect signaling events, the internally reflected light can be directed to exit the waveguide at a defined point, where the remaining luminescence may be assessed. Alternatively, since the light-scattering or reflective signal element moieties will also cause significant back scattering of the escaping light, the change in intensity of back scattered light may be measured. The intensity change in the back scattered light is much easier to detect than that of a forward light beam. Thus it might be advantageous to measure the back scattered light.

Optimization of the light-transmitting properties of the waveguide itself may include the deposition of cladding, or of partially reflective surfaces, on one or more surfaces, internal or external, of the waveguide; however, as described above, some leakage of light from the waveguide is essential for analyte detection. Such optimization is within the skill in the optical arts.

Although a mirror is preferred for directing incident light into the optical waveguide when visible or near infrared (NIR) radiation is used, prisms or diffraction gratings will also find use, especially for NIR or longer wavelength light. FIG. 26 demonstrates one embodiment in which uncollimated, but focused light, is first collimated into (nearly) parallel rays by a lens. The collimated beam is then directed by a prism to a diffraction grating integral to the assay device, then into the waveguide. The lens and prism may be in a modified detector, with the diffraction grating alone integrated into the substrate itself in lieu of a mirror.

The source of light for illuminating the waveguide may, in embodiments suitable for detection in CD-ROM or DVD readers, be the detector's in-built laser itself. Certain modifications of commercial laser-based detectors must be made, however, to ensure proper alignment.

The continuous monitoring principle may be better understood through reference to the figures. FIG. 19 shows a top view of an assay device of the present invention, as adapted for continuous monitoring. a radially disposed mirror directs incident light into the plane of the assay device substrate which is adapted to function as an optical waveguide. Also shown in FIG. 19 are circumferentially disposed sample application inlets for each of 20 spatially-segregated assay sectors. It will be appreciated that the assay device may also be constructed so that sample is applied more medially, nearer the mirror, so that rotation of the assay device drives sample toward the periphery through centrifugal force.

FIG. 20 shows further detail of the continuous monitoring assay device of FIG. 19, with FIG. 20A showing a top view of a single assay sector and FIG. 20B showing a side view. Particularly demonstrated are the spatially addressable assay sites, each containing a plurality of cleavable signal elements, the mirror, sample inlet port and a port for outflow, for outflow either of sample fluid or of sample gas (should sample be applied in the gaseous phase), and for outflow of air and other gases entrained in a liquid sample stream.

The side view shown in FIG. 20B further demonstrates a first assay device substrate 20 to which are attached cleavable signal elements, as in the static assay geometries described hereinabove. In the present example, substrate 20 is adapted for use as an optical waveguide. FIG. 20B also shows a second assay device substrate 53, substantially parallel to and separated from the first assay device substrate 20, and a gap therebetween, also termed a sample cavity, through which sample flows from sample inlet to outlet.

In preferred embodiments, the sample cavity is hydrophilic so that the wetting by liquid sample is perfect and no air bubbles are retained, and the total volume of the cavity is about 1–100 $\mu l$, preferably 10–50 $\mu l$, most preferably about 5 $\mu l$. Furthermore, it is preferred that the outlet be hydrophobic.

It will be appreciated that the total depth of the assay device may be adjusted—through adjustment of the width of substrate 20, adjustment of the width of substrate 53, and adjustment of the width of the sample cavity, as required by the requirements of the detection device. Thus, as set forth in Table 1 above, commercially available CD and DVD disks have a depth of 1.2 mm. Although a depth of 1.2 mm is most preferred for such disks, such detection devices will typically accommodate disks as wide as 2.4 mm. Thus, the continuous monitoring assay devices of the present invention will have a depth of 1.0–2.4 mm, preferably 1.2–2.0 mm, most preferably 1.2 mm.

In these embodiments, the assay device will preferentially be made of two disks of optically clear polycarbonate, each having a diameter of 120 mm, i.e., the same diameter as conventional CDS. During manufacture, the two disks will be assembled to form a hollow interior, and the resulting cavity may additionally be divided into sectors through which the liquid samples will flow. It will be appreciated, however, that other substrates, as described above, may also be used depending on their suitability for adaptation to function as optical waveguides. It will further be appreciated that the static assay geometries which do not use a substrate adapted for use as an optical waveguide may nonetheless also utilize a hollow interior geometry, and similar sample application techniques.

Plastic polycarbonate disks suitable for the optical waveguide embodiments may be purchased from Disk Manufacturing, Inc., Wilmington, Del. ("DMI"). The top disk will have a circular 45° tilted gold mirror evaporated near the center. The address information may simply be a zone of evaporated gold near the center. The mirror and address information may be deposited simultaneously.

FIG. 21 shows side views of an assay site with two signal elements during continuous monitoring for dimeric analytes.

FIG. 21A shows a first and a second cleavable reflective signal element attached to derivatized assay device substrate surface 21 of assay substrate 20. Assay substrate 20 is adapted for use as an optical waveguide. a first analyte-specific side member 34a is attached directly to the derivatized surface 21 of assay device substrate 20, and a second analyte-specific side member 34b is attached directly to the signal responsive moiety, a metal microsphere 40, of a first signal element. In this exemplification, the cleavable spacer does not itself contain side members. Also shown are a third side member 35a and fourth side member 35b, neither of which is specific for the chosen analyte; the second signal element thus cannot recognize the chosen analyte.

FIG. 21B demonstrates analyte-specific recognition by the first and second side members, 34a and 34b, tethering the first signal-responsive moiety to the substrate 20. This tethering is optionally assisted by application of centrifugal force, as shown. Also shown, side members 35a and 35b, which cannot recognize the chosen analyte, do not tether the second signal element to the substrate. Upon cessation of rotation of the assay device, only the first signal element is brought into proximity to the optical waveguide substrate, as shown in FIG. 21C.

In this proximal position, each bound gold sphere will give a reflective signal to waveguide light leakage; this, in turn, will alter the light intensity within the waveguide to a detectable degree. This change in light intensity may be registered by the detector, and will indicate the recognition of analyte by one of the signal elements.

FIG. 21D–21F shows a similar effect without application of centrifugal force. And in contrast to the dimeric analyte detected in FIGS. 21A–21C, the analyte itself contains a plurality of sites for attachment to the side members.

It is anticipated that the detector for assessing changes in waveguide transmittance in the continuous assay embodiments of this invention will have a more limited ability to discriminate the spatial location of signals than will the detector used for detection of reflection of the perpendicularly directed incident light. Thus, FIG. 22 demonstrates the combination of the spatially addressable, cleavable signal elements of the earlier-described static assay devices, with the continuous monitoring, optical waveguide geometry described here.

Once analyte is detected through change in the amount of light within the waveguide, or alternatively, through detecting a change in the amount of light escaping from the waveguide, the assay device may be exposed to a cleavage agent, as described for the static, or batch, devices. For siloxane-containing spacers, a solution of sodium fluoride, with concentration of 1 mM to 1 M, preferably 50 mM to 500 mM, most preferably 100 mM (0.1 M) will be used.

FIG. 22A demonstrates application of sodium fluoride as cleavage agent. FIGS. 22B and 22C demonstrate the differential signal provided after cleavage. As with the static, non-waveguide geometries, once cleavage has been performed, the cleaved signal elements (biobits) may not be used again.

It should be recognized that the hollow geometry is particularly suited for creation of physically segregated assay sectors, as, e.g., through interposition of interior walls. In this latter case, introduction of cleavage agent to one sector does not preclude subsequent continuous monitoring, and later cleavage, of other sectors on the same assay device.

The spatial discrimination of the waveguide detector will be sufficient, however, to identify whether signal emanates from any of the individually segregated assay sectors. The waveguide will indicate the sector where the detection occurred, and the one-to-one correspondence between sample and sector will identify the positive analyte-containing sample.

Subsequently, cleavage of cleavable spacers in that sector may be used to identify the nature and/or concentration of the analyte in the sample.

5.10.1 High Volume Screening of Drug Candidates

The continuous waveguide geometry is particularly well suited for high volume, rapid screening of drug candidates. The process provides both highly reliable and accurate results at a relatively low cost, and is particularly suitable for screening chemical libraries, prepared by either parallel synthesis or the split-and-mix method.

Although both parallel synthesis and split-and-mix chemical libraries can be screened by the continuous monitoring assay device (BCD), each will require a different design configuration within the BCD envelope. For parallel screening applications, the assay device (BCD) will contain upwards of 100 sectors, preferably more than 200 sectors, most preferably 200–400 sectors, with 400 sectors being presently the most preferred. For split-and-mix screening, the assay device will be sectored for each sublibrary; for example, screening of peptides will require 20 sectors in the BCD, corresponding to the 20 natural amino acids.

About 0.5 billion total Biobits will be fixated onto the waveguide disk during initial manufacture, and the total will be divided into radially oriented linear areas called assay sites. Each assay site will contain about 50,000 identical Biobits. Accordingly, one BCD will have 10,000 assay sites, which limits the number of assays per BCD to 10,000. The BCD will be further divided into identical sectors, and each sector will be used to study one sample.

It is to be noted that a sample may contain one compound (parallel synthesis), or one million compounds (split-and-mix synthesis). The number of assay sites in any one sector will set the upper limit for the number of target biomolecules. The practical upper limit for the number of sectors per BCD is approximately 400. Thus, in parallel screening, 400 compounds can be screened against 25 target biomolecules (400 sectors×25 target biomolecule=10,000 assay sites). In the split-and-mix protocol the number of samples will almost always be less than 25, and each sector can contain 400 target molecules. Because in this case each sample can contain up to one million compounds, 25 million compounds will be able to be screened simultaneously against 400 target biomolecules. For the sake of simplicity, FIG. 2 depicts a sector that has only 40 assay sites.

In high volume drug screening, analyte-specific side members will preferentially be disposed as shown in FIG. 21, rather than being disposed on either side of the spacer's cleavage site, as shown in FIG. 1, although the geometry shown in FIG. 1 remains feasible. As with the static assay elements and geometries, the side members may be single or double stranded DNA fragments, which are useful in the screening of gene-regulating agents; antibodies, antibody derivatives, or antibody fragments, to screen autoimmune disease or allergy drugs; enzymes, to screen for enzyme inhibitors; receptors, for screening for artificial ligands; and ligands, for screening for cognate receptors.

In many cases of drug screening, as well as in standard immunoassays, the analyte chosen for detection is a small organic molecule which can interact with only one cognate binding partner at time. These so-called univalent analytes are unable in the present invention to form the tethering loop required either (1) to secure the signal moiety in proximity to the optical waveguide, or (2) to secure the signal moiety to the substrate after addition of cleaving agent.

The problem of univalent small analytes has previously been addressed in development of standard immunoassays. Most of the existing strategies for solving this problem in standard immunoassays are readily adaptable to the novel cleavable signal element and waveguide assay device of the present invention. Therefore, only two particular strategies will be described here: (1) use of a replacement assay, and (2) use of dimeric or polymeric analyte candidates.

In the replacement assay, the tethering loop is premade using a surrogate ligand with modest affinity for the first and second side members. The surrogate ligand can be of biological origin, but preferably is a known artificial ligand, so that its binding affinity can be adjusted if necessary. The surrogate ligand will be suitable for binding simultaneously to both first and second side members. Each side member contains a receptor specific for the surrogate ligand and specific also for the chosen analyte. If the sample contains a higher affinity, univalent analyte for the same receptor, the sample analyte will replace the stationary surrogate ligand; since the sample analyte is univalent, the tethering loop is broken. If sufficient receptors are so blocked, the distance between the gold sphere and the waveguide will increase, thus changing the intensity of the light transmitted by the optical waveguide. Upon optional subsequent cleavage, such blocked receptors will be lost. In this approach, the drug candidates are in a soluble form and unlabeled.

Alternatively, the binding of dimeric or polymeric drug candidates can be measured. Dimeric molecules are able to bind two similar recognition molecules and will form a loop between a gold sphere and the waveguide. Two binding events will serve as a redundant check for good binding. Thus, nonspecific binding and a false signal due to impurities is largely eliminated. Although not ideal, the dimers more closely mimic actual drug molecules than do fluorescently labeled drug candidates in other, existing, approaches, since a fluorescent label may interfere with the binding process. The other half of the dimer is unlikely to do so any more than another similar molecule in close proximity.

In order to eliminate the effect of the spacer, several variants of the same drug candidates, connecting the spacer in different positions, should be synthesized. Actually, it is conceivable that some dimers might themselves serve as drugs, because they might induce dimerization of the receptors, which is an essential part of the natural function of single α-helix receptors.

When detection is done by the replacement method, there is virtually no restriction on the method used for synthesis of the chemical libraries. Chemicals are used as such and no labels are needed. However, when a binding assay is performed by the BCD, two or more similar molecules must be bound together.

Synthesis performed on a solid support automatically produces particles that have identical molecules connected onto their surfaces by a spacer. In parallel synthesis different types of particles are separated, and in split-and-mix synthesis several different types of particles are mixed. Importantly, in both cases a certain particle contains only one type of molecule on its surface (excluding impurities). Thus, these particles can be used directly in the binding assay on the BCD.

Often it is preferable that drug candidates not be bound onto large solid particles, but instead be soluble in the binding assay. Dimeric molecules can be conveniently prepared using a Y-shaped spacer. The spacer is singly connected with the solid support and synthesis is performed in both ends of the branches. The spacer is again cleavable, so that after completion of the synthesis it is cleaved near the intersection and the dimeric drug candidate is released for testing.

Four hundred assay sectors fit into one BCD. One chemical compound is tested in each assay sector. Accordingly, four hundred chemicals can be tested simultaneously in one BCD. As discussed earlier, in this case each assay sector can contain 25 assay sites. Each assay site is dedicated for a certain recognition molecule. Thus, four hundred compounds may be tested simultaneously against twenty-five recognition molecules; therefore, the total number of tests is 10, 000.

Split-And-Mix

Each drug candidate should have at least a 100 nM concentration in the first test, i.e., $3 \times 10^{11}$ molecules in 200 μl, which is a typical test volume in the split-and-mix assays. One million compounds would have a combined concentration of 10 mM. Average molecular weight of 400 D gives a total mass of 40 mg per milliliter. This is close to the upper limit before interference may be expected. Solubility of compounds might be limiting when the highest possible concentrations are used. The solvent is commonly water, although alcohol or some other biocompatible solvent may used in conjunction with water.

The following example is actually a hybrid of parallel and split-and-mix screening. The interaction of 25 biomolecules and all hexapeptides is measured. It is supposed that the BCD contains 10,000 assay sites. These are divided into 400 identical sectors of 25 assay sites each, corresponding to 25 different biomolecules. Thus, 400 different chemical libraries could be tested simultaneously against all 25 biomolecules.

There are 64 million different hexapeptides containing 20 of the most common amino acids. All hexapeptides are conveniently divided into 20 sublibraries so that each sublibrary has a certain known amino acid in a given position. For example, the last amino acid is alanine in one sublibrary, while other positions contain all combinations. In another sublibrary, the last amino acid is arginine, etc. This principle can be further expanded to produce 400 sublibraries as is explained in the following.

All hexapeptides can be synthesized in 400 groups so that, first, all possible tetrapeptides are synthesized in one column. Without detaching the tetrapeptides, the solid support is divided into 20 equal parts and a different amino acid is coupled with tetrapeptides in each of these baths. Pentapeptides are obtained in 20 sublibraries. Each of these sublibraries is further divided into 20 equal parts and again a different amino acid is coupled with pentapeptides in these baths giving a total of 400 sublibraries. In each of these cases, the last two amino acids are known while the first four vary freely (FIG. 25, where AA is an amino acid).

Each of the 400 sublibraries is injected into a dedicated sector in the BCD. The most interesting hexapeptides will be identified and one is selected for the next phase (denoted by a star in FIG. 25). At a later time, all can be studied in a similar manner. The last two amino acids of the lead candidate will be known. Next, the process is repeated so that the central two amino acids define 400 sublibraries. The last two amino acids are fixed by the result obtained in the first round. New testing will indicate the two central amino acids that give the best result. a third similar cycle will reveal all six amino acids in the most active hexapeptide.

Any library of chemicals can be studied in a similar manner. The mixtures could be made by combining smaller libraries into larger ones and storing samples of the intermediate ones. Alternative synthesis strategies can be used to create mixtures of millions of compounds. This is analogous to the hexapeptide example given above. In general, the starting materials and reactions can be any compatible combination.

The Biobit is able to detect any biomolecules for which recognition molecules are available. Oligonucleotides can be best recognized by complementary oligonucleotides. For example, to recognize a 22-mer oligonucleotide in the sample two 11-mer oligonucleotides can be used for the recognition. The other is complementary to 3'-end and the other to 5'-end of the sample oligonucleotide.

This is called (a,b)-recognition in general and in this special case it would be (11,11)-recognition.

Receptors, antibodies, enzymes, etc., can be used as recognition molecules. The molecules that interact with them, such as agonists, antagonists, antigens, inhibitors, etc., are herein collectively called ligands. The ligand may be naturally occurring compound, or it may be an existing drug. The purpose is to find a new compound that will bind so strongly with the biomolecule that the ligand will be replaced. In this case, the gold sphere will be lost when the spacer is cleaved.

In order to perform drug mass screening on the BCD, biomolecules must be attached onto some specific areas. This is accomplished by first conjugating a biomolecule with an oligonucleotide that is complementary with a stationary oligonucleotide on a given area. The recognition molecule-oligonucleotide conjugate will hybridize with the complementary oligonucleotide and the biomolecule is automatically located in the chosen area. The second recognition molecule is similarly attached onto each assay site. If a replacement assay is performed then the ligand of each biomolecule is similarly located on the same area.

Importantly, this method of attaching biomolecules onto the BCD is based on a self-assembly and can be performed by any ink-jet or automatic pipetting station. Thus, the operator will be able to use proprietary and other biomolecules in the assays while avoiding secret disclosure. The BCD can be provided as a blank platform where the operator will be able to attach all interesting biomolecules, or certain standard assays can be included in the production phase, while the operator will be able to add his own assays into the dedicated area as necessary.

5.10.2 Battlefield Bioanalyzer

The continuous waveguide geometry of the assay device of the present invention is also well suited for use under rigorous field conditions, and is particularly useful for use in portable instruments for continuous monitoring and analysis of environmental conditions. The solid state and essentially digital nature of the assay device finds particular utility under conditions of severe environmental stress, such as a battlefield. Thus, the continuous waveguide embodiments of the present invention are well suited for a battlefield analyzer, also termed herein a battlefield bioanalyzer. Such a device is useful for continuous monitoring of the battlefield atmospheric environment, and for rapid identification of a large spectrum of pathogens and toxins (Agents) which may be present, especially in conjunction with a sample collector that filters ambient air and solubilizes the resulting sample.

The BCD sample cavity will be sectored to provide space for detection of Agents.

During continuous monitoring, aqueous samples are pumped in a pulsating manner into the stationary BCD sample cavity through a detachable capillary plugged into the hollow interior via a central edge of the BCD. Each sample circulates for about 5 minutes, then exits through a second capillary near the inlet port, in a continuous manner for as long as monitoring is deemed necessary. Both capillaries will be coupled to the BCD during continuous monitoring, but decoupled when sample identification is needed.

The first sector of the BCD is the primary area for detecting an incoming Agent. It contains all possible Biobits for various Agents, i.e., it contains a plurality of signal elements with collective specificity for every one of the predicted spectrum of Agents for which monitoring is desired. Thus, continuous monitoring is possible without rotating the BCD.

If a threshold is exceeded in this first sector, indicating the presence of one or more Agents, the sample identification process is automatically triggered and performed within the same BCD. Other sectors will contain some subgroups of the Biobits spatially segregated so that the specific class of pathogen or toxin can be further identified.

It is to be noted that in the above manner, the waveguide will also be able to indicate a positive detection event in any sector of the BCD when the BCD is rotated.

After the computer has initiated the specific identification process, sodium fluoride (50 mM–100 mM) is pumped through the BCD inlet and outlet capillaries with the same pump as used for the monitoring samples. This solution will essentially cut the cleavable spacers holding the non-bound gold spheres to the waveguide substrate. The gold spheres are either flushed out of the BCD cavity or they will fall onto the bottom disk. In both cases they will give a zero signal. The cleavage will last only a few seconds. The CD-ROM laser will then "assay" the sample by reading perpendicularly through the waveguide disk and determining the exact number and location of all remaining gold spheres bound to the waveguide substrate. In this identification process, the CD-ROM computer will attach a value of one to all remaining bound spheres, while the absence of a sphere will have a zero value.

As the computer software will have been programmed to recognize the particular BCD sector in which each specific recognition biomolecule will have been placed, and which Agent will bind to each biomolecule, the computer will quickly identify the specific Agent present. Each Agent can be identified in various ways. For example, surface and core proteins of a virus can be identified, and some gene fragments can be identified. Individual viruses can easily be identified in ten different ways. This capability will increase reliability.

Final identification and quantification of the sample will be performed by perpendicular site-specific reading of the BCD.

The fastest way to identify biological warfare agents is to detect and identify whole pathogens, i.e., viruses, fungi and bacteria as such, using surface proteins as the chosen analyte for detection in immunoassays.

Direct detection of pathogens through immunoassay is a particularly favored assay for use in the battlefield bioanalyzer.

The instrument for the reading of the BCD is the computer with a CD-ROM. The sample will be collected and concentrated by a separate unit that will feed the sample into the CD-ROM through a tubing that must by retrofitted into a commercially available CD-ROM.

5.11 Sample Delivery Devices

General principles of sample delivery have been described hereinabove (section 5.1.7). Devices that facilitate such delivery are described in this section. Other variants will readily suggest themselves to those skilled in the assay arts. The following embodiments are thus illustrative, not exhaustive.

5.11.1 General Structural Features

Briefly, the sample delivery device and method of this invention utilize a multiwell plate, so dimensioned as conveniently to align in registration with the assay sites of the assay device. Where the assay device is fashioned as a disk, for example for reading in an optical disk reader, the multiwell plate is circular.

Because these multiwell plates are, in most applications, not used in the actual analysis, their manufacture is typically not constrained as to the optical quality of the material. In such cases the material can be plastic, metal or a combination of these, preferably but not limited to polyethylene, polypropylene, polyvinylchloride, polybutadiene, polytetrafluoroethylene or aluminum or some other metal coated with these plastics. However, if the sample application well plate is integral to the assay device, or is to be left approximated to the assay device during reading, the choice of the material is more stringent. If optical reading is performed through the well plate, it must be transparent and preferably non-fluorescent. Examples are polymethylacrylate, polycarbonate, polyvinylchloride, and cellulose acetate.

The multiwell plate can be single self-supporting structure or it can consist of several layers, most notably a rigid supporting structure and a thin, malleable, disposable film.

The sample aliquot can be brought into the contact with the chip or disk by rotating around the diagonal or normal of the plate. The rotation around the diagonal is 180° and the gravity will bring the aliquot onto the surface of the assay substrate. After the 180° rotation, a wagging motion can be maintained in order to increase the interaction between the aliquot and the assay site. When the rotation is around the surface normal utilized, the centrifugal force will bring the aliquot onto the assay site. In this case it is preferential to load sample, reagents and washing solutions into serially connected wells. a waste collection well is the last in the chain of wells.

5.11.2 Single Self-supporting Well Plate

FIG. 36 depicts a simple circular multiwell plate having 112 wells.

Diameter varies between 5 mm–500 mm, and thickness between 100 $\mu$m–100 mm. In a typical circular embodiment, each well has a diameter of 1 mm–50 mm and depth of 1 $\mu$m–50 mm. The plate has a thickness of 0.2–20 mm. In the present example, the plate is 1.5 mm thick and one well has diameter of about 5 mm and depth of 5 mm. The well is oval-shaped and hydrophilic, so that the liquid can easily flow when a the plate is rotated. The volume of the well is 125 $\mu$l, sufficient to hold a typical sample of 5–75 $\mu$l.

Each well delivers one sample onto one assay site of the assay device. As discussed hereinabove, each assay site may contain signal elements specific for a number of different analytes. Thus, these assay sites on the assay device are herein alternatively denominated panels, to denote, as in the clinical laboratory arts, that the set of analytes detected at that site is informative as to a potential diagnosis or condition.

The wells are arranged along 16 equally-spaced diagonals (FIGS. 36 and 37a). There are six or eight wells on each diagonal An eight tip pipetter can dispense samples simultaneously into each diagonal set of wells (FIG. 37B). The circular well plate can be rotated an angle of 90°/8 (=11° 15') between pipetting steps. Altogether, 16 pipetting steps are needed to fill all 112 wells.

The density of the wells can be increased by organizing the wells spirally. Then all nearest neighbor distances can be identical or nearly identical. In such a case, existing commercial pipetting stations must be modified accordingly.

When an assay device—also termed a bio-CD, biocompatible CD, or BCD—is apposed to the well plate, the air must get out; conversely, when the assay device is removed, the air return. In order to facilitate such air flow, the well plate may have a plurality of air holes (FIG. 38). Preferably, there is at least one air hole between each pair of wells (FIG. 38). Air holes are optionally present in the perimeter, where air access will occur nonetheless.

5.11.3. Capillary Well Plate

It may often be the case that the volume of each sample is so small that the sample forms only a film in a well. In such cases, gravity flow may be constrained.

FIG. 39 depicts a well plate that can be used for very small volumes. The well is the only hydrophilic part of the structure. Around the sample well is a shallow hydrophobic indentation. This can accommodate any excess sample when the well plate and BCD are compressed together. The bottom of the well communicates to another side of the plate via an air capillary. The sample cannot penetrate into this capillary, because it is very narrow and hydrophobic, yet this capillary provides replacement air, if there is so little sample that it cannot otherwise contact the surface.

5.11.4. Vacuum Well Plate

Although the cost of the sample well plates will be low, it might nonetheless be preferable to reduce the amount of disposables. This can be achieved by using a permanent well plate structure in which only the surface film is disposable, as shown in FIG. 41. The disposable film alone contacts the sample, permitting reuse of the well plate manifold.

The film can have a thickness between 10 $\mu$m–1 mm, and may be made of any elastic material. It may be secured over the surface using a supporting ring.

The wells of the reusable manifold are connected to a compartment that can be evacuated (FIG. 41). After the film is on the surface the valve that connects the well plate with a vacuum line is opened. While the air is removed from the wells the elastic film will tightly cover the wells (FIG. 41B and 41C). The valve can be closed and the vacuum line disconnected (FIG. 41D). Samples can now be pipetted (FIG. 41 E). After the samples have been incubated with the BCD (FIG. 41 F–H) and the BCD has been removed, the film can be removed. The film will form a bag that can be sealed and disposed (FIG. 41L). The well plate base itself is never in contact with any liquid and can be used repeatedly.

The same well plate base can also be used without a vacuum line (FIG. 42 A–E). After the film has been assembled onto the surface, the wells can be formed by a mechanical stamp. While the stamp is in the lower position, the valve is closed. Although there is no vacuum, the film must line the wells, because no replacement air can get underneath the film. The well plate can now be used as described earlier.

5.11.5. Centrifugal Well Plate

Instead of gravity, centrifugal force can be used to drive the liquid into contact with the BCD, if necessary, with force much greater than gravity. Axial rotation allows minimal instrument size. The drive of the optical disk detector may itself be used to accomplish this purpose.

In embodiments that contemplate centrifugal application of sample, it is possible to load sample, reagent and washing solutions simultaneously onto a centrifugal well plate (FIG. 43A–43E). During rotation these solutions pass the assay site or panel in the correct order. At the conclusion of the spin, the assay site may be covered by a buffer or by air, depending of the volumes of various liquids and the receiving reservoir. In either case the result can be read immediately, if the whole operation is performed inside an optical disk drive, reducing the assay to a single step.

5.11.6 Carousels and Jukeboxes

The multiwell sample application plate is placed in a rotation instrument manually or by a robot.

If the wells are protruding from the bottom, the support may have holes which can accommodate these protrusions. After the samples are in the wells, the BCD is placed on top of the well plate either manually or by a robot. Proper orientation and registration of the BCD is critical. The BCD can have mechanical and/or optical markings that make the correct registration possible during all steps. Mechanical slots or holes are preferred, because the system can be designed so that if these features are not aligned properly, the BCD is not leveled correctly, pipetting is physically impossible, and the system can alarm the operator. Alternatively, optical or electrooptical registration may be used, according to techniques known in the art.

The structure supporting the well plate can have features complementary to the slot(s) in the BCD. After the BCD is oriented properly it can be clamped together with the well plate from the edges of the perimeter and/or central hole. On top of the BCD there can be another supporting plate.

The structure supporting the well plate can contain active components, such as magnets. These magnets can coincide with assay panels on the assay device or with certain assay sites. In some assays, as described hereinabove, magnetic spheres are mixed with the sample, in which certain analyte (s) bind with these magnetic spheres. Subsequently, these magnetic spheres can be attracted onto the surface of the BCD by magnetic field. The binding kinetics will be greatly increased. The removal of extra spheres after the incubation can be greatly facilitated by an opposite magnetic field on the other side of the BCD.

5.11.7. Use of Sampling Well Plates in Clinical Laboratories

The assay devices and sample application well plates of this invention can be used in clinical medical laboratories and in other laboratories where multiple samples are analyzed.

In large clinical laboratories, samples are conventionally moved by means of conveyor belts. The system resembles railway network. Thus, samples that are intended for certain assays are diverted from the track onto a side track. Sample is placed first into a multiwell plate, and from there, in the present invention, applied to a BCD assay device that has an appropriate analyte-detection panel. All tests of that panel will be automatically performed, because that is easier and cheaper than excluding some assays at that point. But all tests need not be reported. In this sense the BCD is like a random access analyzer, which allows any combination of assays from a certain panel.

Pipetting of samples into multiwell plates is the rate-limiting step. Accordingly, several pipetting stations can be located along one sidetrack (FIG. 44). The multiwell disks should be maintained in constant humidity and temperature, preferably high humidity and low temperature, during pipetting. For example, the multiwell plate can be maintained in a temperature controlled box that has a slit or series of holes in the cover for the pipetting tips. The tips can always enter into the same place and the multiwell plate is horizontally rotated around the central axis. When all wells are full, the multiwell plate is transferred into another thermostated chamber that has relatively high temperature, typically physiological temperature, and high humidity (FIG. 44). The BCD is placed on the top of the multiwell plate and the samples are incubated on the top of the BCD. The BCD can be washed in the same chamber, dried by blowing warm air and read by CD- or DVD-drive.

The procedure is otherwise similar in small clinical laboratories and in hospitals, but these typically use test tube racks instead of conveyor belts. However, even small laboratories have pipetting robots and the process is basically the same as described above.

In field use, the samples must be often pipetted manually. Especially in this case it is preferable that the sample is put in always using the same fixed hole, with the disk rotating after each addition so that a new well is aligned below this hole.

5.11.8. Adding Reagents and Washing Solutions

The assay devices of the present invention, as intended for use in large clinical laboratories, contain multiple assay sites, each with signal elements specific for a plurality of analytes, termed a panel. Panels are generally configured so that the protocols are identical for each test in that panel, i.e., temperature, reaction time, reagents and washing solutions are the same. Thus, at one time only one reagent or washing solution is added onto the BCD. Accordingly, the same solution is added into all wells of the multiwell plate. a dispenser can be dedicated for each reagent and washing solution. This allows the continuous use of the same tips and tubing without any disposable parts.

The invention may be better understood by reference to the following examples, which are offered by way of illustration and not by way of limitation.

6. EXAMPLES 6.1 Example 1

Synthesis of a Spacer with Cleavable Siloxane Site

A representative cleavable spacer, shown schematically in FIG. 5, is synthesized as follows.

In brief, the synthesis is begun by constructing the central portion of the spacer molecule first. Both ends of the poly(ethyleneglycol) are then silanized, e.g. with chlorodimethylsilane to afford a compound of the formula of Compound I.

The silane groups then are derivatized with an alkenoic acid, straight or branched chain (e.g., $CH=CH(CH_2)_n COOH$, n=1–11, although the number of carbon atoms is immaterial, such as vinyl acetic acid, acrylic acid and the like) having a terminal double bond, such as vinyl acetic acid to form a compound having the structural formula of Compound II, and reacted further to provide a protected hydroxyl group on each side of the silane to provide for later attachment of oligonucleotides as illustrated by the compound having the structural formula of Compound III. Various common reactants can be used for this purpose, and N-acryloyl serine and TMT-serine methyl ester, when allowed to react in the presence of a catalyst such as chloroplatinic acid, are exemplifications of preferred reactants.

The resulting ester is partially hydrolyzed by the addition of an alkali metal hydroxide, such as sodium hydroxide, in an alcoholic solvent, and the adjacent protected hydroxyl group is preferentially hydrolyzed to yield a compound represented by the structural formula of Compound IV.

Amino terminated poly(ethyleneglycol) is derivatized at one end with a thio ester, such as 3-(2-pyridyldithio) propionic acid N-hydroxy succinimide ester, and coupled with Compound IV to yield a compound represented by the structural formula of Compound VI. The terminal ester group is hydrolyzed to yield the acid, which is further reacted with methoxyacetic acid, to afford the compound represented by the structural formula of Compound VIII. That compound is treated with aminated poly (ethyleneglycol) to form the completed spacer molecule substantially as illustrated in FIG. 5.

In detail, the synthesis is performed as follows:

Preparation 1: Compound I

To a mixture of poly(ethyleneglycol) (10 g, 10 mmol, av. MW 1,000 Aldrich Chemical Company) and triethylamine (TEA) (2.1 g, 21 mmol) in 100 ml of dichlormethane (DCM), is added dropwise 2.0 g of chlorodimethylsilane in 20 ml of DCM with cooling in an ice bath. After 10 minutes, the reaction mixture is filtered and the filtrate is applied into a 200 g silica column. The column is eluted with DCM/ MeOH 19:1, and the eluant affords poly(ethyleneglycol), di(dimethylsilyl) ether, the compound represented by the structural formula of Compound I.

Compound I

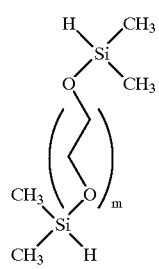

Preparation 2: Compound II

Compound I (10 g, 9 mmol) and vinylacetic acid (1.72 g, 20 mmol) is dissolved into 60 ml of ethyl acetate (EtOAc). A catalytic amount (40 mg) of chloroplatinic acid is added, and the mixture is heated to boiling and boiled for 1 hour. After cooling, the solution is applied directly into a 200 g. silica column. The column is eluted with EtOAc and EtOAc/MeOH 9:1, and the eluant affords poly(ethyleneglycol), di (2-carboxyethyldimethylsilyl) ether, the compound represented by the structural formula of Compound II.

Compound II

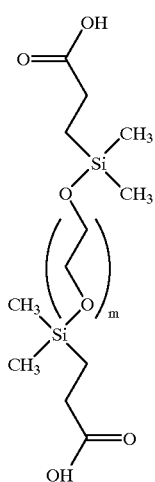

Preparation 3: Compound III

Compound II (9.5 g, 8 mmol) and trimethoxytrityl-serine methyl ester (7.0 g, 16 mmol) are dissolved into 100 ml of DCM. Dicyclohexylcarbodiimide (DCC) (3.25 g, 16 mmol) in 30 ml of DCM is added dropwise at room temperature. After 1 hour the reaction mixture is filtered. The filtrate is applied directly into 300 g silica column. The column is eluted with DCM/TEA 99:1 and then with DCM/MeOH/TEA 94:5:1. The eluant affords the compound represented by the structural formula of Compound III.

Compound III

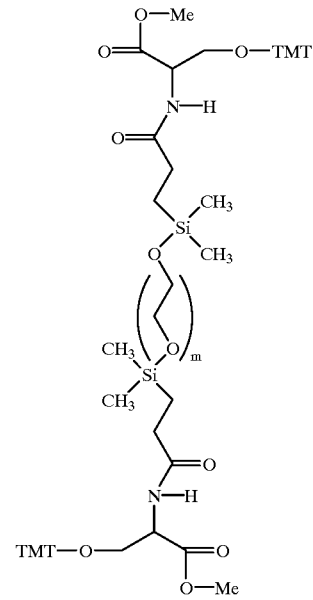

Preparation 4: Compound IV

Compound III (10 g, 5 mmol) is dissolved into 100 ml of EtOH and partially hydrolyzed by adding 10 ml 0.5 M NaOH in EtOH. The mixture is slightly acidified by adding 300 mg (5 mmol) acetic acid. The TMT-group proximal to the carboxylate group is preferentially hydrolyzed. After 30 min the mixture is made slightly basic by adding 0.5 ml tetraethylamine (TEA). The EtOH solution is fractionated by HPLC using a reverse phase column eluted with EtOH/Water/TEA 90:9:1. The eluant affords the compound represented by the structural formula of Compound IV.

Compound IV

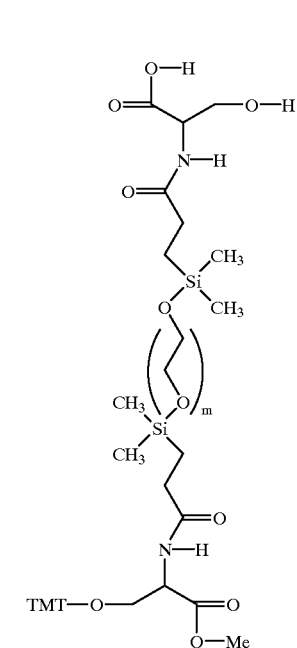

Preparation 5: Compound V

O,O'-Bis(aminopropyl)polyethyleneglycol (9.5 g, 5 mmol, av. MW 1900), triethylamine (0.5 g, 5 mmol) and 3-(2-pyridyldithio) propionic acid N-hydroxysuccinimide ester (0.77 g, 2.5 mmol) are dissolved into 150 ml of DCM. The mixture is stirred 1 hour at room temperature, concentrated into half volume and fractionated in 200 g silica column. The column is eluted with DCM/MeOH 95:5, to afford the compound represented by the structural formula of Compound V.

Compound V

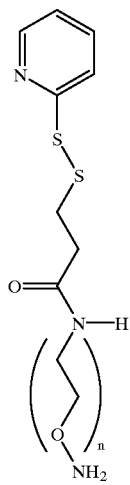

Preparation 6: Compound VI

Compound IV (3.5 g, 2 mmol) and Compound V (4.4 g, 2 mmol) are dissolved into 100 ml of DCM and 450 mg (2.2 mmol) DCC in 5 ml of DCM is added. After 1 hour the mixture is filtered, and fractionated in 150 g silica column. The column is eluted with DCM/MeOH/TEA 94/5/1, to afford the compound represented by the structural formula of Compound VI.

Compound VI

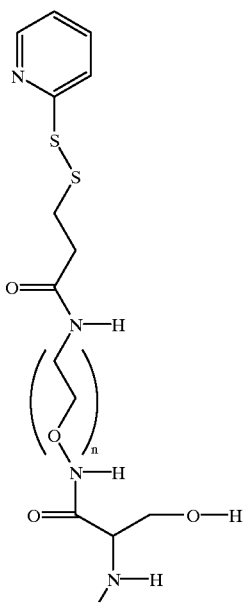

-continued

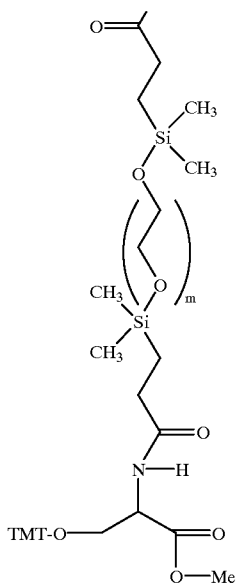

Preparation 7: Compound VII

Compound VI (6.0 g, 1.5 mmol) is dissolved into 50 ml of EtOH and 3 ml of 0.5 M NaOH in EtOH is added. After 30 min the product is purified by reverse phase HPLC using EtOH/water/TEA EtOH/Water/TEA 90:9:1 as an eluent, to afford the compound represented by the structural formula of Compound VII.

Compound VII

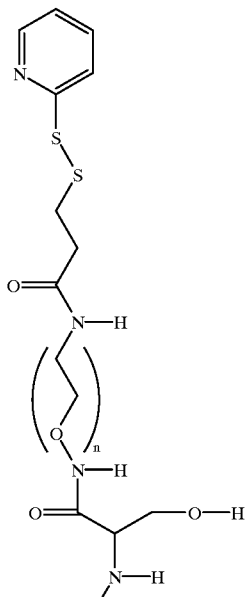

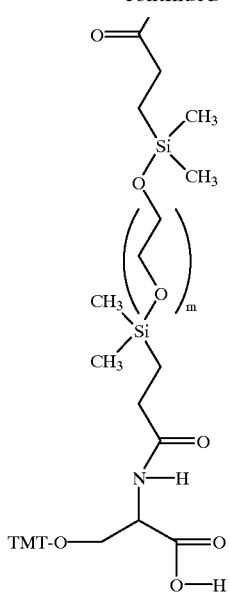

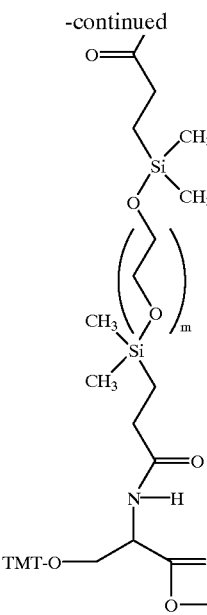

Preparation 8: Compound VIII

Compound VII (4.0 g, 1 mmol) is dissolved into 80 ml of DCM. The mixture of 320 mg (2 mmol) of methoxyacetic acid anhydride and 202 mg (2 mmol) of triethylamine in 5 ml of DCM is added. the mixture is evaporated by rotary evaporator into dryness. The residue is purified by reverse phase HPLC using EtOH/water/TEA EtOH/Water/TEA 90:9:1 as an eluent, to afford the compound represented by the structural formula of Compound VIII.

Preparation 9: Compound IX

Compound VIII (4.0 g, 1 mmol) and 0,0'-bis (aminopropyl)poly-ethyleneglycol (4.8 g, 2.5 mmol, av. MW 1900) are dissolved into 100 ml of DCM, 230 mg (1,1 mmol) DCC in 5 ml of DCM is added. After 1 hour the mixture is filtered and the mixture is fractionated in 100 g silica column using DCM/MeOH/TEA 94/5/1 as an eluent, to afford the compound represented by the structural formula of Compound IX, substantially as schematically represented in FIG. 5.

Compound VIII

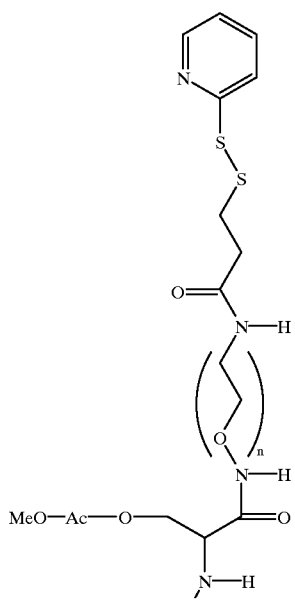

Compound IX

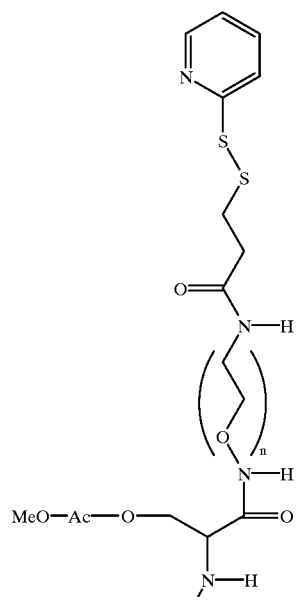

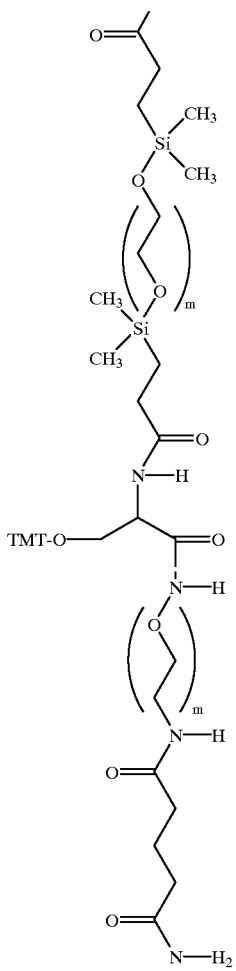

6.2 Example 2
Synthesis of a Cleavable Magnesium Dicarboxylate Spacer Recognizing Human IgG Onto a gold-coated polycarbonate disk is added by ink-jet printer 2 μl of 10 μM biotindisulfide water solution in 64 circular spots having a diameter of 5 mm. Onto these same spots is added by ink-jet printer 2 μl of a mixture of 1 μM streptavidin and 1 μM albumin.

Goat anti-human IgG (Bioprocessing, Inc., Scarborough, Me; Covalent Immunology, Monroe, N.H.) is reduced by thioethanolamine to produce univalent halves, each of which consists of one heavy chain and one light chain (HL). Thioethanolamine is removed by dialysis and maleimido-polyethyleneglycol-biotin (MAL-PEG-BIO; MW 3, 400, Shearwater Polymers, Inc., Alabama) is added. A small amount of thioethanolamine is added to render maleimido groups unreactive. The mixture is dialyzed against 10 mM phosphate buffer (pH 7) in a dialysis tube (molecular weight cut-off 30,000).

To this antibody derivative (Ab-PEG-BIO) is added a ten fold excess of BIO-PEG-carboxylic acid and a one hundred fold excess of BIO-PEG-OMe in 1 μM $MgCl_2$. Two (2) μl of this mixture is added, by ink jet printer, onto the spots previously printed on the assay disk. The disk is washed.

At this point, slightly fewer than 1% of streptavidin sites earlier-spotted on the disk display the goat anti-human antibody half (HL) at the end of a PEG spacer, somewhat fewer than 9% display carboxylic acid groups at the end of a PEG spacer, and about 90% display hydroxymethyl groups, which are inert in the present case.

Into a suspension of 10 mg streptavidin-coated latex beads (1micrometer in diameter) is added 0.1 mg of Ab-PEG-BIO, prepared as above-described, 0.1 mg of BIO-PEG-carboxylic acid and 1 mg of BIO-PEG-OMe in pH 7 phosphate buffer. The mixture is filtered through a 0.2 gm filter. As with the disk surface, the beads display analyte-specific groups (PEG-Ab), carboxylic acid groups, and carboxymethyl groups that are functionally inert in the assay.

The beads are suspended in distilled water and the suspension added uniformly onto the surface of the disk. The disk is shaken gently about one hour to permit adherence of beads through ionic bond formation between carboxylic acid groups displayed on the beads and carboxylic acid groups presented from the surface of the assay device. Extra beads are removed by gentle washing. The wash solution may contain a polyalcohol, such as glycerol, mannitol, starch or the like to stabilize proteins during the storage.

A sample containing human IgG is pipetted (10 μl) onto each assay spot. The assay device is incubated in a humidified incubator. Following incubation, the assay disk is washed with an excess of 25 mM phosphate buffer (pH 7) containing 100 mM sodium chloride.

Human IgG in the sample binds both to PEG-Ab that is directly adherent to the assay disk surface and to PEG-Ab displayed by beads tethered adjacent thereto by magnesium dicarboxylate groups.

The magnesium dicarboxylate groups are cleaved by addition of 10 μl 50 mM EDTA, which chelates magnesium. Latex spheres that have not bound human IgG are lost. Latex spheres that have bound human IgG that is additionally bound to surface adherent Ab, are retained. The unbound spheres are washed away with water. The disk is dried and read in an optical disk drive. The concentration of human IgG is proportional to the signal generated by the latex spheres.

6.3 Example 3
Detection of HIV-1 in a Nucleic Acid Assay

HIV-1 proviral DNA from clinical samples is amplified as follows, essentially as described in U.S. Pat. No. 5,599,662, incorporated herein by reference.

Peripheral blood monocytes are isolated by standard Ficoll-Hypaque density gradient methods. Following isolation of the cells, the DNA is extracted as described in Butcher and Spadoro, *Clin. Immunol. Newsletter* 12:73–76 (1992), incorporated herein by reference.

Polymerase chain reaction is performed in a 100 μl reaction volume, of which 50 μl is contributed by the sample. The reaction contains the following reagents at the following initial concentrations:

10 mM Tris-HCl (pH 8.4)
50 mM KCl
200 μM each DATP, dCTP, dGTP, and dUTP
25 pmoles of primer 1, of sequence shown below
25 pmoles of primer 2, of sequence shown below
3.0 mM $MgCl_2$
10% glycerol
2.0 units of Taq DNA polymerase (Perkin-Elmer)
2.0 units UNG (Perkin-Elmer)
Primer 1: 5'-TGA GAC ACC AGG AAT TAG ATA TCA GTA CAA TGT-3' (SEQ ID NO: 10)
Primer 2: 5'-CTA AAT CAG ATC CTA CAT ATA AGT CAT CCA GT-3' (SEQ ID NO: 11)

Amplification is carried out in a TC9600 DNA thermal cycler (Perkin Elmer, Norwal, Conn.) using the following temperature profile: (1) pre-incubation—50° C. for 2 minutes; (2) initial cycle—denature at 94° C. for 30 seconds, anneal at 50° C. for 30 seconds, extend at 72° C. for 30 seconds; (3) cycles 2 to 4—denature at 94° C. for 30 seconds, anneal for 30 seconds, extend at 72° C. for 30 seconds, with the annealing temperature increasing in 2° C. increments (to 58° C.) as compared to cycle 1; (4) cycles 5 to 39—denature at 90° C. for 30 seconds, anneal at 60° C. for 30 seconds, extend at 72° C. for 30 seconds.

Following the temperature cycling, the reaction mixture is heated to 90° C. for 2 minutes and diluted to 1 ml. Alternatively, the sample is stored at −20° C., and after thawing, heated to 90° C. for 2 minutes then diluted to 1 ml.

Cleavable spacers with siloxane moiety are synthesized and attached in a uniform density to a derivatized 120 mm polycarbonate disk substrate essentially as set forth in sections 5.2 and 5.3 and Example 1 hereinabove. The following side members are then stamped on the cleavable spacers:

first side member: 5'-TAG ATA TCA GTA CAA-3' (SEQ. ID NO. 12)

second side member: 3'-TAT TCA GTA GGT ACA-5' (SEQ. ID NO. 13)

A suspension of gold microspheres, 1–3 $\mu$m in diameter, is added dropwise to the disk, which is gently rotated to distribute the gold particles. Gold particles are added until the effluent contains the same density of particles as the initial suspension, thus ensuring saturation of the cleavable spacers.

Sample is applied at room temperature dropwise near the center of the assay device which is rotated at a continuous speed Rotation is halted after the sample front reaches the periphery, and the disk is incubated stationary at room temperature for 3–5 minutes.

One ml of sample buffer is added dropwise as a wash while the disk is rotated. One ml of 100 mM sodium fluoride is added and distributed by disk rotation. The disk is incubated stationary for 1–2 minutes, then 5 ml of sample buffer is added dropwise during vigorous rotation of the assay disk.

The disk is dried, then read directly in a CD-ROM reader programmed to assay each predetermined site upon which cleavable spacers were deposited.

6.4 Example 4

Increased Specificity of a Nucleic Acid Hybridization Assay

In a direct nucleic acid hybridization assay, the side elements of the cleavable signal element are oligonucleotides designed to hybridize with distinct sites on a chosen, predetermined, nucleic acid to be detected in the sample. For many applications of this methodology, cross-reactivity with sample oligonucleotides having even a single mismatched nucleotide should be minimized. In particular, nucleic acid hybridization assays adapted to use the cleavable reflective signal element of the present invention for detection of point mutations, as, e.g., for detection of point mutations in the BRCA1 and BRCA2 genes that predispose to breast and ovarian cancers, must be able to discriminate as between nucleic acid samples containing a single mismatched nucleotide.

The longer the oligonucleotide side elements of the cleavable signal element—and thus the longer the sequence that is complementary as between the side elements and the nucleic acid sample—the greater the possibility of erroneously recognizing a mismatched sample, since the strength of hybridization, even given the presence of a mismatch, will be reasonably high.

Thus, one way to reduce erroneous recognition of mismatched nucleic acid sequences is to reduce the length of the side element oligonucleotides. Specificity is increased by shortening side-arms to 8-mers or even to 6-mers. These will still hybridize at room temperature, depending on stringency of wash, conditions of which are well known in the art. The mismatched oligonucleotides would use five or fewer nucleotides for pairing and will form highly unstable binding at room temperature.

This solution, however, presents its own problem: the relatively short overall length, 12–16 nucleotides, used for recognition leads to a concomitantly reduced overall strength of the hybridization required to restrain the signal responsive moiety of the cleaved signal elements. Use of ligase, as depicted in FIGS. 2E–2F, partly solves this problem. Ligation will not only provide a stronger bond, but will further act to ensure selectivity, since DNA ligase will not join oligonucleotides if there is a mismatch near the end of the oligonucleotides. Because the oligonucleotides are short, no mismatched base pairs are accepted. Ligase serves as a very strict double-check for the match of the oligos.

An alternative, and complementary, solution, uses the triple recognition principle illustrated in FIG. 2D–2E constructively to shorten the test sample sequence available for hybridization to the cleavable signal element side elements. A soluble specificity-enhancing oligonucleotide, for example an 8-mer, which is complementary to the central part of the sample oligonucleotide, is added to the sample solution prior to contacting the assay device with the fluid sample. This 8-mer hybridizes well under the testing conditions. The side elements of the cleavable signal elements recognize six nucleotides in the immediate vicinity of the preformed duplex.

Ligation will ensure selectivity and will also provide a strong bond. Ligase will not join oligonucleotides if there is a mismatch near the end of the oligonucleotides. Because the oligonucleotides are short, no mismatched base pairs are accepted. Ligase serves as a very strict double-check for the match of the oligos.

Currently DNA ligase T4 is preferred. It couples the 3'-hydroxy and the 5'-phosphate termini of hybridized oligonucleotides, if there is no gap or mismatching oligonucleotides nearby. It requires ATP and $Mg^{++}$ for the full activity. DNAs that lack the 5'-phosphate can be rendered a suitable substrate for ligation by phosphorylation with T4 polynucleotide or similar kinase.

It will be apparent that the soluble specificity-enhancing oligonucleotide, shown here as an 8-mer, that is added to the test sample may be designed to position the potential mismatch near the sample ends, where mismatch will be most disfavored for binding to the side elements.

Moreover, because addition of ligase ensures a covalent loop, stringency of wash may be increased by addition of chaotropic agents and/or by heating to remove any unselective oligonucleotides.

The "blocked" sample oligonucleotide suitable for and capable of binding correctly to the side elements may be mimicked, however, by a sample nucleic acid that possesses the requisite terminal hexanucleotide sequences directly connected to one another without the intervening 8-mer sequence.

As shown in FIG. 2D, further addition to the sample of a 10-mer with sequence equally drawn from the first side element oligonucleotide sequence and second side element oligonucleotide sequence will prevent such binding upon contacting the assay device of the present invention.

The combination 8+10+8 of the specificity-enhancing soluble oligonucleotides is presently preferred, but other combinations, such as 7+9+7 and 8+8+8 may be used.

A further method to increase specificity includes use of so-called padlock probes, in which circularized oligonucleotides are catenated, permitting extensive washing to remove weakly bound probes. Padlock probes can achieve a 50:1 discrimination between complementary and singly mismatched oligonucleotides (Nilsson et al., Science 265:2085 (1994)), while with conventional probes this ratio is typically between 2:1 and 10:1.

Oligonucleotide side members having the following sequences are prepared by automated synthesis so that each of them contains a terminal thio (or aliphatic amino) group, depending on the attachment site with the cleavable spacer molecule (5' end or 3' end).

| Ia: | 5'-CGGGTGTGG (SEQ. ID. NO. 1) | Ib: | CGGCCGCGG-3' (SEQ. ID. NO. 5) |
|---|---|---|---|
| IIa: | 5'-CGGGTGTGA (SEQ. ID. NO. 2) | IIb: | CGGCCGCGG-3' (SEQ. ID. NO. 5) |
| IIIa: | 5'-CGGGTGTGC (SEQ. ID. NO. 3) | IIIb: | CGGCCGCGG-3' (SEQ. ID. NO. 5) |
| IVa: | 5'-CGGGTGTGT (SEQ. ID. NO. 4) | IVb: | CGGCCGCGG-3' (SEQ. ID. NO. 5) |

The cleavable spacer molecules are synthesized with two aliphatic amino groups, in place of the protected hydroxy groups above-described, and one group is protected by monomethoxytrityl (MMT, acid labile) and the other group is protected by fluorenyloxycarbonyl (FMOC, base labile). After the removal of the FMOC-group, the amino function is allowed to react under aqueous conditions with 4-(N-maleimidomethyl)-cyclohexane-1-carboxylic acid N-hydroxysuccinimide ester (SMMC). Thiol derivatized Ia is added to the spacer molecule and allowed to couple to the spacer molecule. Subsequently, MMT is removed by treatment with acetic acid, and after washing with buffer, pH 8, SMCC is added, and oligonucleotide IIb is allowed to couple with the spacer molecule. The spacer molecules prepared above are attached to a polycarbonate substrate.

A test sample containing 5'-GCCCACACCGCCGGCGCC-3' (SEQ. ID NO. 6) is prepared and allowed to contact the cleavable signal element at a temperature that approximates the $T_m$ of the side members Ia and Ib. The temperature of the sample solution is heated to about 20 degrees Centigrade above the $T_m$. Subsequently, the signal element is treated with 0.1M sodium fluoride solution and washed. Spacer molecules remaining attached to the surface signal the presence of, and tethering by, 5'-GCCCACACCGCCGGCGCC-3' (SEQ. ID NO. 6)

The foregoing process is applied to the analysis of 5'GCCCACACTGCCGGCGCC-3' (SEQ. ID NO. 7) 5'-GCCCACACGGCCGGCGCC-3' (SEQ. ID NO. 8) and 5'-GCCCACAGCCGGCGCC-3' (SEQ. ID NO. 9), using, respectively, spacer molecules incorporating side members IIa and IIb, IIIa and IIIb, and IVa and IVb.

6.5 Example 5

Noncleavable Spacer Assay for Detection of Spermidine

Spermidine (N-(3-aminopropyl)-1,4-butanediamine) has one secondary and two primary aliphatic amino groups. Recognition of spermidine can be accomplished by any functional groups that can be coupled with amino groups with sufficiently high specificity. Because the presence of thiol groups introduced by other molecules in a sample can interfere with the amino group assay, however, the presence of thiol groups must be assayed simultaneously with amino groups.

Noncleavable aliphatic spacers terminating in carboxylic groups are synthesized and disposed on the solid surface substrate of an assay device as described hereinabove. Plastic microspheres are coated by standard techniques to display maleimido groups.

Two aliquots of each of three samples are separately incubated with the maleimido-coated plastic spheres, one aliquot per sample at pH 6, the other aliquot at pH 8. Amino groups present on components of the sample react at pH 8 with the maleimido group. In the presence of spermidine, reaction proceeds with modification of spheres to display amino groups. Thiol-containing components react only at pH 6 with the maleimido groups.

Into all aliquots (two per sample) is then added 1-ethyl-3-(3-dimethylaminopropyl)carbodiimide (EDAC). The aliquots are then applied to separate assay sites of the assay device. The device is washed, and then read in an optical disk reader.

In the presence of spermidine, plastic microspheres display an amino group available for bonding to the carboxylic group of the spacers. In the presence of EDAC, a peptide bond tethers the plastic sphere to the assay device substrate. Thiols form unstable thioester bonds that hydrolyze relatively fast.

For sample 1, binding is observed only for the aliquot incubated at pH 8, confirming the presence of diamine, diagnostic of spermidine, in the sample.

For sample 2, no binding is reported at pH 8, indicating the absence of spermidine.

For sample 3, a positive result is reported for both pH 8 and pH 6, indicating the presence of aminothiol in the sample, rendering the pH 8 test inconclusive for presence of spermidine. A separate test is thus performed, as follows. To differentiate diamines and aminothiols, the test with carboxylated plastic beads is performed as described above. Only diamine will form a stable bridge between two carboxylic groups. Finally, to detect any dithiol in the sample, both the plastic spheres and the asswsay site should be functionalized with maleimido groups and the test is performed at pH 6.

In the other embodiment the cleavable spacer can be used to bind the plastic sphere onto the BCD surface. The recognition protocol is analogous to one described above, except that the spacers must be cleaved in the end of the assay.

The present invention is not to be limited in scope by the exemplified embodiments and examples, which are intended as illustrations of individual aspects of the invention. Indeed, various modifications thereto and equivalents and variations thereof in addition to those shown and described herein will become apparent to those skilled in the art from the foregoing description and accompanying drawings. Such modifications are intended to be and are included within the scope of the appended claims.

All publications, patents, patent applications, and provisional patent applications cited herein are incorporated by reference in their entirety.

What is claimed is:

1. An assay device comprising:
a) a solid support substrate;
b) a cleavable signal element having:
    a signal responsive moiety; and
    a cleavable spacer for releasably attaching said signal responsive moiety to said substrate, said cleavable spacer having an end attached to said substrate, an end attached to said signal responsive moiety and a cleavage site intermediate said substrate-attaching end and said signal responsive end;
c) a first anchoring member having a first end attached to said substrate and a second end adapted to bind on a first site on a chosen analyte;
d) a second anchoring member having a first end attached to said signal responsive moiety and a second end adapted to bind on a second site on said chosen analyte; and
the signal responsive moiety remaining bound to the substrate after cleavage at the cleavage site only when said first and second anchoring members are bound to said chosen analyte.

2. An assay device according to claim 1, wherein said signal responsive moiety is adapted to reflect or scatter incident light.

3. An assay device according to claim 2, wherein said signal responsive moiety is a metal microsphere.

4. An assay device according to claim 3, wherein said metal microsphere is essentially a metal selected from the group of gold, silver, nickel, platinum, chromium and copper.

5. An assay device according to claim 4, wherein said metal microsphere is essentially gold.

6. An assay device according to claim 3, wherein said metal microsphere is ferromagnetic.

7. An assay device according to claim 1, wherein said first anchoring member and said second anchoring member include oligonucleotides.

8. An assay device according to claim 7, wherein said first and second anchoring member oligonucleotides are 5 mers–20 mers.

9. An assay device according to claim 1, wherein
    said first anchoring member has a first antibody or antibody fragment, and
    said second anchoring member has a second antibody or antibody fragment.

10. An assay device according to claim 1, wherein said solid support substrate is a plastic selected from the group of polypropylenes, polyacrylates, polyvinyl alcohols, polyethylenes, polymethylmethacrylates and polycarbonates.

11. An assay device according to claim 10, wherein said solid support substrate is polycarbonate.

12. An assay device according to claim 1, wherein said solid support substrate is fashioned as a disk.

13. An assay device according to claim 1, further having computer software encoded upon said support substrate.

14. An assay device according to claim 13, wherein said support substrate is a compact disc.

15. An assay device according to claim 13, wherein said support substrate is a digital video disc.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 9
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 1:

CGGGTGTGG                                                      9

(2) INFORMATION FOR SEQ ID NO: 2:

(i) SEQUENCE CHARACTERISTICS:
        (A) LENGTH: 9
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 2:

CGGGTGTGA                                                      9

(2) INFORMATION FOR SEQ ID NO: 3:

(i) SEQUENCE CHARACTERISTICS:
        (A) LENGTH: 9
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 3:

CGGGTGTGC                                                      9

(2) INFORMATION FOR SEQ ID NO: 4:

(i) SEQUENCE CHARACTERISTICS:
        (A) LENGTH: 9
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 4:

CGGGTGTGT                                                      9

(2) INFORMATION FOR SEQ ID NO: 5:

(i) SEQUENCE CHARACTERISTICS:
        (A) LENGTH: 9
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 5:

```
CGGCCGCGG                                                               9

(2) INFORMATION FOR SEQ ID NO: 6:

(i) SEQUENCE CHARACTERISTICS:
        (A) LENGTH: 18
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 6:

GCCCACACCG CCGGCGCC                                                     18

(2) INFORMATION FOR SEQ ID NO: 7:

(i) SEQUENCE CHARACTERISTICS:
        (A) LENGTH: 18
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 7:

GCCCACACTG CCGGCGCC                                                     18

(2) INFORMATION FOR SEQ ID NO: 8:

(i) SEQUENCE CHARACTERISTICS:
        (A) LENGTH: 18
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 8:

GCCCACACGG CCGGCGCC                                                     18

(2) INFORMATION FOR SEQ ID NO: 9:

(i) SEQUENCE CHARACTERISTICS:
        (A) LENGTH: 16
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 9:

GCCCACAGCC GGCGCC                                                       16

(2) INFORMATION FOR SEQ ID NO: 10:

(i) SEQUENCE CHARACTERISTICS:
        (A) LENGTH: 33
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 10:

TGAGACACCA GGAATTAGAT ATCAGTACAA TGT                                    33
```

-continued (2) INFORMATION FOR SEQ ID NO: 11:

(i) SEQUENCE CHARACTERISTICS:
        (A) LENGTH: 33
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 11:

CTAAATCAGA TCCTACATAT AAGTCATCCA TGT    33

(2) INFORMATION FOR SEQ ID NO: 12:

(i) SEQUENCE CHARACTERISTICS:
        (A) LENGTH: 15
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 12:

TAGATATCAG TACAA    15

(2) INFORMATION FOR SEQ ID NO: 13:

(i) SEQUENCE CHARACTERISTICS:
        (A) LENGTH: 15
        (B) TYPE: nucleic acid
        (C) STRANDEDNESS: single-stranded DNA
        (D) TOPOLOGY: linear (ii) MOLECULE TYPE: oligonucleotide (xi) SEQUENCE DESCRIPTION: SEQ ID NO: 13:

TATTCAGTAG GTACA    15